US008629755B2

(12) United States Patent
Hashim-Waris

(10) Patent No.: US 8,629,755 B2
(45) Date of Patent: Jan. 14, 2014

(54) VISITOR MANAGEMENT SYSTEMS AND METHODS

(76) Inventor: Mohammed Hashim-Waris, Madison, WI (US)

( * ) Notice: Subject to any disclaimer, the term of this patent is extended or adjusted under 35 U.S.C. 154(b) by 513 days.

(21) Appl. No.: 13/058,858

(22) PCT Filed: Aug. 14, 2009

(86) PCT No.: PCT/US2009/053828
§ 371 (c)(1),
(2), (4) Date: Feb. 12, 2011

(87) PCT Pub. No.: WO2010/019849
PCT Pub. Date: Feb. 18, 2010

(65) Prior Publication Data
US 2011/0248818 A1    Oct. 13, 2011

Related U.S. Application Data

(60) Provisional application No. 61/189,166, filed on Aug. 15, 2008.

(51) Int. Cl.
G05B 19/00      (2006.01)
G07B 15/00      (2011.01)
(52) U.S. Cl.
USPC ....... 340/5.52; 340/5.82; 340/5.84; 340/5.81; 340/5.61; 340/5.5; 340/5.53; 340/5.54; 340/5.83; 340/10.1; 340/572.1; 705/13
(58) Field of Classification Search
USPC ............. 340/5.5–5.54, 5.61, 5.82–5.83, 10.1, 340/572.1; 701/29; 705/13
See application file for complete search history.

(56) References Cited

U.S. PATENT DOCUMENTS 5,585,839 A    12/1996   Ishida et al.
6,218,963 B1 *  4/2001   Kawanabe et al. ........... 340/933
6,256,661 B1    7/2001   Terahama et al.
(Continued)

FOREIGN PATENT DOCUMENTS

KR    10-2005-0037826 A    4/2005
KR    10-2007-0091876 A    9/2007
WO       2004/053638 A2    6/2004

OTHER PUBLICATIONS

Notification of Transmittal of the International Search Report and the Written Opinion of the International Searching Authority, or the Declaration for International Application No. PCT/US2009/053828 (4 pgs).

(Continued)

Primary Examiner — Nabil Syed
Assistant Examiner — Muhammad Adnan
(74) Attorney, Agent, or Firm — K&L Gates LLP

(57) ABSTRACT

Various apparatus, methods, techniques and systems are disclosed for admitting, tracking, monitoring and processing data about visitors and vehicles that visit an access-controlled environment. A network having one or more greeting stations and a number of linked answering stations collects and manages data concerning visitors and/or vehicles in the access-controlled environment, and can manage or assist individuals in managing granting access to the access-controlled environment, monitoring visitors and vehicles present in the access-controlled environment, limiting movement and access to certain areas in the access-controlled environment and generating records and other data about each visit. Some embodiments of the network are also adaptable for use in providing traveler assistance and consular services for various types of individuals.

16 Claims, 37 Drawing Sheets

(56) References Cited

U.S. PATENT DOCUMENTS

| | | | |
|---|---|---|---|
| 6,595,417 B2 | 7/2003 | O'Hagan et al. | |
| 6,690,293 B2* | 2/2004 | Amita | 340/928 |
| 6,812,824 B1* | 11/2004 | Goldinger et al. | 340/10.1 |
| 6,819,218 B2* | 11/2004 | Mabuchi et al. | 340/5.3 |
| 6,945,303 B2* | 9/2005 | Weik, III | 160/188 |
| 6,972,660 B1* | 12/2005 | Montgomery et al. | 340/5.52 |
| 6,976,269 B1* | 12/2005 | Avery, IV et al. | 726/2 |
| 6,976,932 B2 | 12/2005 | Raghavan et al. | |
| 7,046,779 B2* | 5/2006 | Hesse | 379/202.01 |
| 7,123,126 B2* | 10/2006 | Tanaka et al. | 340/5.2 |
| 7,172,113 B2 | 2/2007 | Olenick et al. | |
| 7,173,532 B2* | 2/2007 | Hanle et al. | 340/573.1 |
| 7,243,024 B2 | 7/2007 | Endicott | |
| 7,330,774 B2* | 2/2008 | Hashimoto et al. | 700/245 |
| 7,412,396 B1 | 8/2008 | Haq | |
| 7,639,844 B2* | 12/2009 | Haddad | 382/115 |
| 7,796,022 B2* | 9/2010 | Birtcher et al. | 340/502 |
| 7,898,385 B2* | 3/2011 | Kocher | 340/5.52 |
| 8,176,323 B2* | 5/2012 | Anemikos et al. | 713/168 |
| 2001/0037366 A1 | 11/2001 | Webb et al. | |
| 2002/0013721 A1 | 1/2002 | Dabbiere et al. | |
| 2002/0078459 A1 | 6/2002 | McKay | |
| 2002/0120496 A1 | 8/2002 | Scroggie et al. | |
| 2002/0174003 A1* | 11/2002 | Redmann et al. | 705/8 |
| 2002/0184102 A1 | 12/2002 | Markopoulos et al. | |
| 2003/0069752 A1 | 4/2003 | LeDain et al. | |
| 2003/0095184 A1 | 5/2003 | Lin | |
| 2003/0167176 A1* | 9/2003 | Knudson et al. | 705/1 |
| 2004/0229569 A1* | 11/2004 | Franz | 455/66.1 |
| 2005/0001712 A1* | 1/2005 | Yarbrough | 340/5.82 |
| 2006/0041542 A1* | 2/2006 | Hull et al. | 707/3 |
| 2006/0081703 A1* | 4/2006 | Tran | 235/382 |
| 2007/0046426 A1* | 3/2007 | Ishibashi | 340/5.52 |
| 2007/0073520 A1 | 3/2007 | Bleines | |
| 2007/0103541 A1* | 5/2007 | Carter | 348/14.06 |
| 2007/0214059 A1 | 9/2007 | Duncan | |
| 2008/0130956 A1* | 6/2008 | Jordan et al. | 382/115 |
| 2008/0259155 A1* | 10/2008 | McLelland et al. | 348/14.03 |

OTHER PUBLICATIONS

International Search Report, International Application No. PCT/US2009/053828 (3 pgs).

Written Opinion of the International Searching Authority, International Application No. PCT/US2009/053828 (5 pgs).

* cited by examiner

FIG. 14
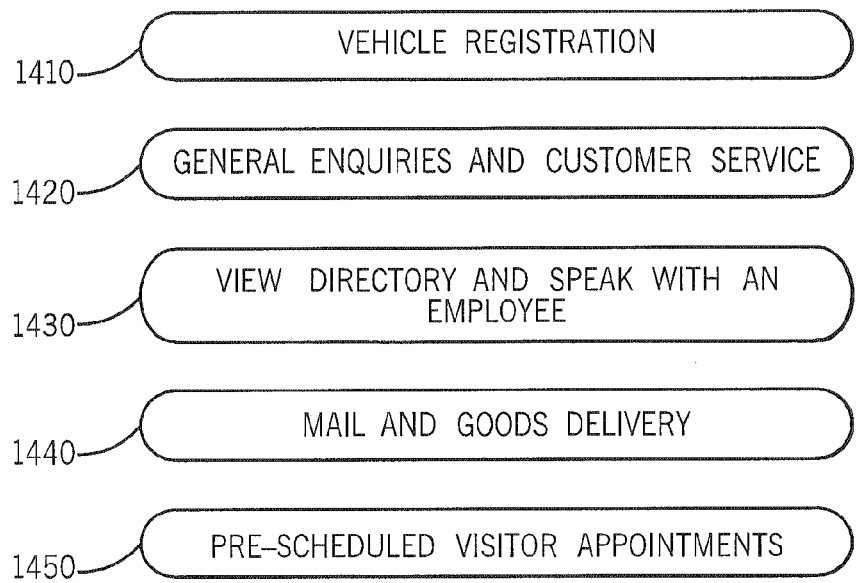
1410 — VEHICLE REGISTRATION
1420 — GENERAL ENQUIRIES AND CUSTOMER SERVICE
1430 — VIEW DIRECTORY AND SPEAK WITH AN EMPLOYEE
1440 — MAIL AND GOODS DELIVERY
1450 — PRE-SCHEDULED VISITOR APPOINTMENTS
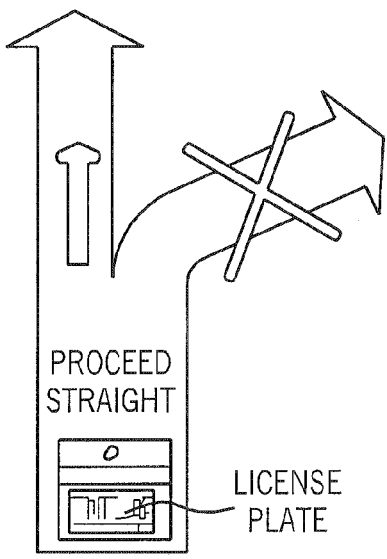
FIG. 18
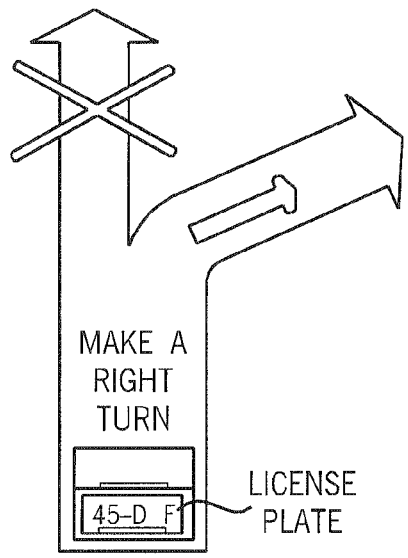
FIG. 19

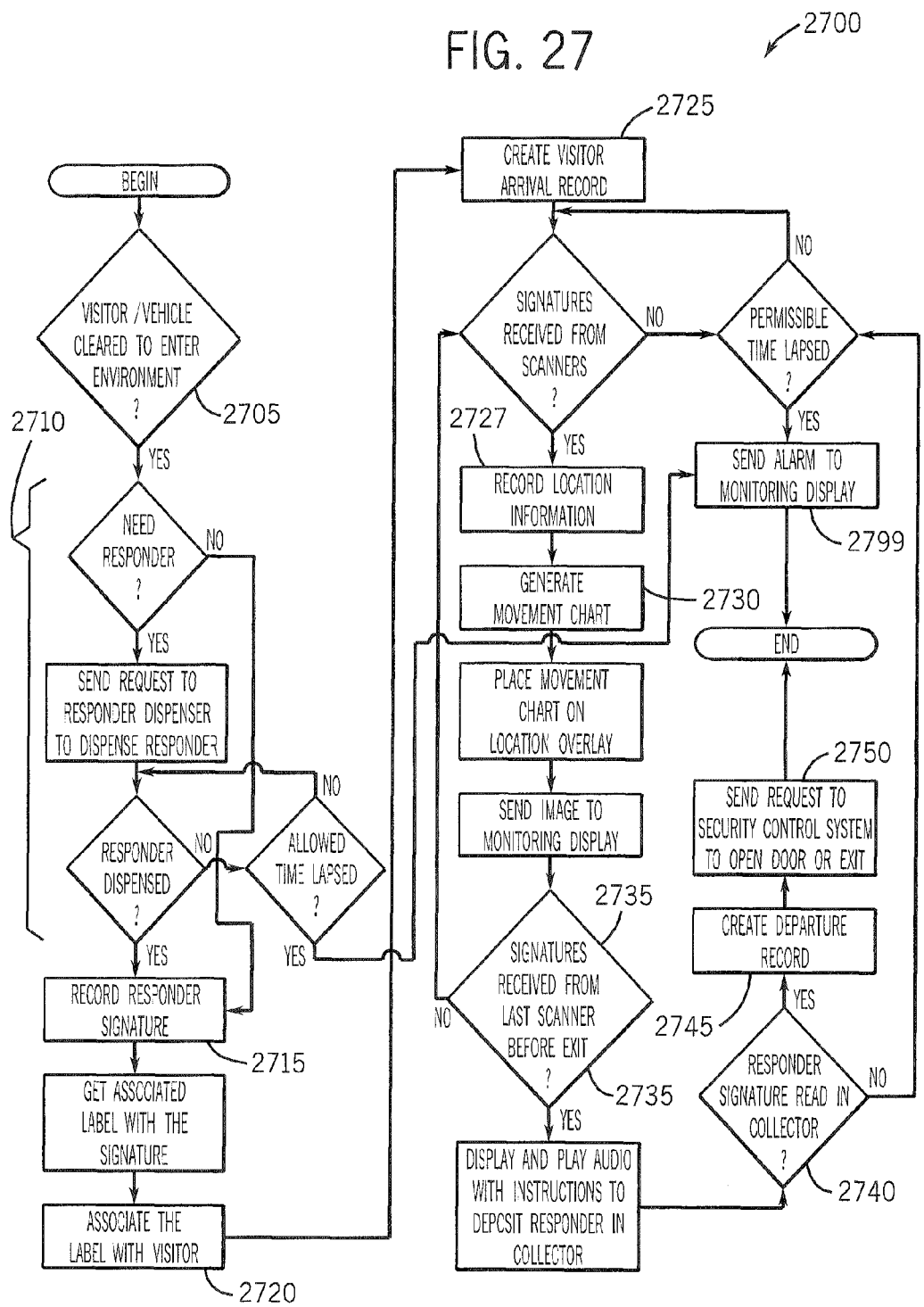

VISITOR MANAGEMENT SYSTEMS AND METHODS

PRIORITY CLAIM AND CROSS-REFERENCE TO RELATED APPLICATIONS

This application claims the benefit of priority under 35 U.S.C. §119(e) and any other United States or other law of the following:

U.S. Ser. No. 61/189,166 filed Aug. 15, 2008, entitled INTERACTIVE ASSISTANCE SYSTEMS, METHODS AND APPARATUS, the entire disclosure of which is incorporated herein by reference in its entirety for all purposes; and PCT International Application No. PCT/US2009/053828 filed Aug. 14, 2009, entitled VISITOR MANAGEMENT SYSTEMS AND METHODS, the entire disclosure of which is incorporated herein by reference in its entirety for all purposes; and PCT International Application No. PCT/US2007/053832 filed Aug. 14, 2009, entitled SUPPLY CHAIN MANAGEMENT SYSTEMS AND METHODS, the entire disclosure of which is incorporated herein by reference in its entirety for all purposes; and PCT International Application No. PCT/US2007/053836 filed Aug. 14, 2009, entitled SYSTEMS AND METHODS FOR DELIVERING MEDICAL CONSULTATION AT PHARMACIES, the entire disclosure of which is incorporated herein by reference in its entirety for all purposes.

TECHNICAL FIELD

Embodiments of the present invention relate generally to visitor management for controlled-access environments. More particularly, embodiments of the present invention address improved management of visitors, vehicles, packages and the like with reduced risk to personnel managing visitor greeting, facilitation, management, security and surveillance during a visit to a facility/environment and specifically to an integrated and automated capability to perform identity, personal and non-personal data management, access control, surveillance, communications, tracking and monitoring, enrollment and credential vetting methods for people and vehicles visiting an access-controlled environment.

BACKGROUND

Visitors need to be received and welcomed in a business environment and most businesses employ one or more dedicated receptionists to meet and greet visitors and to facilitate their visit by providing them with directions, delivering requested information to visitors and serving as a "gate-keeper" to the business. When a visitor arrives, the receptionist typically queries the visitor about the purpose of their visit; examines and validates the visitor's credentials to establish identity; establishes the visitor's status and decides to allow or disallow the visit; registers an allowed visitor by logging identity data in some form or fashion; notifies the visitor's host/destination of the visitor's arrival; provides directives to the visitor to complete the visit either by providing directions to the host, destination or visiting venue, advising as to how the visit will occur and transpire; opens or removes any physical barrier to the entry (e.g., opening a locked entrance or raising a barrier preventing entry of the visitor to the access-controlled environment); receives and/or delivers goods, packages, etc. that the visitor is there to deliver or pick up; provides information about the business and/or the visit in a variety of ways (e.g., publications, printed materials, electronic presentations, etc.). In many situations, visitors arrive at an environment (e.g., a campus, building, parking lot) in a vehicle. The environment may have restrictions, allowing only certain vehicles to enter. For example a military base may only allow registered vehicles belonging to the military and/or to military personnel that have necessary documentation and clearances to enter the environment. Occasionally, there are requirements for processing, registering, and allowing other vehicles on a short-term or long-term basis into the environment. Visitors seeking access to an environment may have to register themselves individually as well as registering a vehicle to enter the environment and may be monitored during their presence in the environment. Specific needs pertaining to security requirements of an environment govern such processes, procedures, and policies. In the current security environment, such requirements are more critical and must be implemented and enforced consistently, thoroughly and unemotionally. Embodiments of visitor management systems, access control systems, visitor monitoring systems and the like disclosed and claimed herein fulfill one or more needs in this art, and provide a variety of reception, security, and access-control functions using consolidation of business and security approaches and delivering those through one or more virtualization appliances, methods, and processes.

SUMMARY

Some embodiments of the present invention include apparatus, methods, techniques and systems for managing visitors and/or vehicles in an access-controlled environment. One or more greeting stations can be connected to a plurality of answering stations via a network to provide remote assistance with visitors, who also can use automated aspects of a greeting station for facilitating a visit to the environment. Available answering stations are prioritized based on collected visitor data so that skills-based routing/evaluation can be used to determine a visitor's needs. For environments that include vehicle use within the environment, additional features are provided, such as responders for use by visitors and/or vehicles so that visitor and/or vehicle movement can be monitored. Digital signage connected to the network used in connection with monitoring also helps in monitoring responders and in providing specific messaging, information and instructions to visitors and vehicles as needed. When used in connection with barriers and the like, such visitor monitoring systems can also limit visitor and vehicle movement to specified areas of the environment, enhancing visitor and vehicle flow management as well as security of the environment and personnel working therein. Some embodiments of these visitor monitoring systems can be adapted for use in connection with providing traveler assistance and consular services for various types of individuals.

BRIEF DESCRIPTION OF DRAWINGS

The present invention will be readily understood by the following detailed description in conjunction with the accompanying drawings in which:

FIG. 14 shows exemplary options presented by a visitor management system greeting station placed in a registration parking area.

FIG. 18 illustrates instructions for a vehicle operator identified by license plate photo when both the vehicle and the operator are found eligible to enter an access-controlled environment.

FIG. 19 illustrates instructions for an operator identified by license plate photo when an operator and/or a vehicle needs to register and get credentials to enter an access-controlled environment.

FIG. 27 is a flow diagram of an exemplary process embodiment for active monitoring and tracking visitors and/or vehicles inside an access-controlled environment.

DETAILED DESCRIPTION

Figure 1:
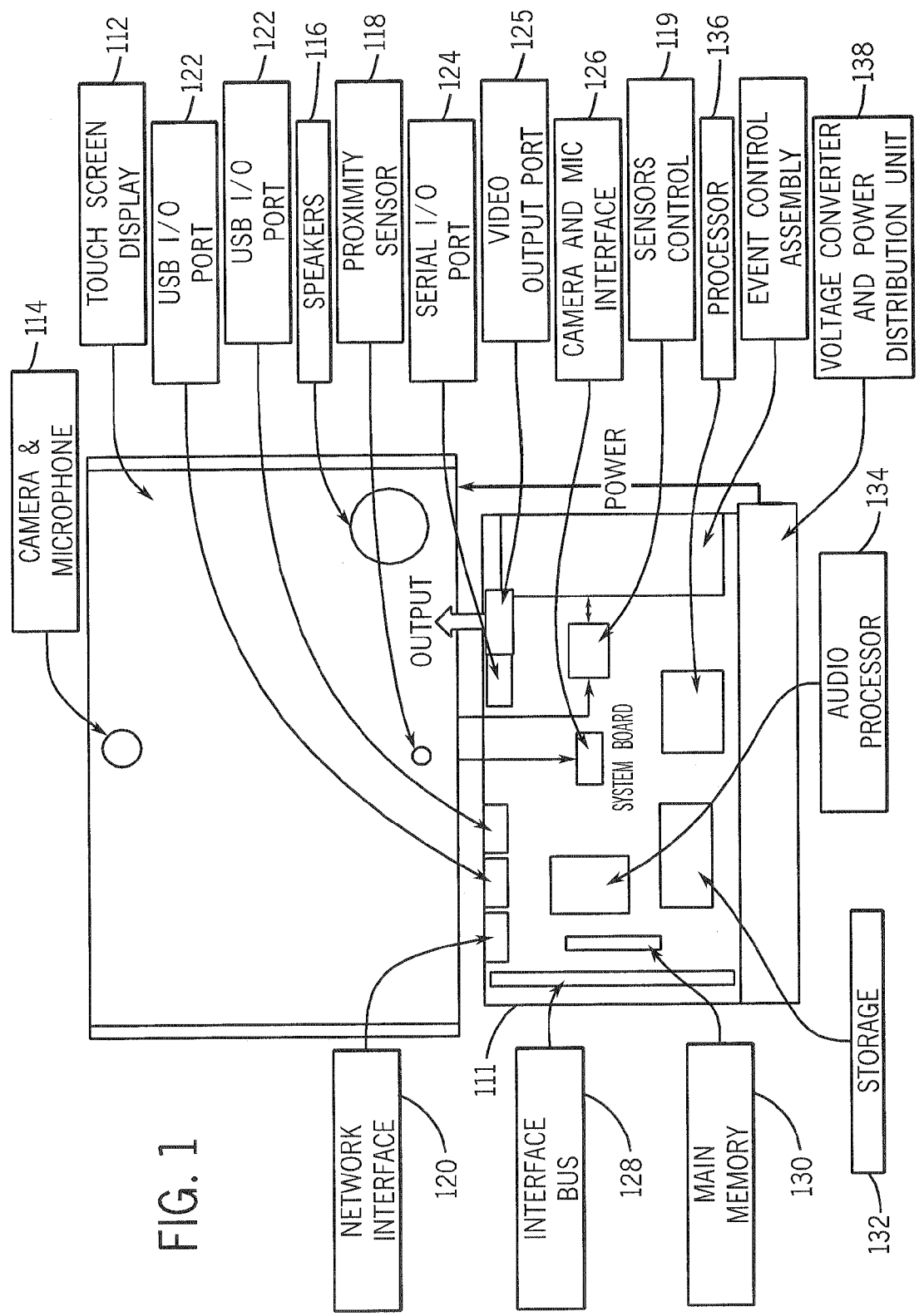
FIG. 1 shows a block diagram of one or more embodiments of a visitor management system apparatus.

The following detailed description will refer to one or more embodiments, but the present invention is not limited to such embodiments. Rather, the detailed description and any embodiment(s) presented are intended only to be illustrative. Those skilled in the art will readily appreciate that the detailed description given herein with respect to the Figures is provided for explanatory purposes as the invention extends beyond these limited embodiments.

Certain terms are used throughout the description and claims to refer to particular system components. As one skilled in the art will appreciate, computer and other companies may refer to components by different names. This disclosure does not intend to distinguish between components that differ insubstantially. Phrases such as "coupled to" and "connected to" and the like are used herein to describe a connection between two devices, elements and/or components and are intended to mean physically and/or electrically either coupled directly together, or coupled indirectly together, for example via one or more intervening elements or components or via a wireless connection, where appropriate. The term "chip" refers broadly to a hardware device that operates in a prescribed manner, for example to process data, and can include various types of such devices (for example, a field-programmable gate array (FPGA), a digital signal processing (DSP) chip, an application-specific integrated circuit (ASIC), an integrated circuit (IC), etc.). The term "system" refers broadly to a collection of two or more components and may be used to refer to an overall system (e.g., a computer and/or communication system or a network comprising one or more computers, communication components, etc.), a subsystem provided as part of a larger system (e.g., a subsystem within an individual computer), and/or a process or method pertaining to operation of such a system or subsystem. In this specification and the appended claims, the singular forms "a," "an," and "the" include plurals unless the context clearly dictates otherwise. Unless defined otherwise, technical and scientific terms used herein have the same meanings that are not inconsistent to one of ordinary skill in the art relevant subject matter disclosed and discussed herein.

Reference in the specification to "some embodiments," "one embodiment," "an embodiment," etc. of the present invention means that a particular feature, structure or characteristic described in connection with such embodiment(s) is included in at least one embodiment of the present invention. Thus, the appearances of the noted phrases in various places throughout the specification are not necessarily all referring to the same embodiment.

The visitor management and related systems deliver improved performance of many functions previously performed by a human receptionist, security guard, and/or assistant performing functions of value in an environment. The visitor management system and other, related systems disclosed herein reduce an environment's security vulnerabilities by reducing physical exposure of individuals to potential threats and by timely tailoring of access-control methods in response to changing security requirements and settings. The visitor management system is a self-servicing solution that makes a remote human attendant available using conferencing (audio and/or visual) when requested by the visitor. The visitor management system also enables cost reduction of operations by performing trivial business functions and saving the costs otherwise incurred in adding staff to perform the same functions. The underlying philosophy in such a visitor management system is "Self Service When You Want It—Live Assistance When You Need It."

Apparatus, systems and methods for facilitating entry and monitoring of a visitor, vehicle, package, etc. in a physical-access-controlled environment include a greeting station configured as an information appliance connected to one or more answering stations and/or answering station service applications running on computing, communication and/or information devices that are physically and/or logically connected to the environment network permanently or temporarily using various types of connectivity and/or communication. Different types of architecture, methods and configurations can connect greeting and answering stations to form a physical and/or logical system or network in embodiments of the present invention. Such apparatus, systems and methods for facilitating employee, visitor, and vehicle entry into a physical-access-controlled environment offers many benefits, including data gathering related to visitors, employees, and vehicles and allowing selected employees, visitors, vehicles physical access to a controlled environment. Visitors' disability requirements can be assessed and accommodated by modifying system appliances' and other devices' operations and configurations to meet the assessed requirements to permit interactive communication between the system and the individual and/or vehicle. Also, employee and/or visitor language needs can be assessed to allow system modification to permit employee/visitor interactive communication with the system. Skill-based routings of visitor requests contact a live assistance via audio and/or video, finding a live assistant operating an answering station located inside or outside the environment and fulfilling the visitor's contact request.

Embodiments allow a visitor to establish an audio/video session between a greeting station (or other visitor-usable or vehicle communication appliance) and an individual other than a live assistant whose contact information was manually or automatically selected by the visitor (or communication device in a vehicle). A responder (e.g., selected equipment, an individual or live assistant) can provide access to the controlled environment via algorithmic response, keyboard, keypad, number pad, dial pad, mouse click and/or touch capability from the respondent's communication device, during or after the session. Other systems controlling environment access points (e.g., security systems, electronics controlling access barriers, etc.) also can be linked to the system. The system can open entry barriers to permit physical access to the controlled environment and allow the employee, visitor, and/or vehicles access using one or both of automated and/or human decisions based on the employee, visitor, and/or vehicle data presented to the visitor management system. Individuals inside the environment can perform area surveillance in and around a greeting station or other component of the visitor management system from an answering station device. Also, text and/or graphical/picture maps and directions for destinations inside the environment can be printed by a system device.

Individuals operating answering stations can initiate a call and/or take control of a greeting station from the answering station and interact on the employee/visitor's behalf (e.g., providing inputs, making selections on a greeting station display, etc.), irrespective of the physical location of the greeting station device (collocated or remotely located). Likewise, an individual operating an answering station can take control of a display screen and display maps, drawings, pictures etc. and/or to draw, highlight, scribble on such objects to assist a visitor. Also, an individual operating an answering station remotely can enter visitor data prior to the visitor's arrival or during while the visitor is present. Employee data, meeting schedules, etc. can be downloaded, entered, updated, etc. to facilitate a pre-scheduled visit, for example based on an office scheduling system. Finally, embodiments of the visitor management system provide emergency communications, for example by delivering information about the emergency, instructions to follow, displaying emergency exit routes, etc. and opening all controlled access points for exits simply (e.g., by pressing or clicking on a single button).

Embodiments of the present invention can improve human resource, skills and time utilization, especially compared to individuals performing such tasks (e.g., a receptionist, security guard, payroll clerk, etc.) Direct savings can be realized in terms of employment costs by reduction or augmentation of staff and increased productivity of existing staff. Security and surveillance of the environment is improved, including the ability to monitor and perform surveillance remotely from a wide variety of safe locations. Extended hours of reception coverage can be provided without impairing service delivery. Moreover, the remote participation aspect of the visitor management system reduces exposure of environment personnel to active security threats and vulnerabilities.

Visitor flow management through environment access points is improved, as is traffic flow management in environments where employees/visitors bring in vehicles. Visitors and vehicles can be monitored and located more readily during a visit, and electronic visitor logs can be created and maintained more effectively for business, security and forensic needs. Visitor/vehicle data is more accurate because the data is either entered by the visitor himself, or it is obtained through an automated capture process. Sudden changes in security situations can be addressed with more agility and can include emergency communication system providing employees and visitors with audio and visual communications about emergencies, instructions to follow, emergency routes, and opening access points for emergency exit. With regard to employees, automatic collection and disbursement of employee data can be critical to some business applications (e.g., employee arrival/departure records, links to payroll data, etc.). The system can accommodate the needs of visitors with disabilities and/or speakers of foreign languages. These embodiments also provide consolidation and virtualization of services delivery and management.

Reference is made in detail to several embodiments of the current invention, examples of which are illustrated in the accompanying drawings. A "visitor" (the term "visitor" as used herein can mean one or more than one person, for example a group of individuals) attempting to enter an environment can be classified into three types. "Employees" are people who work in the environment or are employed by one or more businesses located in that or another environment and need to visit the subject environment for a specific purpose such as performing duties and tasks assigned by an employer. "Trusted Visitors" are people other than Employees having a legitimate business need to visit and access the environment to perform tasks and duties (e.g., mail carriers, delivery personnel, messengers, etc. who would have the trust of one or more environment's businesses to access one or more parts of the environment unescorted for short durations during specified or unspecified hours and/or days. "Occasional Visitors" are people other than Employees or Trusted Visitors having a need to visit and access the environment for specific business or personal needs (e.g., visiting an environment office or Employee, to attend meetings, solicit, etc.) for a short or predefined period. Such visits may be scheduled or unscheduled. Based on size, geographical location, mission, different types of visitors described above (i.e., employees, trusted visitors and occasional visitors) may bring vehicles (or other transportation), equipment, or non-business assets inside the environment temporarily or permanently. Additionally, visitors of these defined types may also have physical or language limitations (e.g., hearing or visually impaired, wheelchair-bound, etc.), or might not speak a common language. Employees and Trusted Visitors with such limitations often have predefined arrangements to accommodate their specific needs. For occasional visitors, however, assessing, determining and accommodating specific needs are made at the same time such people seek access to the environment.

Generally a reception process (e.g., the job description of a receptionist) provides assistance in facilitating a visit and implementing security rules using a prescribed philosophy about visitors in the environment. Most businesses' reception areas are isolated from the rest of the business and are located at an environment border, such as an entrance. In many cases, too, the reception area is detached from remaining offices, which results in isolation of the reception area staff from other staff. Environments with large physical/geographical parameters normally have multiple reception areas at convenient locations around the environment. Additionally, some environments have means in place to service the needs of visitors outside normal hours of operations. An after-hours answering service is one example of such a system, where an after-hours phone number is posted in the area. A person answering such a call may be remotely located in another environment (in the same or a different city, state and/or country). Also, businesses normally use a variety of methods to disseminate business-related information (e.g., regarding operations, marketing, etc.) and/or product/service information relevant to visitors' businesses, which can be disseminated via pamphlets, booklets, reports, etc. These publications also are available in a reception area. Another important function of the reception area is to keep visitors entertained while they are waiting, for example with electronic presentations, television, newspapers, magazines, etc. Other critical reception functions are identity management, enrollment, credential validation, surveillance and access-control validation/verification for the environment (e.g., buildings, campuses, complexes and military bases). Such functions typically use visual examination and validation of identification credentials, visitor registration, visit logs and/or similar methods. Based on the environment's security needs, a visitor and/or visiting vehicle (or other non-business assets) may need to be monitored while they are inside the environment. A variety of methods are used to monitor visitors and/or vehicles inside the environment including security cameras, personal escorts, and other surveillance modes.

In high security environments such as military installations and bases, identity management involves more than people alone, and extends to identity management of vehicles and other equipment entering and leaving secured areas, with or without visitors. If general access to the environment is secured and physical access is controlled, then certain security-related functions are performed by one or more receptionist-type individuals who have specific identity management responsibilities for both visitors and equipment. Such functions involve validating the purpose of a visit, ensuring that vehicles and equipment allowed to enter the environment meet security guidelines. If they do, only then will the reception gatekeeper permit a visitor, vehicle or equipment access to a controlled area, usually by operating access-limiting points to allow physical entry to the environment. In some cases the person being visited must go to an entrance and escort a visitor to a meeting place. Such authorizations and validations sometimes involve people inside the environment who have authority and responsibility to either approve credentials remotely or to come to the reception area personally to escort visitors and vehicles inside the environment, staying with a visitor until the visitor and/or vehicle leaves the environment. For example, if a visitor has a meeting with a given employee inside the environment, then the visitor may need to contact the employee, after which the employee may need to call the receptionist to let the visitor come to the employee's office, allow the visitor to bring a vehicle inside the environment, personally go to a reception area to receive the visitor, and/or send another person to the reception area as a representative to receive and accompany the visitor to the designated location inside the environment. All such activities involve costs (e.g., employee time and lost productivity time while completing this process).

Often, if visitor flow is not high in an environment, then security functions are also performed by a receptionist. In environments that have relatively low visitor flow, receptionists may be tasked with additional functions such as managing employee arrival and departure records for time keeping purposes, registering and/or inspecting vehicle authorizations for entering an environment, registering vehicles to grant entry to the environment, etc. There is, however, no real method for measuring productivity in each area of the business/security function assigned to the receptionist for the reason that all these functions are dependent upon receptionist availability, which is an inverse function of visitor flow—the more visitors being processed, the lower the availability of a receptionist to perform additional tasks.

This becomes more complicated in environments with multiple entrances, each with a controlled access point, and in environments where visitors must enter together with vehicles or other transportation. In such environments an additional task of non-person identity management (e.g., vehicle identity management) also must be performed. In view of increased security requirements in many settings these days, this also places receptionist/security individuals at greater risk and exposes them to potential security breach events. Staffing each such entrance with human resources thus results in additional employment costs for "less productive" business functions and increases threats to personal security. Another problem involves staffing visitor entrances during breaks or other absences of a receptionist and/or security guard, when replacement resources must be utilized from a resource pool which otherwise delivers a direct business-related objective. All reception areas must be staffed, otherwise some method of notification needs to inform people inside the environment that a visitor has arrived. Such methods involve a "ring bell" to call, video capture of the visitor, and/or sending images to monitoring stations inside the environment.

Conventional visitor reception systems use a human receptionist to implement functions (e.g., visit facilitation, visit management, control and monitoring of physical access to the environment) critical to business environment safety, security and operations. Using human resources to deliver such functions represents significant cost to a business, and increases management complexities with changing security or other requirements. Such costs can be substantial as such individuals are likely to spend all or a substantial amount of their time performing relatively trivial functions deliverable by one or more embodiments disclosed herein. Also, for personal security, reception staff are exposed to potential harm from a visitor and/or vehicle. Moreover, the ability to quickly react to a changed situation such as security alerts, etc. is minimal in most conventional methodologies; enhancing such capability is another cost factor to the environment.

Conventional reception methods also depend on certain methods of examining a visitor or vehicle for threat evaluation, such as visual inspection by a receptionist, a "gut" feeling or vibe about a given situation, comparing a name, picture, license plate, etc. with a watch list, ensuring that a license plate actually belongs to the vehicle on which it is displayed, etc. Updating each entry point's information incurs significant costs and may not be current or consistent, thus leaving a chance that someone or some vehicle representing a potential threat may enter the environment because the reception point did not have the latest information when processing the visitor and/or vehicle. If the environment requires monitoring of visitors and vehicles from entry time to departure, then an escort is provided to each visitor/vehicle, which utilizes significant human resources and adds considerable operational costs to the environment as well as an increased exposure to security risks for the escorts.

A visitor management system that caters to the needs of a variety of visitors and performs a variety of visit management functions would represent a significant advancement in the field. A visitor management system according to one or more embodiments of the present invention includes identity management, registration, environment access control, surveillance, visitor enrollment and credential vetting, advising a visitor about how the visit will be conducted and facilitated, connecting the visitor to a destination or host using audio and/or visual methods, disseminating selected visitor information using audio, visual, and/or printed materials, examining documents to establish identity, collecting data to verify identity, validating identity credentials, examining vehicle clearance to enter, and validating the vehicle data before allowing access to the environment. There is also a need in the art to separate visitors and vehicles into two classes—those that have necessary identity and clearance credentials to enter the environment and those that do not have such credentials and will need such credentials temporarily and/or permanently so that flow of each class of visitor and/or vehicle is managed efficiently and effectively. Further, in view of evolving and typically more demanding security needs, there is a need to monitor the visitor and/or vehicle inside an environment for the entire duration of their stay in a high security environment such as military bases, etc. in an automated manner. There is also a need to improve environment access to authorized users by operating and removing barriers to entry (e.g., unlocking doors, raising barriers, opening gates) either automatically or by taking input from other individuals and/or devices without distracting them from work or leaving their locations which may be collocated or remote. There is also a need to be able to connect a visitor with an individual belonging to the environment (whether or not that individual is inside or outside the physical environment at that time) using telephonic, video, audio or other methods if the visitor requests such connectivity for any reason (i.e., "live help"). Also, there is a need to improve personal security for individuals performing reception functions, by reducing their physical exposure while performing reception tasks and/or inexpensively updating security watch lists, etc. in order to reduce access of unwanted persons or vehicles to a security-controlled environment.

Embodiments of a visitor management system provide apparatus-implemented systems and methods for virtual reception and/or visitor management at one or more environment access points. As used herein, the term "environment" applies to any area defined by limited access (e.g., a building, group of buildings, hospital, campus, airport, amusement park, stadium, military or non-military base, etc.) where a receptionist or other, similar gatekeeper may be used. Where multiple buildings or the like are viewed as a single environment, the multiple areas may or may not be connected physically and/or logically using networking and communication technologies. The visitor management systems and methods are not limited to any particular environment, however, and may be used in any environment in need of reception assistance.

Figure 2:
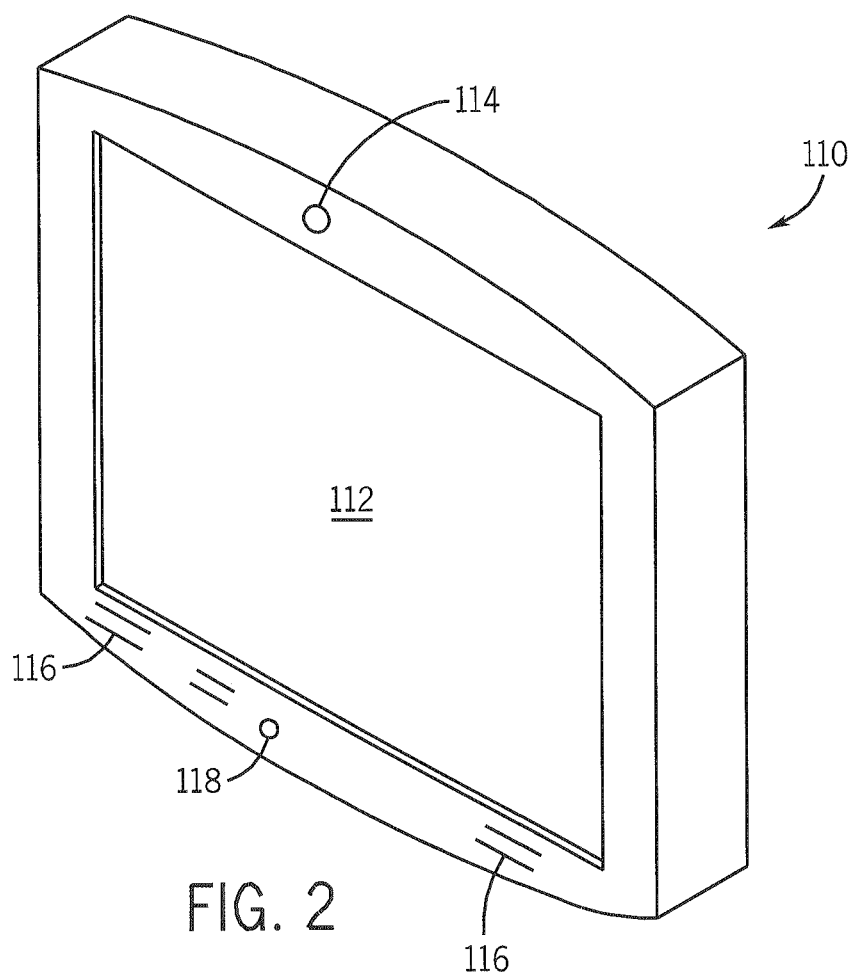
FIG. 2 shows one embodiment of a visitor management system greeting station.

FIGS. 1 and 2 illustrate a greeting station apparatus 110 that can be used with embodiments disclosed herein, for example in an access area (e.g., a waiting room or reception area) that includes an entryway to a access-controlled environment. Station 110 uses power and other outputs from a control module 111 that includes a touch screen 112 having an embedded camera and microphone 114. Touch screen 112, a key pad, a voice-activated control via microphone 114, a keyboard, etc. are examples of visitor option selection devices that visitors can use to make selections from various options available. One or more speakers 116 are provided near a proximity sensor 118 that transmits a signal when an individual approaches station 301 and has a sensor control 119. Appropriate interfaces are also provided, such as a network interface 120, USB I/O ports 122, a serial I/O port 124, video output port 125, camera/microphone interface 126 and an interface bus 128. One or more memory or storage units 130 can store information and data, including video and/or audio loops to be played in operating the greeting station 301. One or more processors can be implemented, such as a general-purpose processor 136, an audio processor 134 and/or others. Power is controlled and supplied via a voltage converter and power distribution unit 138. As will be appreciated by those skilled in the art, other resources on or in a network to which station 110 is connected can be exploited by the greeting station 301 as needed. Answering stations discussed below and used in embodiments of the present invention can be of similar construction or may be designed as desktop units that use some or all of the features of the station 110 of FIGS. 1 and 2.

Figure 3:
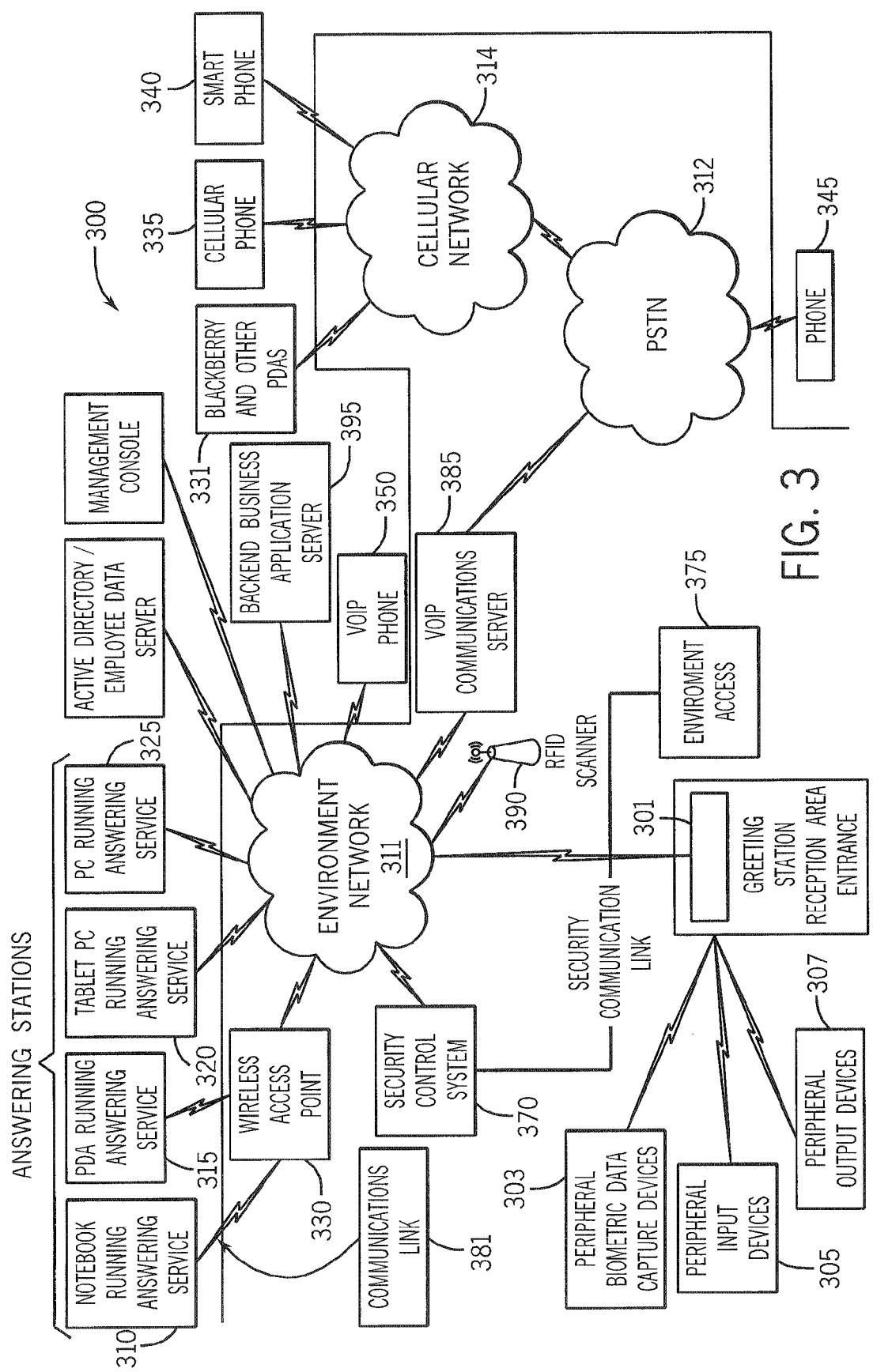
FIG. 3 shows an exemplary configuration of one or more embodiments of a visitor management system using at least one greeting station.

An exemplary visitor management system (VMS) 300 is shown in FIG. 3 where a greeting station 301 is an apparatus providing interactive communications between a "visitor" (an employee, trusted visitor or occasional visitor, as above) and the VMS 300. A management console 308 can be provided to allow management of VMS 300 from a central location, as discussed in more detail below. Acquisition/collection of visitor data and input devices are shown as Peripheral Input Devices 305, which are defined here as equipment, instruments, etc. used to provide user input for collection of visitor data by the VMS 300 and one-way or two-way communication between the user and the system. One or more specialized input devices for collecting visitor data, referred to as Peripheral Biometric Data Capture Devices 303 are also shown, and provide biometric data such as user fingerprints, face images, retinal scans, etc. Such input components are interfaced with the system using an I/O interfacing port of the system. Examples of such peripheral devices include keyboards, mice, scanners, barcode readers, etc., which allow visitors to enter visitor data such as a visitor's name, a company affiliation, scanned document data and information, etc. Visitor data collected during operation of VMS 300 can be stored on one or more memory devices or memory storage apparatus in network 311. Similarly, Peripheral Output Devices 307 are one or more devices providing system output to a user and include equipment, instruments, etc. delivering output from the system to a user in a variety of forms and fashions (e.g., printers, plotters, displays, etc.) Answering stations can be implemented on a variety of information, computing and/or communication devices for secure audio-video (AV) conferencing when a request for live assistance is made from the greeting station by a visitor or when an answering station user is selected for contact by a greeting station user. FIG. 3 shows an exemplary notebook computer answering station 310 communicating via the environment network 311 using wireless access pint 330, and a personal digital assistant (PDA) 315 using the same wireless access point 330 using one or more modes, protocols, connectivity methods and available networking technology for communication. A tablet PC answering station 320 and a personal computer answering station 325 are also connected to network 311 similarly.

Individuals inside the environment can be contacted by a visitor at a greeting station 301 using an internal name option "View Directory and Speak With an Employee" 420 in FIG. 4, which can use an active directory/employee data server 360. If the person contacted is not an answering station user, then a phone system in the environment can be used for audio communication between a greeting station visitor and the person being contacted, where the phone system is part of the prioritization of available answering stations and/or available responding resources and capabilities of individuals associated with the answering stations, for example within the environment and/or system 300. To execute such audio calls, the VMS 300 is integrated with a phone system in the environment. For illustration purposes, the visitor management system is shown integrated with the Voice over Internet Protocol (VoIP) server 385 in FIG. 3, which provides voice phone services to VoIP phone set 350. The integration allows a visitor at greeting station 301 to talk to the person inside the environment, but also enables the person receiving the call to provide the visitor access to the environment (e.g., by unlocking a reception area door, removing a barrier physically controlling access to the environment) using a phone dial pad and, for example, entering a personal authorization code. In one embodiment, an entryway such as door 375 is located in an access area of an access-controlled environment and is a controlled environment access point coupled to a security control system 370 that can send an "unlock" signal to door 375 in response to a variety of keys, including processes or the like according to one or more embodiments of the present invention. A person contacted inside the environment can authorize the VMS 300 to use alternative methods to call, thus allowing the VMS to search and locate the person using a BlackBerry device 331, cell phone 335, smart phone 340 or a POTS phone 345 at home or elsewhere. Irrespective of the location of the person being contacted (e.g., at home, traveling, another city, state, etc.), the VMS 300 enables the answerer of a call from a greeting station 301 to remove the barrier of entry for the person who initiated the call by using his/her device of communication used for answering the call to enter his/her authorization code and grant the requester access to the environment by entering authorization code. VoIP server 385 is one example only and VMS 300 can use other types of phone systems such as analog or digital PABX/PBX, SIP-based phones, etc. All the physical components used in a VMS embodiment can be interconnected physically and/or logically using networking, telecommunications and communications apparatus, processes, methods and technologies. All such apparatus, processes, methods and technologies are shown as clouds in network 311, public switched telecommunications network (PSTN) 312 and cell network 314. Physical and/or logical linking between devices and/or networks is shown as a communication link 381 in FIG. 3 for illustration purposes.

Visitor selection option devices such as those discussed in connection with greeting station 301 can provide visitor options like those shown in FIGS. 4A and 4B, overall operation of which are shown in one or more embodiments of the VMS 300 in FIGS. 5A, 5B and 5C. In operation, the process 500 begins at 501 with greeting station 301 initially waiting to sense a visitor's presence in the access area where station 301 is situated near an entryway. When a visitor (e.g., employee, trusted visitor, occasional visitor) enters the greeting station area at 510, a visitor proximity system in station 301 notes the presence at 515 using one or more sensors. A variety of such proximity sensors are known and one or more of these can be utilized in embodiments of the present invention, as will be appreciated by those skilled in the art. Once a visitor is sensed, station 301 plays a greeting at 520 and instructs the visitor to approach station 301 to begin the visit. Using the visitor proximity system sensor(s), VMS 300 monitors at 525 whether or not the visitor has approached station 301. If the visitor approaches station 301, then options such as those shown in FIG. 4A or 4B (discussed in more detail below) can be presented to the visitor. VMS 300 determines whether the approach was normal human behavior or not. This can be important because a variation in normal visitor behavior may indicate a potential disability and/or language restriction. VMS 300 uses one or more analyses to detect potential disabilities. For example, after reception area entry (determined, e.g., by a visitor detection system that includes a door sensor, switch, electric eye or the like), if the visitor does not approach station 301 or takes longer than an acceptable time period to reach station 301, that behavior can be an indication that the visitor is "hearing impaired" and did hear the audio loop, or that the visitor does not understand the language being used in the station greeting. Where the visitor might need assistance in this regard, a sub-module 580 determines disability and/or language status and an assessment is made at 585, after which process 500 can be modified at 590 to accommodate any visitor special needs. One exemplary operation of sub-module 580 is shown in FIG. 5B, which defines the process for identifying visitors with potential hearing impairment 592 and foreign language limitations 591, then setting up a method for communicating, greeting, and facilitating visits for such individuals before returning to process 500 of FIG. 5A. Similarly, FIG. 5C illustrates one process 593 for identifying visitors who may be wheelchair bound or who may have a visual impairment and a method of notifying live assistants to provide personal service to such visitors to facilitate their visit; returning to 580/585 in process 500 of FIG. 5A.

Figures 4A, 4B:
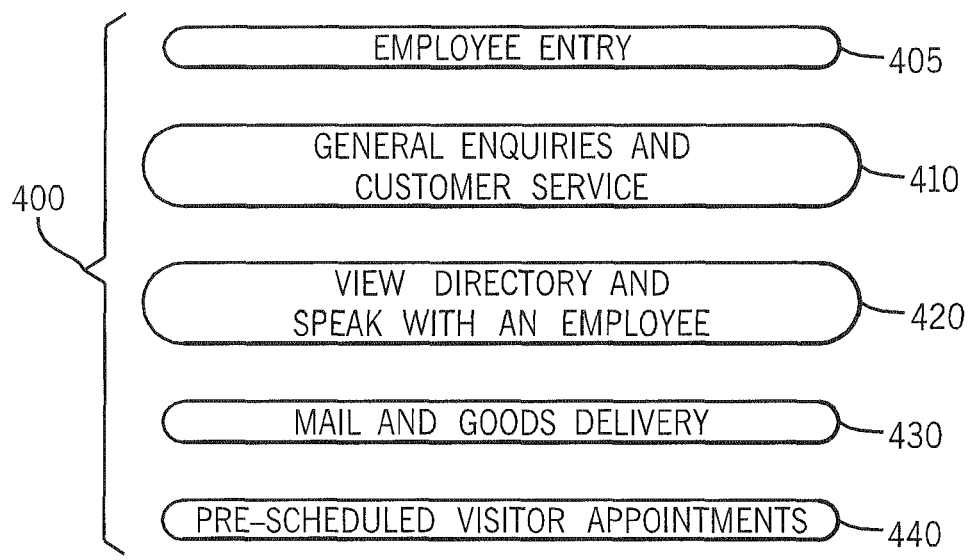
FIG. 4A shows user/visitor options available to a user/visitor at an exemplary greeting station of one embodiment.
FIG. 4B shows menu options available to a visitor/employee at an exemplary first entry point station of one embodiment.
Figure 5A:
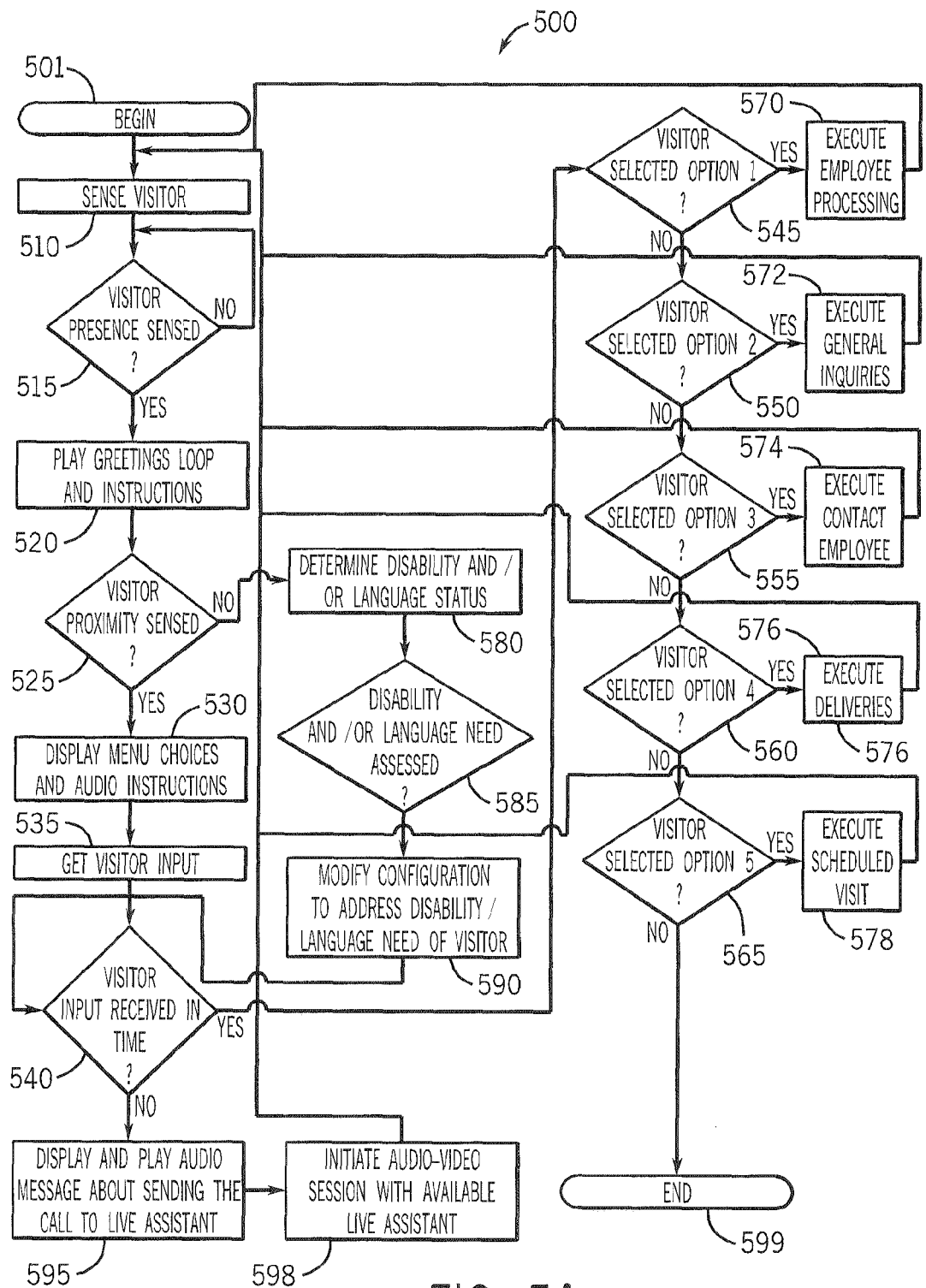
FIG. 5A is a flow diagram of an exemplary process executed in a visitor management system apparatus such as a greeting station.
Figure 5B:
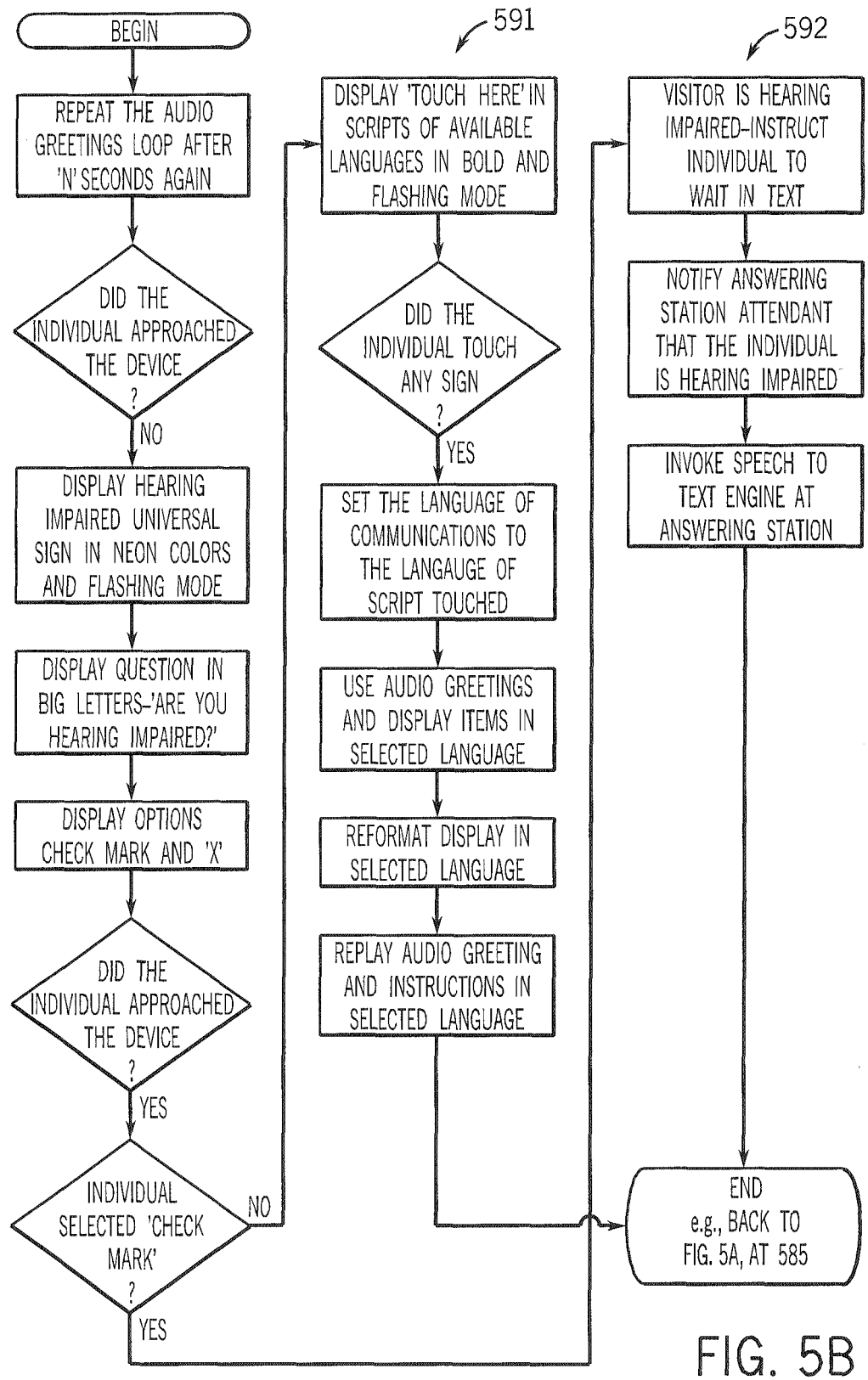
FIG. 5B is a flow diagram illustrating an exemplary process for assessing a visitor's disability and/or language barrier/restriction.
Figure 5C:
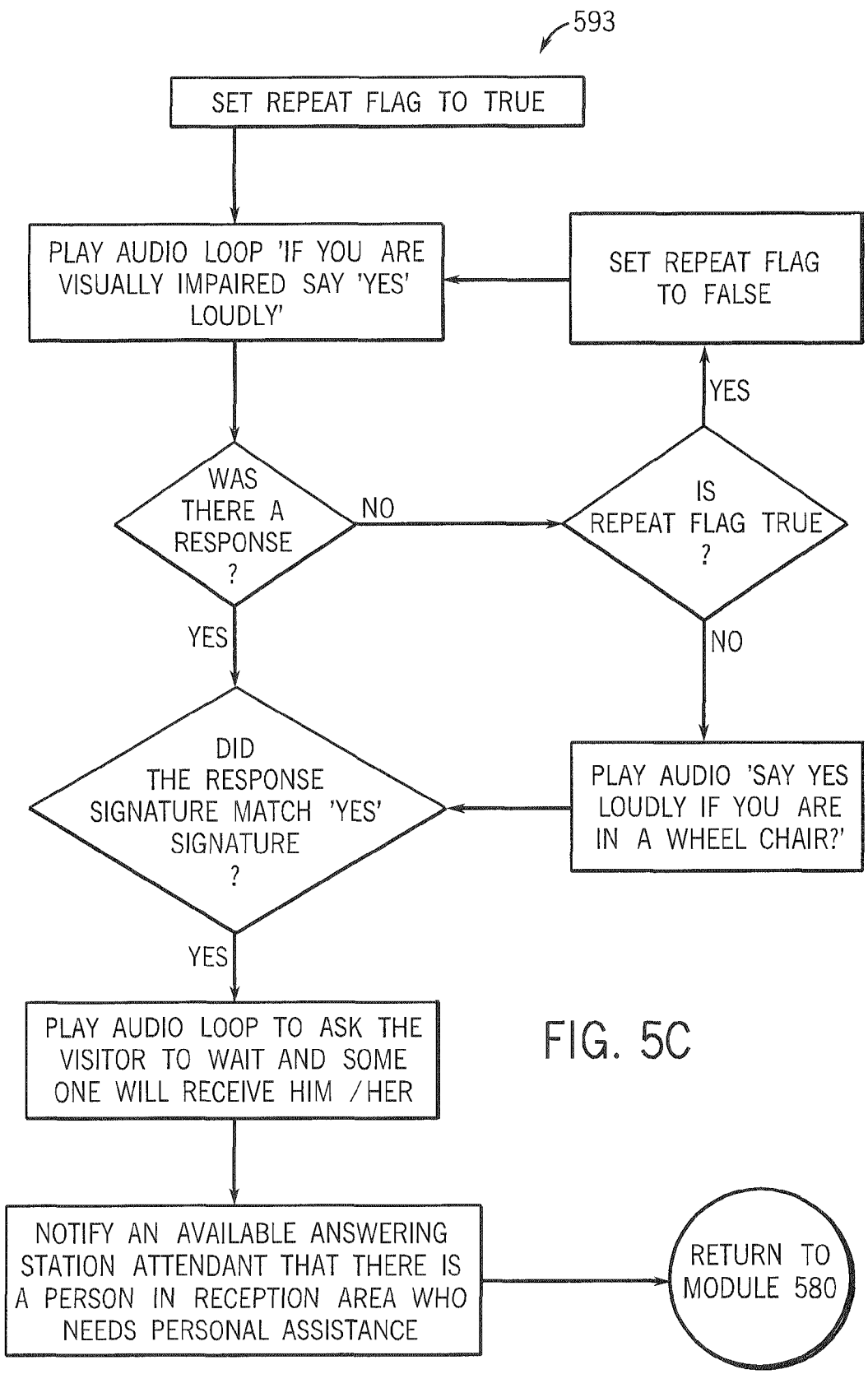
FIG. 5C is a flow diagram illustrating a continuation of an exemplary process to assess a visitor's disability status.

If no special needs are likely, then at 530 the visitor is presented with choices and instructions, such as those shown in FIGS. 4A and 4B. Once the visitor's input is received at 535, a decision is made at 540 about whether the visitor likely needs live assistance, for example based on whether visitor inputs were received in a timely fashion. Interactive communications are provided by the visitor in form of option selections, user inputs, reading of requested documents, etc. Station 301 initiates, responds to and/or instructs the visitor by playing audio loops and displaying text and graphics messages. Where timely responses are received by VMS 300, the process 500 moves to the ladder of choices 545, 550, 555, 560, 565. Where live assistance might be needed, the process 500 moves to call a live assistant at 595 and initiates the session at 598. Where the ladder of choices is implemented, an appropriate process 570, 572, 574, 576, 578 is executed.

Figure 6:
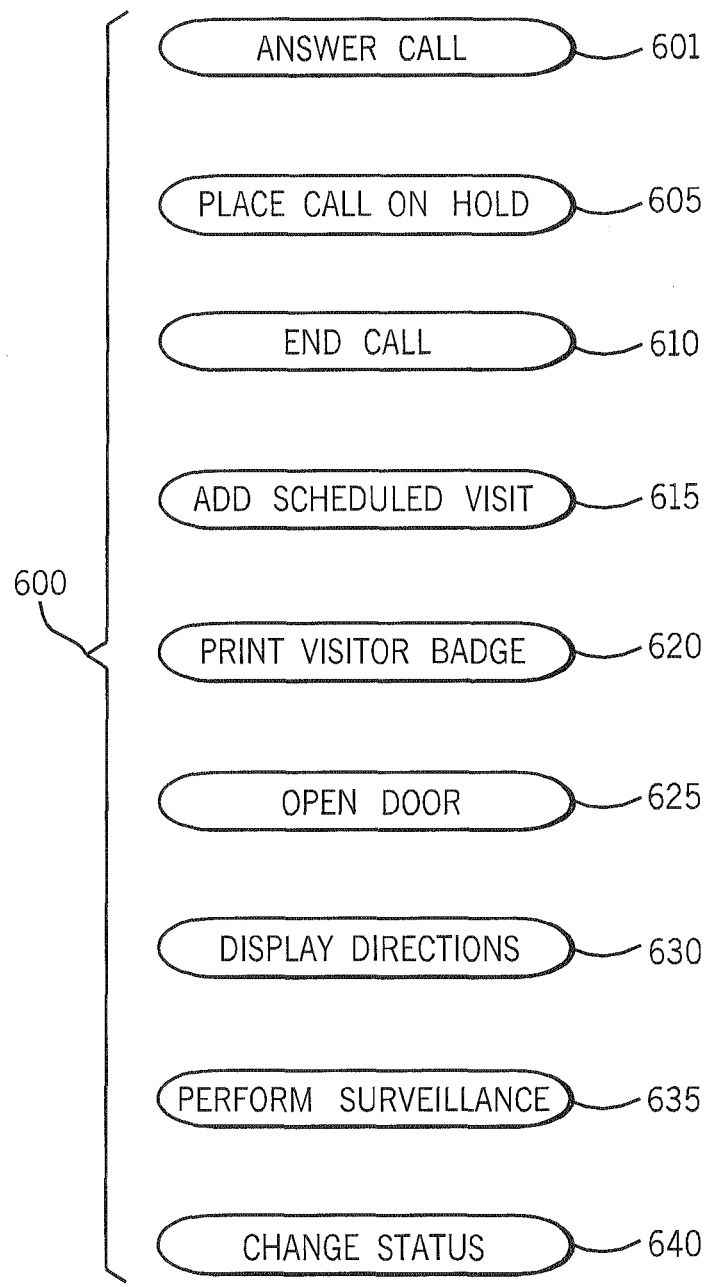
FIG. 6 shows exemplary menu options offered by an answering service at an answering station executing on an information appliance, computing device and/or communication device.
Figure 7:
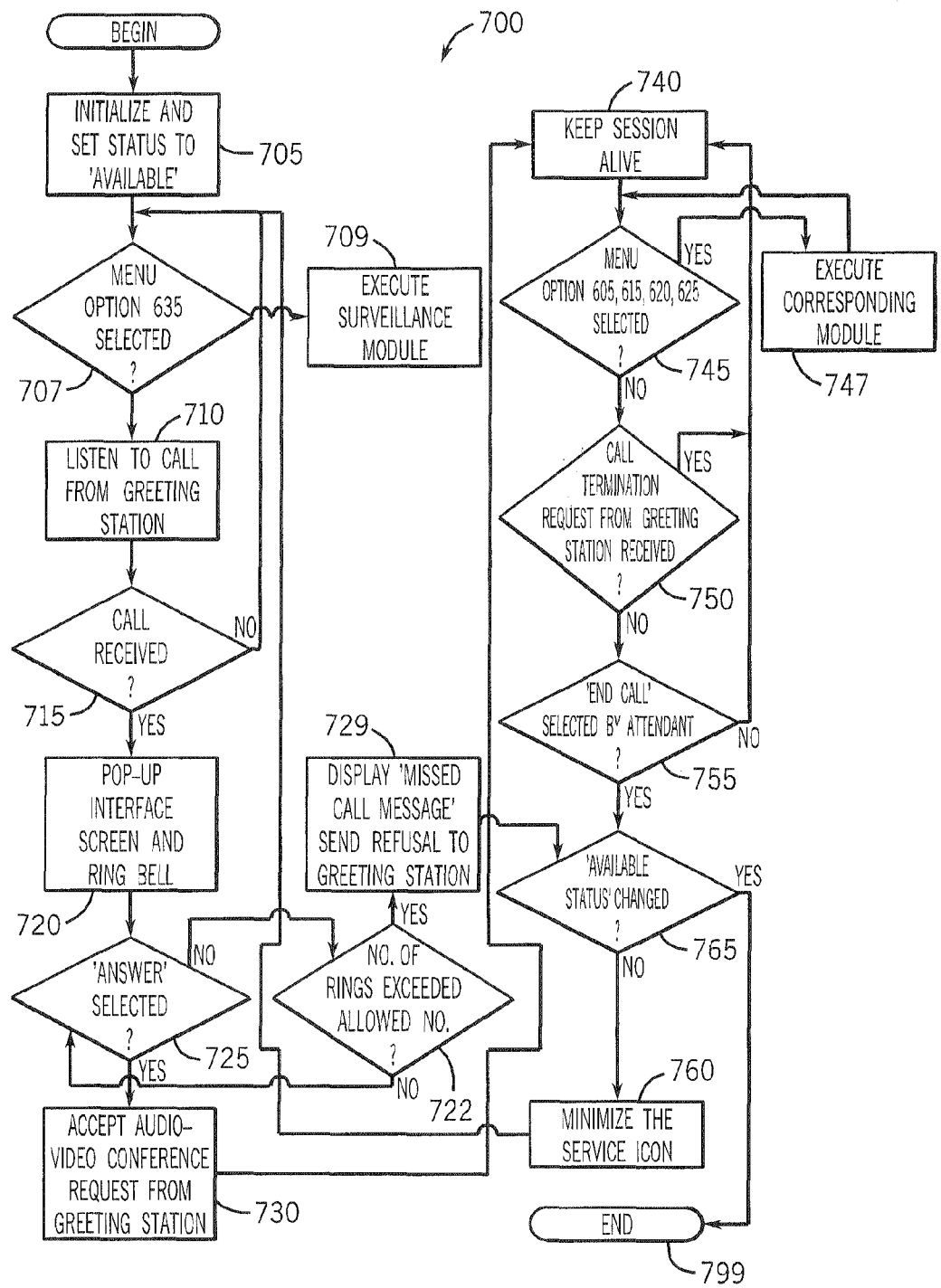
FIG. 7 shows an exemplary main process for a visitor management system embodiment answering service being executed at an answering station information appliance, computing device and/or communication device.

One answering station response process 700 is shown in FIG. 7, which begins at 705 with the answering station being set to "available" status. The surveillance option can be selected at 707 and the answering station executes that module at 709. Otherwise, answering stations that are part of the VMS 300 listen for and to calls from a connected greeting station at 710. The answering station device can continue to be useful for other business functions, such as a workstation or the like. When a call request is received by the answering station at 715, the "answerer" can be presented at 720 with options shown in FIG. 6. If the answering station does not answer the greeting station call, then various steps 727, 729, 765 can be executed to move back to "available" status. If the answering station operator accepts the request at 730, then the session is initiated and maintained at 740, allowing various other options at 745, 747, 750, 755, 760 and 765. The answering station operator can use this process to surveil and monitor the reception area where station 301 is installed using option 635 at any time, even when not "in session" with a visitor at the greeting station. The answering station operator can start the surveillance service 635 by bringing up the interface of FIG. 6 and selecting option 635. In response to contact from VMS 300, the answering station initiates a session with the selected station 301, turns on one or more cameras and starts receiving video, audio and any other data feed. Another feature of this process answering station operator's ability to place a call on hold (e.g., to have an internal conversation private from the greeting station visitor), the answering station operator can select "Hold," option 605, which stops all communication from the answering station to the greeting station, but continues to provide data feed from the greeting station to the answering station and changes the "Hold" button to "Resume." Once the "Resume" button is selected, audio-video-data feed from answering station to greeting station resumes. Option 615 can add a scheduled visit as an alternate way of updating a calendar if the system is not set up to automatically update from server 360 of FIG. 3, or if a visit needs to be scheduled between update intervals or instant arrangement. Option 620 allows the answering station operator to remotely print a visitor badge at a greeting station. Option 625 allows the answering station operator to grant access to the environment for the visitor at the greeting station. To further assist the visitor, the answering station operator can select option 630 and remotely display a map or instruction at the greeting station and/or take control of the greeting station display to draw, scribble, etc. graphic/visual information for the visitor to make a point, elaborate, explain or simply facilitate a visit.

Figure 8:
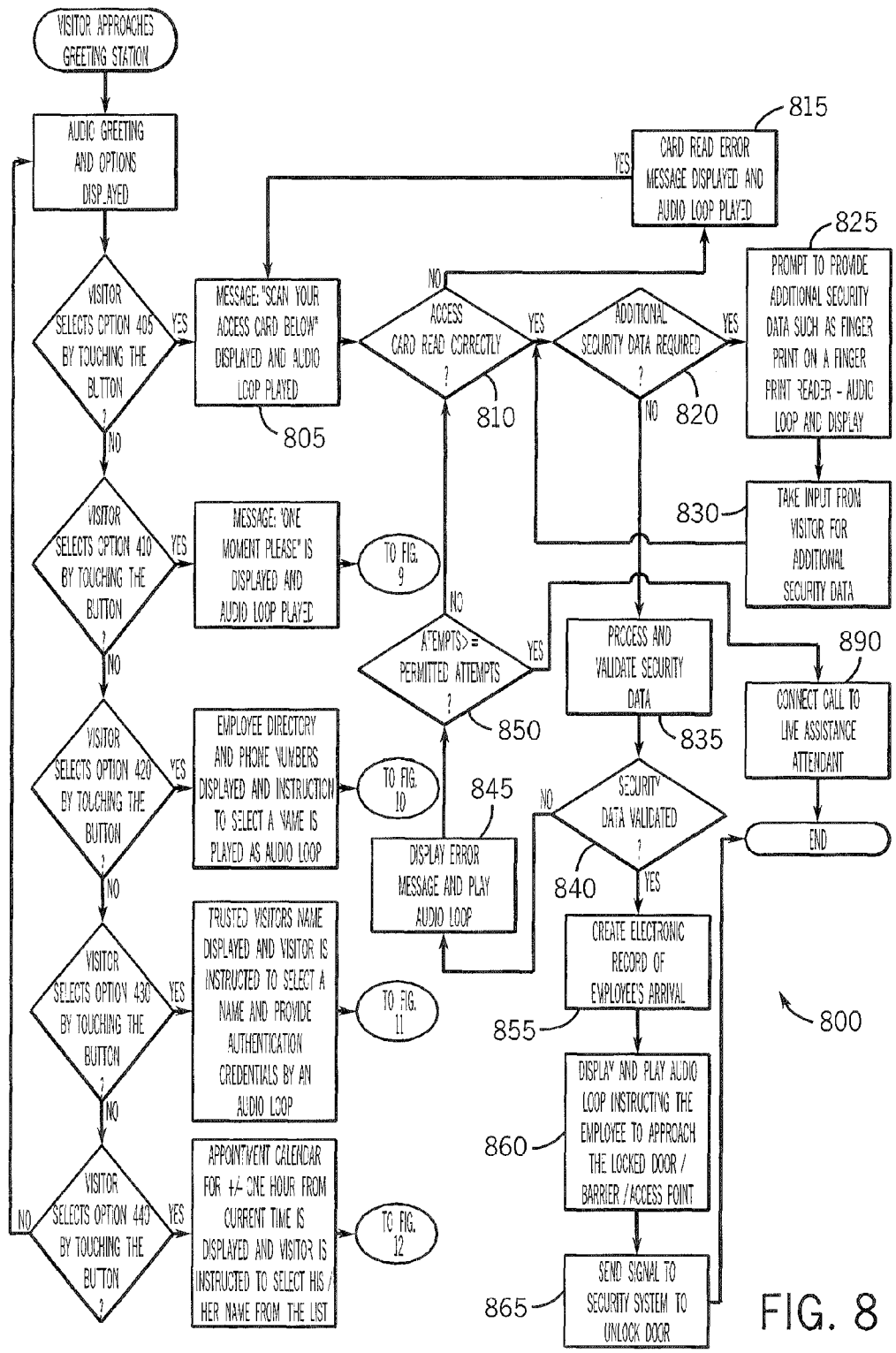
FIG. 8 shows an exemplary visitor interaction with a visitor management system embodiment when a visitor selects Option 405, 'Employee Entry' from the option menu of FIG. 4A.
Figure 9:
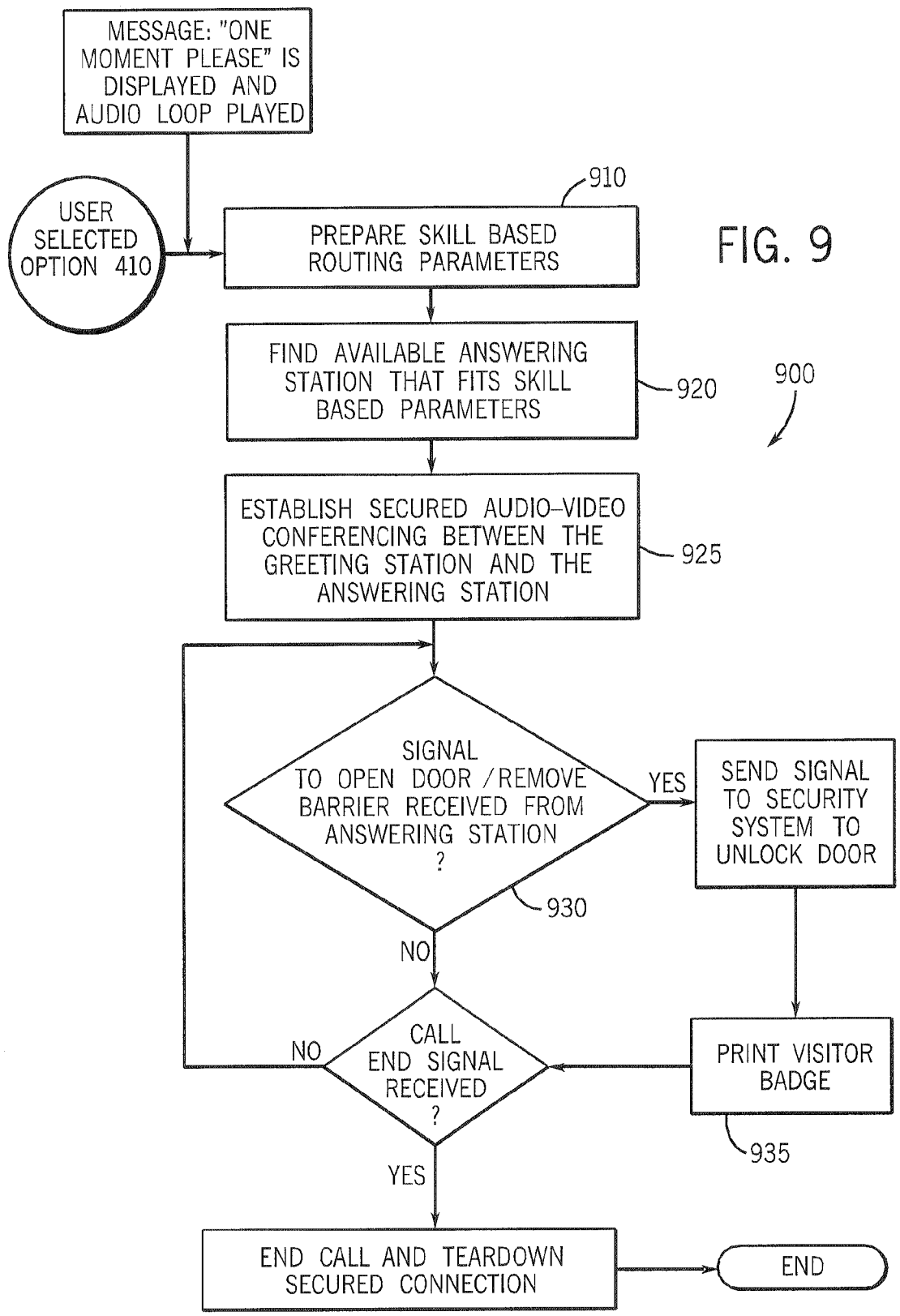
FIG. 9 shows an exemplary visitor interaction with a visitor management system embodiment when a visitor selects Option 410, 'General Enquiries and Customer Service' of FIG. 4A.

When a visitor selects option 405 on menu 400 of FIG. 4 (an exemplary main menu), then the process 800 shown in FIG. 8 is executed, where an access card can be scanned at 805, read correctly at 810 (or re-read after an error at 815). If additional security data is required at 820, then such data can be provided by the employee at 825, 830. Once the needed security data is collected, it significant processed at 835 and validated 840 (failure leads to an error message 845 and check on attempt number 850—a live assistant is called 890 when too many attempts have been made). When security data has been validated, an electronic record is made 855 and the employee is allowed to enter 860, 865. Similarly, when option 410 of FIG. 4 is selected, the process flow 900 shown in FIG. 9 is executed, beginning with preparation of routing parameters 910 and locating an available answering station at 920 that fits those parameters. A secure conference is established between the answering and greeting stations at 925 after which a decision to open the access door is made at 930 (if the visitor is admitted, a badge can be printed at 935).

Figure 10:
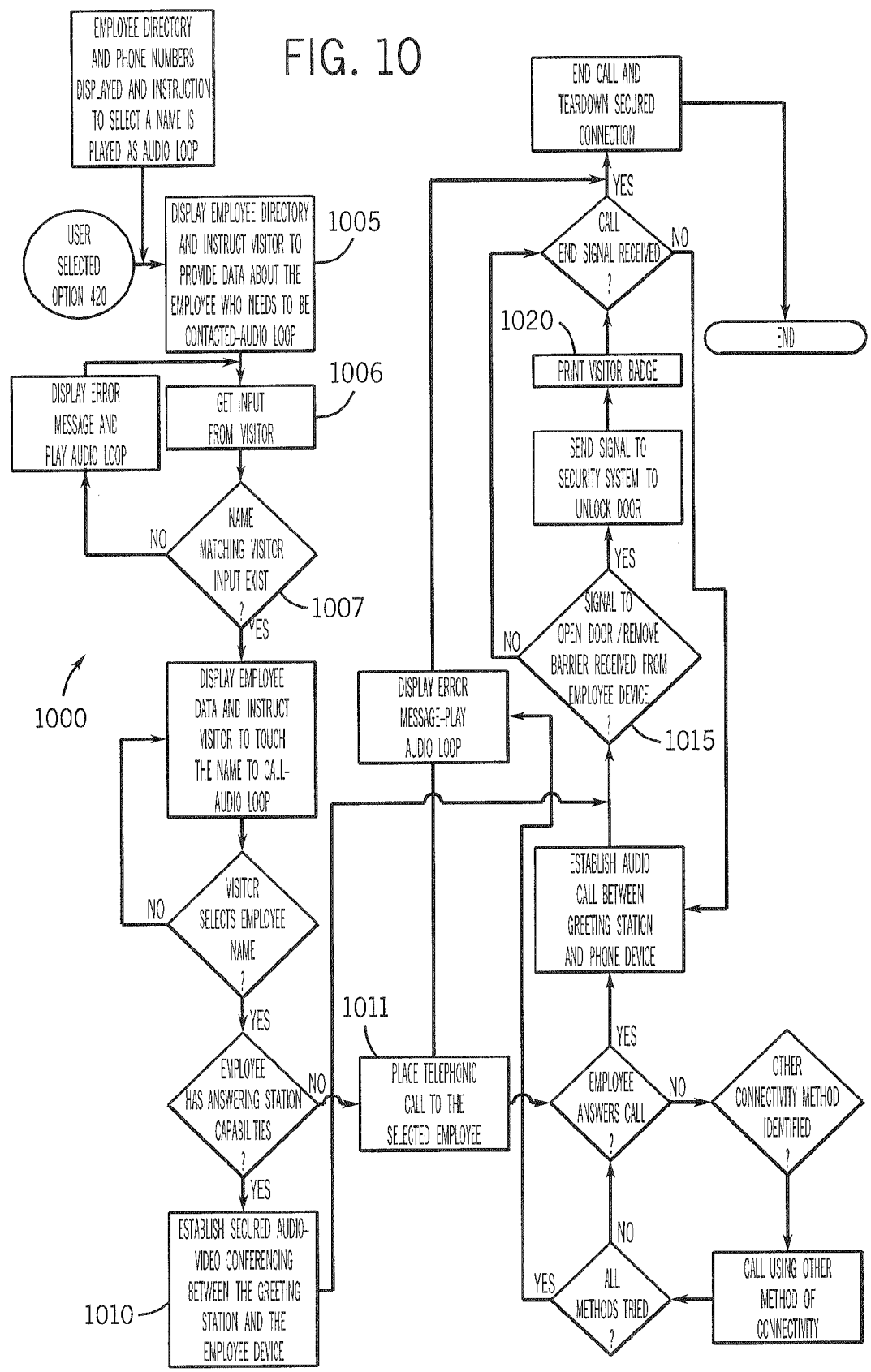
FIG. 10 shows an exemplary visitor interaction with a visitor management system embodiment when a visitor selects Option 420, 'View Directory and Speak With An Employee' of FIG. 4A.
Figure 11:
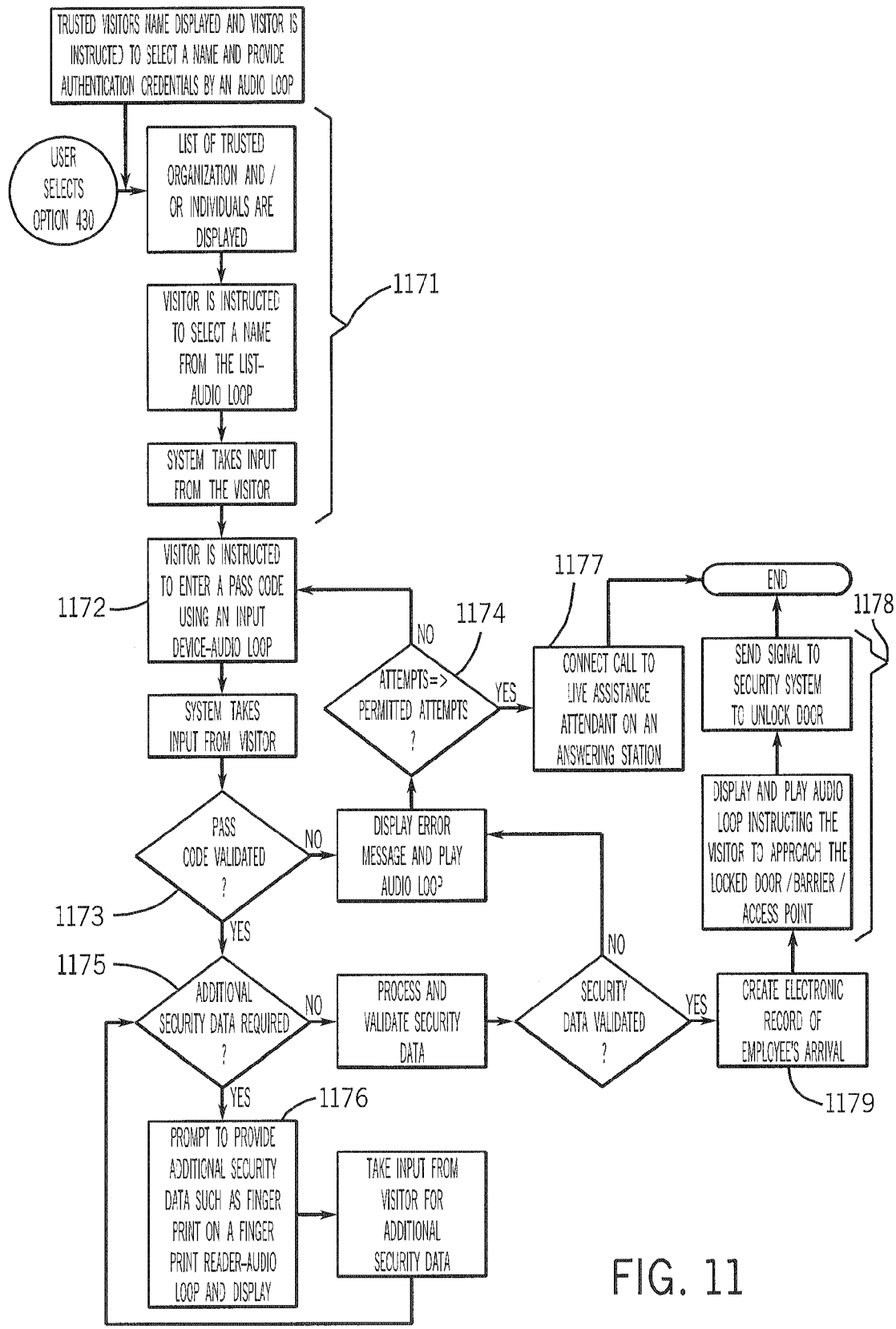
FIG. 11 shows an exemplary visitor interaction with a visitor management system embodiment when a visitor selects Option 430, 'Mail and Goods Delivery' of FIG. 4A.
Figure 12:
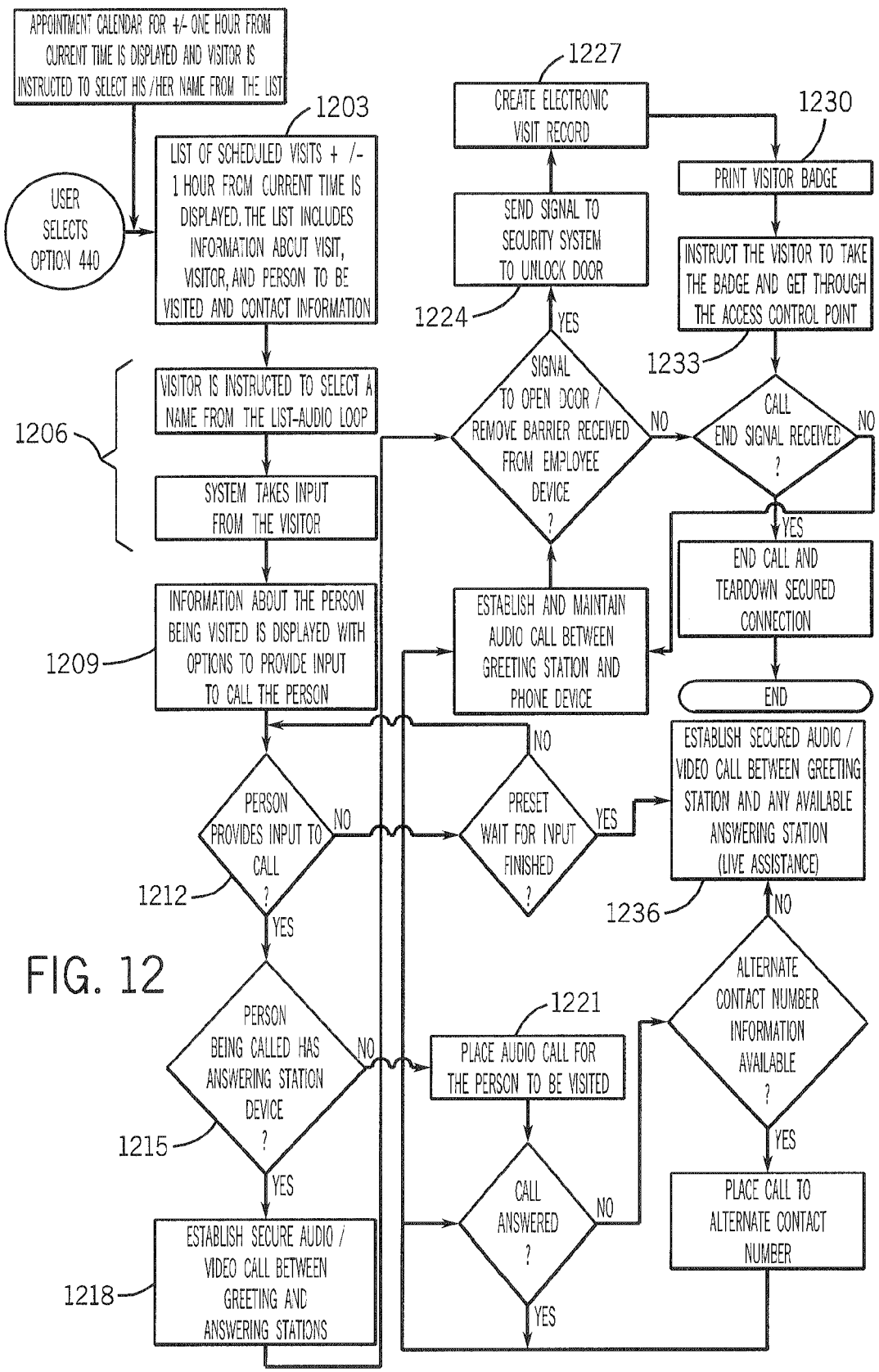
FIG. 12 shows an exemplary visitor interaction with a visitor management system embodiment when a visitor selects Option 440, 'Pre-Scheduled Visitor Appointments' of FIG. 4A.

When option 420 of FIG. 4A is chosen, process flow 1000 of FIG. 10 is executed, beginning with finding the correct employee at 1005, 1006, 1007. The employee is chosen at 1008 and contacted via an available answering station at 1010 or telephone 1011, if no answering station is available. Depending on the communication mode and the answerer's decision, the visitor can be admitted at 1015 and a visitor badge printed at 1020. When option 430 of FIG. 4A is chosen (typically in connection with a trusted visitor), process flow 1170 of FIG. 11 is executed, beginning with selecting a trusted visitor (or organization) at 1171 and then entering a pass code or other authorization at 1172 (as with the other processes noted herein, audio and/or video loops can be played to assist the visitor in the identification, registration, etc. processes), which can be verified at 1173. If the code is not valid, then additional attempts can be made 1174 or live assistance can be sought at 1177. If a valid code is presented, then additional security data might be collected at 1175 (e.g., fingerprint or other biometric data 1176). Again, if the security data fails, steps can be taken to deal with this, but validated security leads to creation of an electronic record of the visit 1179 and permitted entry into the environment at 1178 (which can include tracking, as described in more detail below, and confirmation of departure, if desired). If the visitor chooses the final option 440 of FIG. 4A, process 1200 of FIG. 12 is executed, beginning with presentation 1203 of scheduled visits near the current time from which the visitor may select at 1206 and supplement with additional information/inputs at 1209. Visitor input at 1212 is used to place a call via answering station 1215, 1218 or via telephone 1215, 1221 to the visited individual, who can then do one or more of the following: open a door 1224, create an electronic record of the visit 1227, print a visitor badge 1230, and/or provide instructions to the visitor 1233. As with the other options, live assistance or a security call can be placed 1236 if appropriate.

At the end of each interactive process' execution, the VMS 300 returns to its original state (e.g., providing a visitor with the options of FIG. 4A). As a safety mechanism, every transaction is subject to a time limit for implementation and execution. Upon expiration of a time limit, system 300 automatically abandons an uncompleted transaction and returns to its original state. This ensures that the system does not hang up or get stuck in a "resource waiting and error state." The system is configurable to collect operational and performance metrics that can be reported using management console 308, administrative software installed on any computing or a device such as a PC or notebook inside or outside the environment.

Data required for execution for options 420 and 440 of FIG. 4A can be collected and kept current (e.g., on an active directory and employee data server 360 of FIG. 3) by two methods—automatic extraction of data on a periodic basis from an active directory, lightweight directory access protocol or similar server that contains data about environment employees (e.g., names, phone numbers, alternate contact, email, etc. resources); and manual data entry that adds such data using the answering stations and/or console 308. The amount, type and limits of data that can be displayed for a visitor at station 301 are configured using console 308. Similarly, access codes required in option 430 are provided and stored at station 301 using console 308.

An answering station service can be implemented (e.g., installed on a computing and/or communication device connected to the VMS 300) both physically and/or logically, for example as shown at 310, 315, 320, 325 in FIG. 3. As a result of installation of this service, software all these devices and appliances now has the capability and capacity to respond to a live assistance call from a station 301 of FIG. 3. When a call is initiated by station 301, either by a visitor or a module such as 580 of FIG. 5, the call request is routed to the most appropriate available answering station that has the skills required to respond to that request, implementing a skills-based routing process or the like. In this way the network 311 prioritizes available answering stations to find the best-suited answering stations for the particular visitor data that has been collected. For example, if a notebook 310 running this service is operated by an environment employee who speaks Spanish, and operators of the other answering stations do not speak Spanish, then calls requesting assistance with a Spanish-speaking visitor will be routed to station 310 even though the other answering stations are also available. Such "skills-based routing" or evaluation of the resources and capabilities of individuals associated with the answering stations can be an integral component of the system and various ways of implementing such routing are well known to those skilled in the art. When an answering station service starts, it provides specifics to station 301, where that information is stored during the session when the answering station is still available as part of VMS 300. If an answering station shuts down, that answering station's presence and specifications are removed from the "SoftSwitch" at station 301. When the answering station rejoins VMS 300, the data is updated again.

Embodiments of the present invention also can maintain employee time records to assist with pay and benefits. Such tracking enables a VMS 300 to collect employees' time and attendance data, which periodically can be uploaded to a backend business communication server 395 (as shown in FIG. 3), eliminating the need for human staff to perform this function. The employee time/attendance embodiments contain the apparatus, configurations, devices, methods and processes disclosed above. Variations to the VMS embodiments allow for recording employees' work time and providing the data for utilization. A radio frequency identification (RFID) scanner, a barcode reader, or a smart card reader is attached to the VMS and a smart card or RFID or bar coded card/tag is used as part of credentials presented by employees for access and authorization (e.g., ID cards, common access cards (CACs), entry cards, etc.) that are authenticated and validated by VMS 300 as part of its identity management function in controlling physical access controls. Such RFID cards/tags are commercially available with printable surfaces to print employee data, bar codes, employee pictures, etc. (referred to as "employee identification data"). Each employee has only one associated RFID card/tag.

Figure 13:
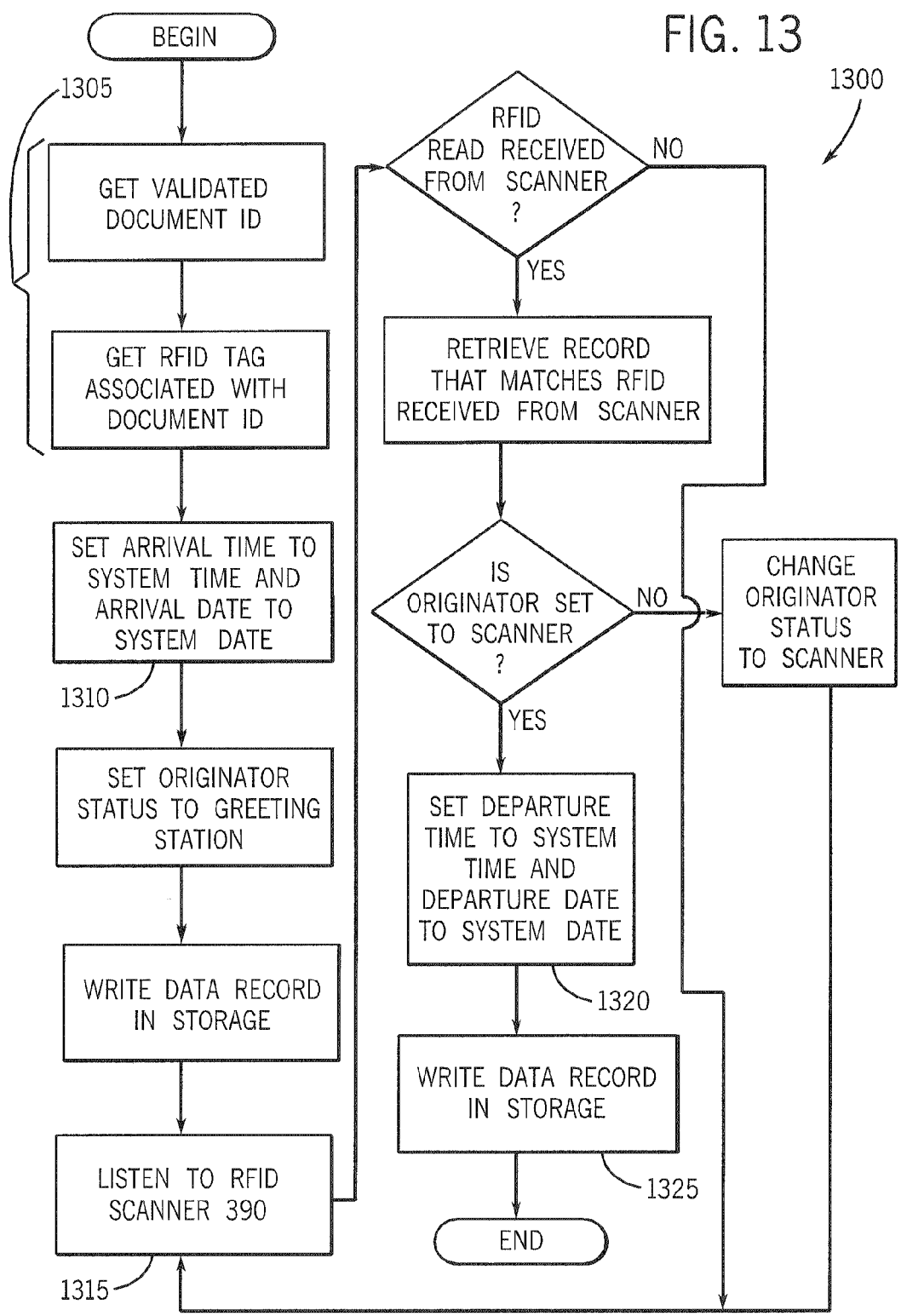
FIG. 13 shows a flow diagram of an exemplary creation and update of an employee's time/attendance record.

As seen in FIG. 3, short range RFID scanner 390 is installed adjacent to access point 375 and communicates with VMS 300. An RFID system typically includes a database, memory, etc. inside the environment that stores employee ID data so that date and time of each employee's entry and departure are validated/captured and provided to VMS 300. Departure time typically might not be recorded without an employee-implemented process such as designated exits equipped with RFID scanners, bar code or smart card readers because most conventional access points are only controlled for environment access, not departures. Backend business application time/attendance server 395 shown in FIG. 3 can be accessed by VMS 300 using network 311 connectivity. Station 301 periodically uploads employee time/attendance data to server 395, which can use or distribute the data to applications and processes used to calculate employee wages and benefits, etc. A process 1300 shown in FIG. 13 can be used to create and manage each employee's time and attendance record. The employee time/attendance process can be implemented as part of the process in FIG. 8. FIG. 13 shows the process flow, including getting identification data 1305, creating an entry time stamp 1310, monitoring the RFID scanner 390 at 1315, updating the record with departure data at 1320, and storing the complete time record at 1325. Processes and automated tasks like periodic examination of records with missing departure times, unmatched arrival times, reported extended stays (that is, visitor stays in the environment beyond normal expected visit hours), error reporting, periodic uploading of data to the business server, archiving of data, etc. are handled using conventional methods of programming and data validation, and are well known to those skilled in the art.

Figure 15:
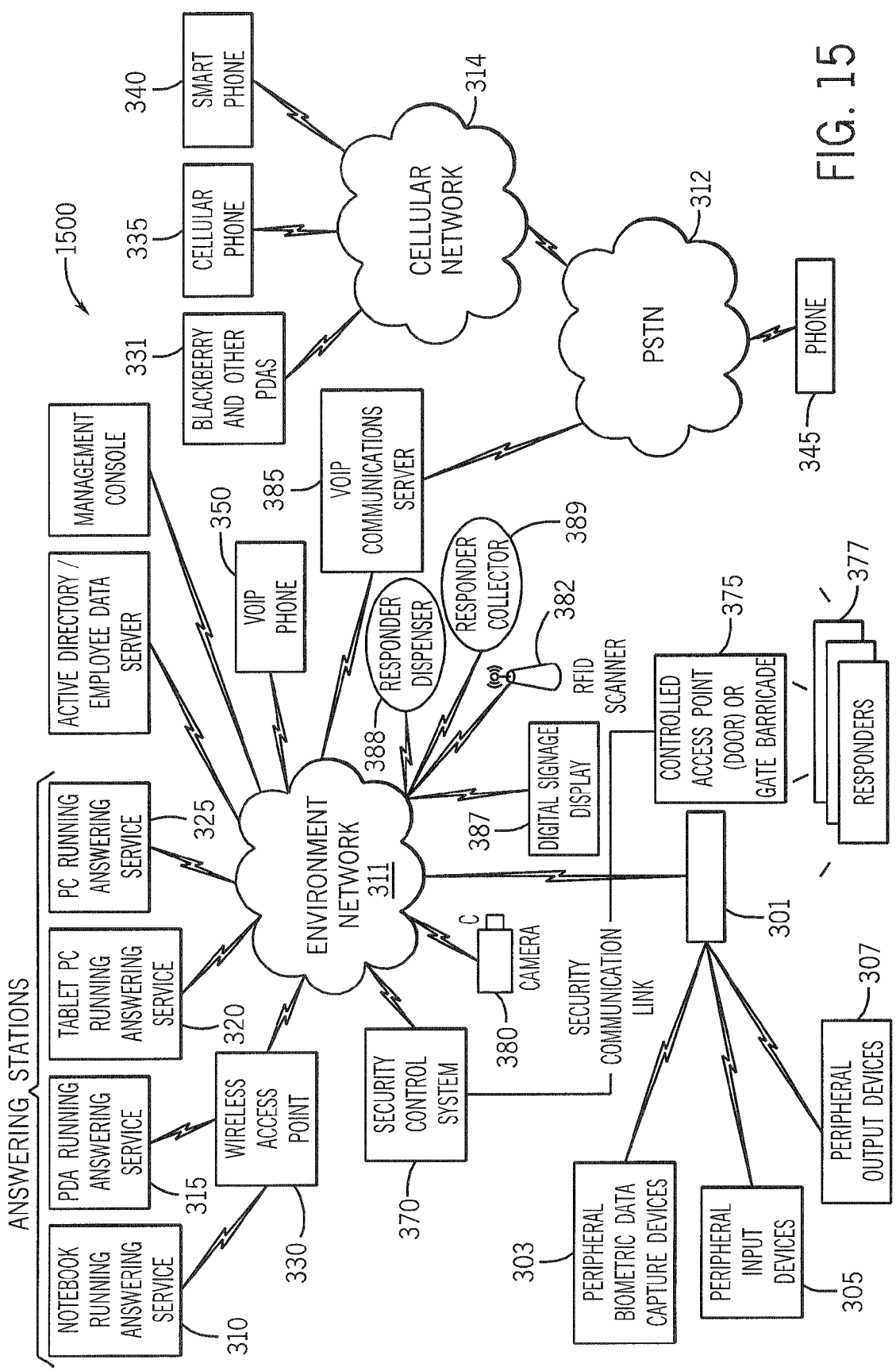
FIG. 15 shows an exemplary visitor and vehicles reception and/or monitoring system embodiment.

The VMS 300 above (also referred to as an "access control system") also can receive vehicles and control an access-controlled security system where vehicles and non-business assets are also subject to security validation and verification methods, for example using a modified menu of options such as the one shown in FIG. 14. FIG. 15 is an exemplary configuration of such a vehicle-enabled VMS 1500 and thus constitutes a visitor/vehicle management system 1500.

Vehicle entry in any environment (access-controlled or not) has an inherent issue of flow management associated with it, which refers to the methods for moving a vehicle inside an environment, follow directions, follow a path, park the vehicle in a location, etc. Static signage is used as a tool for flow management in current systems. This static signage, however, is expensive to install, manage and maintain, and cannot react to changing environmental situations.

When implementing security measures to permit vehicles into an access-controlled environment, an identifier (e.g., barcodes, stickers, transponders, descriptions in access lists, etc.) typically is issued and used for vehicles that are frequently brought into such an environment. Such an identifier (and any accompanying documentation) is issued after pre-processing/collecting vital data about the vehicle, operator and/or owner. Individuals use visual inspection and/or technology-assisted processes to assess vehicles entering an access-controlled environment. Examples include visually inspecting a sticker, scanning a bar code, transponder automated response to system requests, etc. The access eligibility status of an individual to a secured access-controlled environment (or any restricted domain like computers, networks, files, etc.) often is established using three factors: (1) something the individual knows, (2) something the individual has; and (3) confirming that the person in possession of (1) and (2) is the correct person.

The degree of security and sensitivity can dictate how many of the three factors must be confirmed to establish the identity of an individual for that process and/or transaction. For example, the following activities and corresponding identification confirmation techniques are used: (a) for writing a check, "Something you have" (for example, a driver's license or other acceptable identification) may be sufficient; (b) for traveling by air, two forms of the same type of identifications such as a boarding pass and a driver license might be required; and (c) for entering a military base, a common access card (CAC) as well as a biometric match of a fingerprint (that is, both "something you have" and "confirming you are the correct person") might be needed (for even more secure access control points, one may need also to know a pass code (adding "something you know"). Again, proving identity typically by a combination of factors is a function of the degree of security enforced at controlled access points.

Some access control system embodiments allow combinations these types of identifying factors before granting a visitor access to an access-controlled environment. The same types of measures are executed in a vehicle access control (VAC) system establishing vehicle identification. Classifications of "employees," "trusted visitors" and "occasional visitors" also apply to vehicles. Vehicles that belong to the access-controlled environment and gain access to that environment most frequently are viewed as having the same characteristics as employees. Similarly, vehicles that do not belong to that environment, but gain access to the environment regularly have the characteristics of "trusted visitors." Finally, vehicles that access the environment occasionally are viewed as "occasional visitors." An important aspect of embodiments of the VAC system is to establish that the vehicle seeking entry is "the correct vehicle." This is done by attaching a unique signature to each vehicle, similar to fingerprint, which is carried by one and only one vehicle. In some embodiments, a responder is paired to a given visitor, establishing an "visitor identity link" that can be used in tracking, monitoring and processing data concerning a visitor's visit to the access-controlled environment. Similarly, a responder can be paired to a vehicle to establish a "vehicle identity link" that can be used in similar fashion in tracking, monitoring and processing data concerning a given vehicle in the access-controlled environment. A VAC system includes essentially the same apparatus, methods, processes, etc. of a VMS or other access control system. Components, methods and processes are added to enable vehicle clearance and reception, flow management, and authentication, validation and verification of visitor and vehicle credentials for identity management, greeting, and facilitation. A VAC system 1500 is shown in block form in FIG. 15 and uses additional components when compared to the VMS 300 of FIG. 3.

At a given outer access point, one or more cameras 380 can be mounted where needed and connected to the network 311. A weigh scale (which can be part of a controlled access point 375) under the pavement before an access point gets a vehicle gross weight at that access point, helping to classify the vehicle type. Such scales are commercially available for similar purposes. One or more responders 377 (i.e., devices having unique identification signatures that either advertise the signature or respond to a request for identification; e.g., RFID cards/tags, barcodes, transponders, Bluetooth devices, infrared devices, radio devices, etc.) can be attached permanently or temporarily to a vehicle that will have a unique signature while the responder is associated with the vehicle. If the vehicle belongs to the environment (e.g., an "employee" status), then that vehicle's responder is permanently attached to the vehicle and can be matched to a vehicle weight, license number, etc. Security concerns about responders removed from authorized vehicles and being used on other vehicles are addressed by a validation and verification system.

A scanner 382 (RFID readers/scanners, radio receivers, Bluetooth devices, bar code readers, etc.) in FIG. 15 receives advertised or reply signals from responders 377. Two types of scanners are advantageous here, active scanners and passive scanners. Active scanners listen for and to any advertised information from responders, while passive scanners need to be activated to get responder data. Either type of scanner can be used in embodiments of a VAC system, depending on the particular system. Each responder 377 must function with at least one scanner 382. A responder dispenser 388, located in the environment or on its periphery as depicted in FIG. 15, physically dispenses visiting vehicle responders 377 (when authorized by the system to do so) and can be a metallic sleeve in which responders 377 are loaded. A spring in the top/lid of dispenser 388 pushes responders 377 down for dispensing to vehicles. A slot at the bottom is normally closed and electronic circuitry controls sliding the slot open, dispensing one responder at a time, and providing the signature of the responder to the VAC system, which can then associate identification signature data with visitor data and/or vehicle data for the visitor/vehicle to which the responder was dispensed (or assigned). Dispenser 388 can connect to VAC network 311. A responder collector 389 collects temporarily issued responders from visitor vehicles as they exit the system 1500. Collector 389 can read the signature of a responder 377 dropped in the collector 389 and inform VAC system 1500 that the responder was collected and the visiting vehicle allowed to leave the environment. Like dispensers 388, collectors 389 can be located in the environment or on its periphery, and physically receive responders when deposited by departing visitors and/or vehicle operators. Electronic circuitry used to read collected responder data also has a network interface that allows dispenser 389 to network with the VAC system 1500. Digital signage displays 387 in FIG. 15 provide visual and/or audio directions to visitors and assist with vehicle flow management. The digital signs 387 can be installed at each access control point 375, at selected locations inside the environment, and can be updated automatically by VAC system 1500, by authorized personnel overseeing system 1500, and also can provide emergency or other notifications to vehicle operators or a specific vehicle operator.

Figure 16:
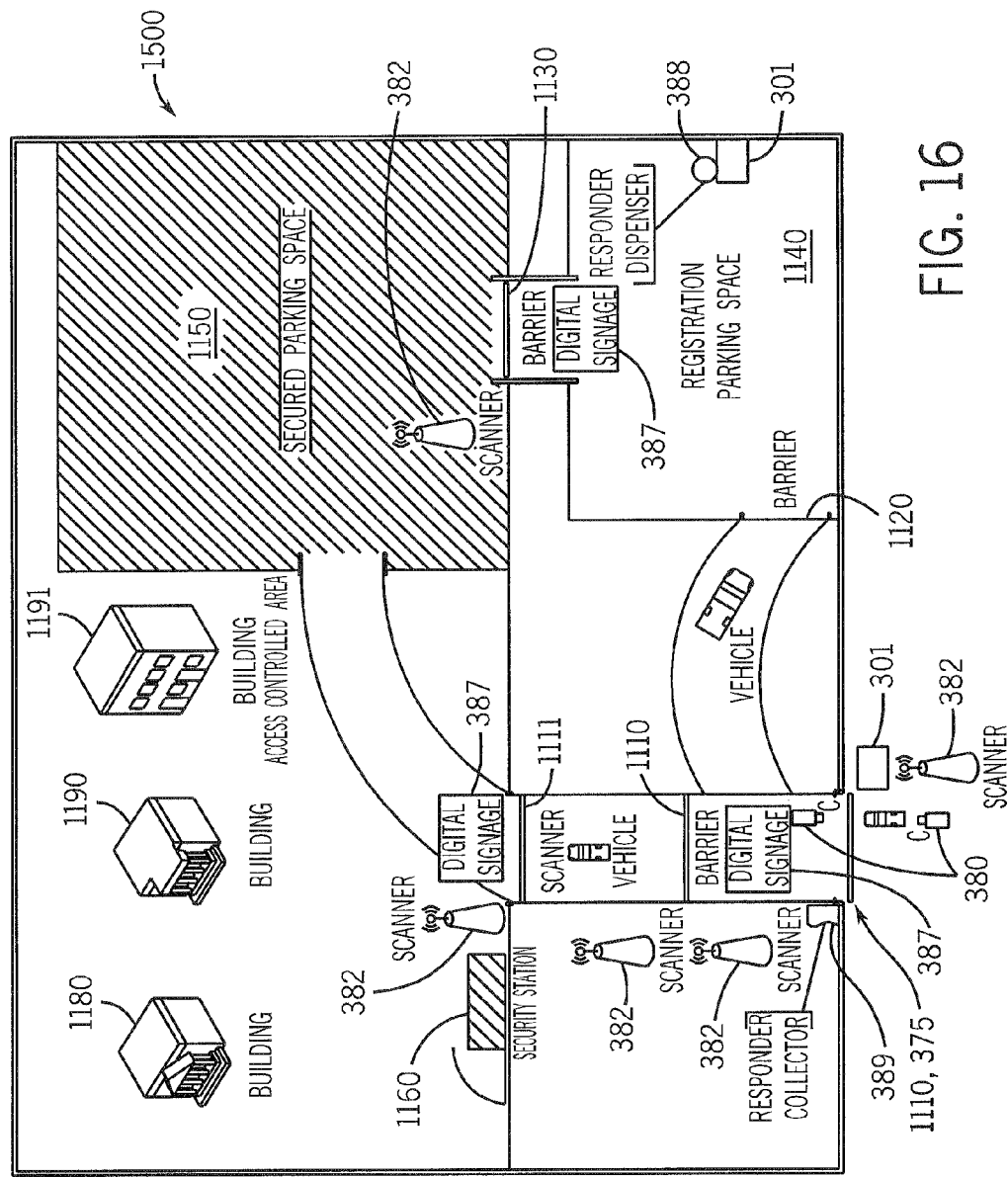
FIG. 16 shows exemplary system and method embodiments for receiving visitors and vehicles in an access-controlled environment.

FIG. 16 shows a physical implementation of VAC system 1500 for visitor and vehicle reception and monitoring in an environment. Environment buildings 1180, 1190 and 1191, registration parking area 1140, and secured parking space 1150 are access-controlled facilities. An outermost, first barrier 1110 (an outer access point 375) is a perimeter barrier that controls access to the environment generally. Access to points inside the environment perimeter is controlled using barriers 1110, 1111, 1120, 1130 at one or more access points. Once a vehicle enters the environment, barrier 1110 directs occasional visitors (and possibly trusted visitors) away from the access point to the buildings, directing such visitor traffic to the registration area 1140 via barrier 1120. Barrier 1120 controls access to registration area 1140, which can have a lower access control level. Access to the secured parking area 1150 is controlled by access point barriers 1111, 1130 and vehicles admitted to area 1150 via barrier 1130 are prohibited from entering the building area that is accessible via barrier 1111. In the embodiment(s) shown in FIG. 16, all access points are controlled by central a security station 1160. Vehicles in FIG. 16 are for illustration to demonstrate one or more embodiments of the access control system.

In FIG. 16 a greeting station 301 and scanner 382 are placed at the outermost environment boundary entry points and can be used for registering visitors and vehicles, if either or both need to be registered before granting access. Important decisions are usually made at this point (e.g., whether or not to allow or refuse access; if allowed, evaluating limits to impose for areas of the environment). Cameras 380 also are placed at the first entry point. The placements shown in FIG. 16 are for illustration purpose only and other considerations will be apparent to those skilled in the art. The barriers shown in FIG. 16 do not need to be installed in the same configuration. For example, when barriers 1110 and 1111 are placed in this fashion, the access control system will not send a request to open inner barrier 1111 unless and until outer barrier 1110 is closed, providing added security and control by allowing one or very few vehicles to enter the environment in a controlled fashion and to isolate any vehicle that tries to enter the controlled environment without proper identification.

If a vehicle passes the initial access point barrier and is determined to be authorized for access to the building area (for example, via scanners 382 adjacent to one or more barriers), then digital signage 387 can be immediately configured to provide instruction/direction to the appropriate barrier and/or parking area. Speed, as well as accessibility, can be controlled using the barriers. As noted above, greeting station 301 is located at the initial access point. Another greeting station 301 can be placed in the registration area 1140 to assist visitors (e.g., trusted and/or occasional visitors). The second greeting station 301 in area 1140 also can be used to make sure that a non-employee who entered using greeting station 301 outside the access-controlled environment has "checked in" in a timely manner. Moreover, additional cameras 380 can be used in the registration and other areas to track and record visitor movements. These cameras might include audio recording, too. To accommodate visitors who do not have pre-issued responders, a responder dispenser 388 is placed adjacent greeting station 301 in area 1140. Temporarily issued responders can be returned at the conclusion of a visit by placing the responder in a responder collector 389 at the exit/access point of the outer perimeter of the access-controlled environment. Other uses and configurations of the components discussed and disclosed herein will be apparent to those skilled in the art.

Figure 17:
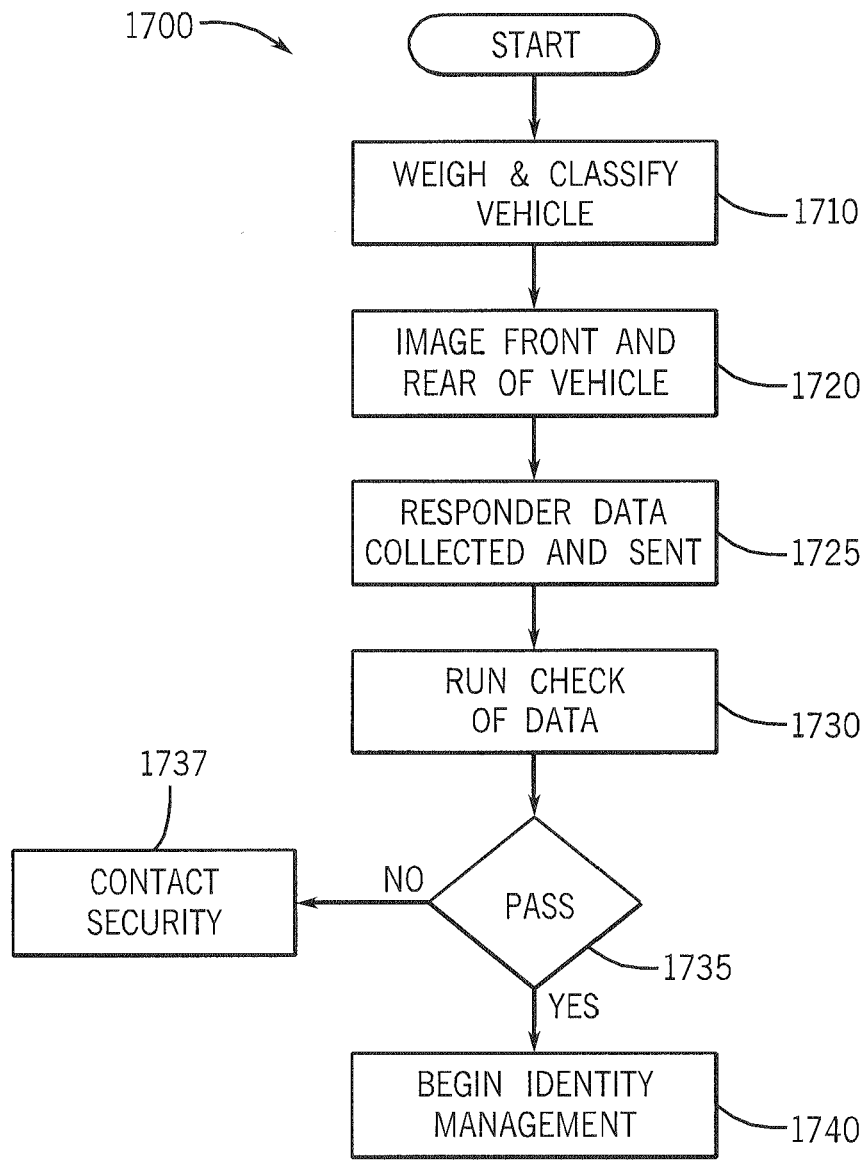
FIG. 17 is a flow diagram of an exemplary process for initial screening of a vehicle at an access-controlled environment entry point.

Operation of the system of FIG. 16 includes two processes—one for entering the environment, the other for leaving. When a visitor in a vehicle arrives at the outmost entry point of the environment, they encounter perimeter barrier 1110. At this point, visitor and/or vehicle status can be classified. In either case, process 1700 of FIG. 17. A scale transmits gross vehicle weight data at 1710 to the access control system (e.g., via a network connection shown in FIG. 15), which gives the vehicle classification (e.g., car, truck, etc.). At 1720 cameras 380 image the front and the rear of the vehicles (or any vehicle parts that assist in identifying the vehicle and/or its operator), reading the license plate(s), and sends this data. If the vehicle has a responder, the scanner at the access point reads the identification signature at 1725 and forwards that data to the access control system. At 1730 the access control system runs a "data check" that can verify that the front and the rear license plates match; determine the type of vehicle using a weight-type classification table and any other available data pertaining to vehicle type; verify that any detected identification signature is associated with the license plate and/or type of vehicle (if no identification signature is attached to the vehicle, the access control system then classifies the vehicle as an "occasional visitor" and permits entry subject to further actions such as vehicle registration); and checks to ensure that any vehicle identification signature, license plate and/or the vehicle type are not on a watch list for refusing entry to the environment.

If the system does not validate all parameters at 1735, and evaluates the information as a potential security threat, then a live assistance call is initiated by the external greeting station 301 to an available answering station, with notification of the problem (e.g., license plates do not match, mismatched identification signature and vehicle type, etc.). The answering station operator can conduct further inquiry and/or can instruct the operator of the vehicle seeking entrance on the next steps, for example exiting the vehicle, waiting for security personnel to arrive, turning around and leaving, etc. If the access control system validates all parameters at 1735, the system can now begin identity management at 1740 of the operator and occupants. Once determined to have an acceptable visitor status, the vehicle operator is informed by the access control system of the vehicle's status using a greeting station display, visual display and/or audio loop. A modified version of greeting station menu options of FIG. 4B is presented to the operator after the vehicle's status is determined. Only two options are offered at this first greeting station to determine the status of the operator. If the operator selects the "Employee" option, then employee processing of FIG. 8 can be executed. If the operator selects the "Visitor" option, then the visitor is advised to drive the vehicle to the registration area 1140 in FIG. 16. Shunting visitor traffic from the initial access point facilitates and manages traffic flow.

At this stage, vehicle and operator status have been established and this is used for the flow management inside the controlled environment. Information can be conveyed to the operator using digital displays 387. If the vehicle has a valid identification signature (making it eligible to access the controlled environment) and the operator is determined to be an eligible employee to access the controlled environment, then a digital display 387 as shown in FIG. 18 will show a message such as "Proceed Straight" along with the license plate or other vehicle identifying information. If less than all required criteria are met (e.g., "employee" or vehicle status verified, but not both), then the operator might be asked to move the vehicle to the registration area 1140 for registration of the vehicle and/or the operator. In such a situation, the access control system can display a message on digital display 387 in FIG. 19 instructing the operator (via license plate and/or other vehicle identification information) to drive the vehicle to the registration area.

When a vehicle is sensed at barrier 1120 in FIG. 16, the barrier is lifted to allow access to area 1140 where vehicle and/or operator registration can be performed to acquire credentials needed to enter a desired area. Registration is performed at the registration area greeting station 301 placed in area 1140. Possible menu options available at this greeting station are shown in FIG. 14. If the visitor selects option 1410 for vehicle registration, the access control system provides interactive directions and instructions to collect vehicle and operator data. When the system is successful in acquiring vehicle data, validating acquired data, and establishing eligibility of the vehicle to enter the environment, a responder is dispensed and the responder's identification signature is added to the system for associating it with the particular visitor's vehicle information. All scanners within the environment then can read the signature of the visitor's responder and pass it on to the system for validation. The system validates the identification signature and performs actions like sending requests to the security control system 370 for raising the barriers, opening doors, etc. If both the vehicle and the operator need to be registered, and if the vehicle was cleared but the operator was not, then the responder is not dispensed and the vehicle has to exit the registration parking space, unless some eligible operator is associated with the vehicle, in which case the vehicle will be allowed to enter the environment with the eligible driver and will be tracked and treated accordingly.

Figure 20:
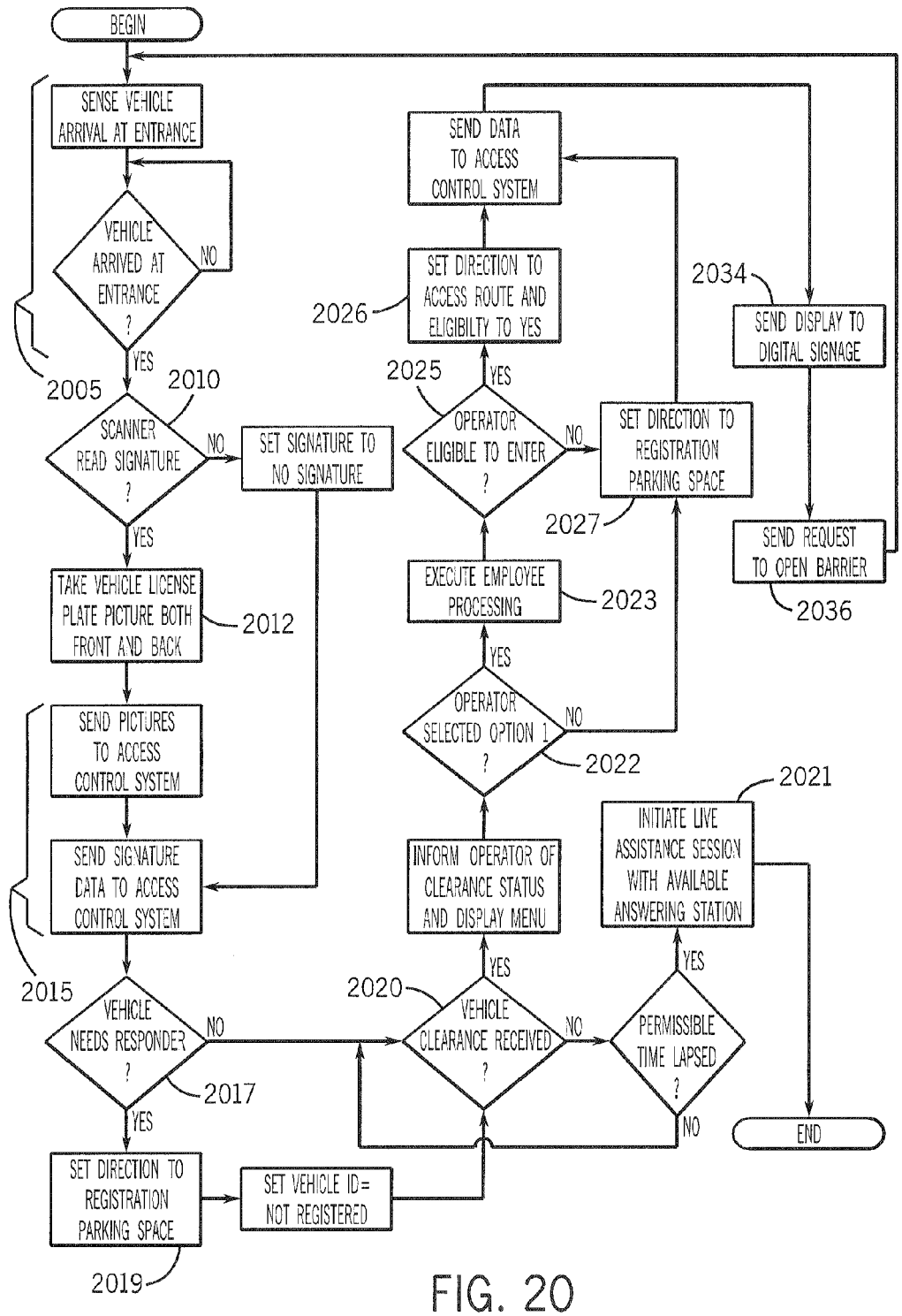
FIG. 20 is a flow diagram showing an exemplary process embodiment for receiving arriving vehicles at an access-controlled environment.

One embodiment of a process 2000 for interaction with a visitor vehicle is shown in FIG. 20. A vehicle is sensed 2005 at the entry point and a scanner 382 attempts to read an identification signature at 2010. When a signature is detected, photos are taken at 2012 and sent to the access control system along with the signature data at 2015. If no signature is detected, the system is so notified at 2015. A decision 2017 is made regarding the need for a responder so that a vehicle needing a responder can be directed at 2019 to a registration location like area 1140 of FIG. 16. A clearance check is performed at 2020 (a failed clearance check is referred to live assistance at 2021). A cleared vehicle/visitor is presented with the FIG. 4B options at 2022, allowing employee processing at 2023 prior to a decision 2025 to admit the employee to the environment area 2026. In situations where the "visitor" option is chosen or where an employee is not eligible to enter a given area, the visitor/vehicle is advised 2027 to move to the registration area (again, perhaps area 1140). Data is sent to the access control system at 2030 to update the system's records and appropriate signage is displayed 2034 to assist the vehicle and open a barrier 2036. For options 1420, 1430, 1440, 1450 of FIG. 14, processes such as those shown in FIGS. 9, 10, 11, 12, respectively, can be employed.

Figure 21:
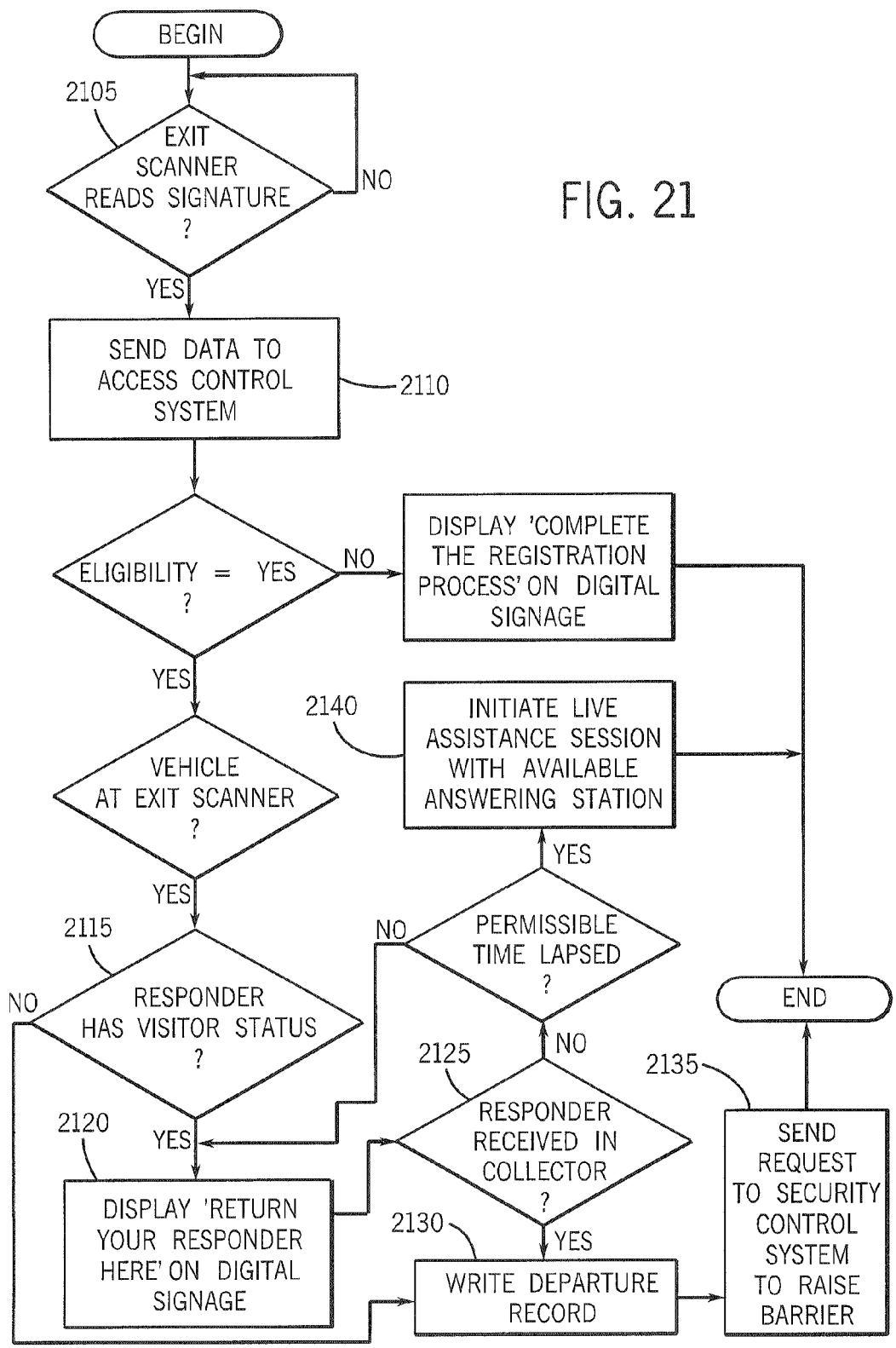
FIG. 21 is a flow diagram showing an exemplary process embodiment for vehicles departing an access-controlled environment.

When a vehicle and operator entered an access-controlled environment using an embodiment of the present invention, both vehicle and person had or were given unique identification signatures. For those that entered using a registration process, the identification signatures (e.g., badges, responders, etc. assigned temporarily) are collected at departure, for example using the process 2100 of FIG. 21. The exit scanners 382 at each barrier and/or access point read responder signatures at 2105 and pass that data to the access control system at 2110 for processing and requesting a security control system to remove the relevant barriers to permit egress. Responders permanently assigned to a vehicle are not collected. As a scanner 382 reads a visitor's responder signature at 2115 at the last exit, the access control system displays a message at 2120 on a digital display to return the responder to a collector. Once a responder 377 is received by collector 389 at 2125, the collector notifies the control system at 2130 of the responder signature that is returned. Upon receipt of such information, the system will ask the security control system at 2135 to remove the last barrier so that the vehicle can exit the environment. Failure of proper execution of this departure process can prompt a live assistance call at 2140.

Embodiments of the access control system according to the present invention significantly reduce the number of staff required to operate controlled access points, resulting in significant operational cost savings. Another benefit of these embodiments is that they reduce staff's exposure to potential security vulnerabilities and risks, especially before a visitor and/or vehicle has entered the controlled environment. Also, the access control system keeps an electronic log that can be used for forensic analysis and/or data supply to other devices, components and applications, thus reducing redundancy in such efforts.

Some embodiments of the access control system actively monitor and report the location and presence of all visitors (including employees in some cases) and vehicles inside an access-controlled environment. Once visitors and vehicles have entered a controlled environment, especially those imposing high security levels (e.g., military bases), active monitoring of the visitors and the vehicles inside the environment is desirable or even required. Prior systems monitored using security cameras, physical escorts and global positioning systems (GPS). In most situations, the movement of visitors and vehicles in such environments required a physical escort to ensure that visitors and vehicles traveled on a permissible route. These earlier systems had many inherent problems, such as requiring additional staff for escorts, staffing security centers using security cameras to monitor movement and location, etc. One common shortcoming of GPS monitoring is that the signals are usually not available inside a covered building and also can be affected by weather conditions. Therefore such systems were not very useful in monitoring visitors because most facilities are brick and mortar and not under open skies. The inherent problem with security camera monitoring is that it is very difficult to cover every corner of a building with security cameras; there are always areas with no coverage. Also, because security camera-based monitoring is based on images of a given visitor, it is difficult to identify visitors among people whose images are captured using cameras. For example, a visitor in a uniform mixes well in an environment with other uniformed individuals. Those monitoring the environment with security cameras may not be able to identify the visitor. Therefore, there is a need for a system that can actively and unobtrusively monitor each visitor and/or vehicle inside a controlled environment.

Figure 22:
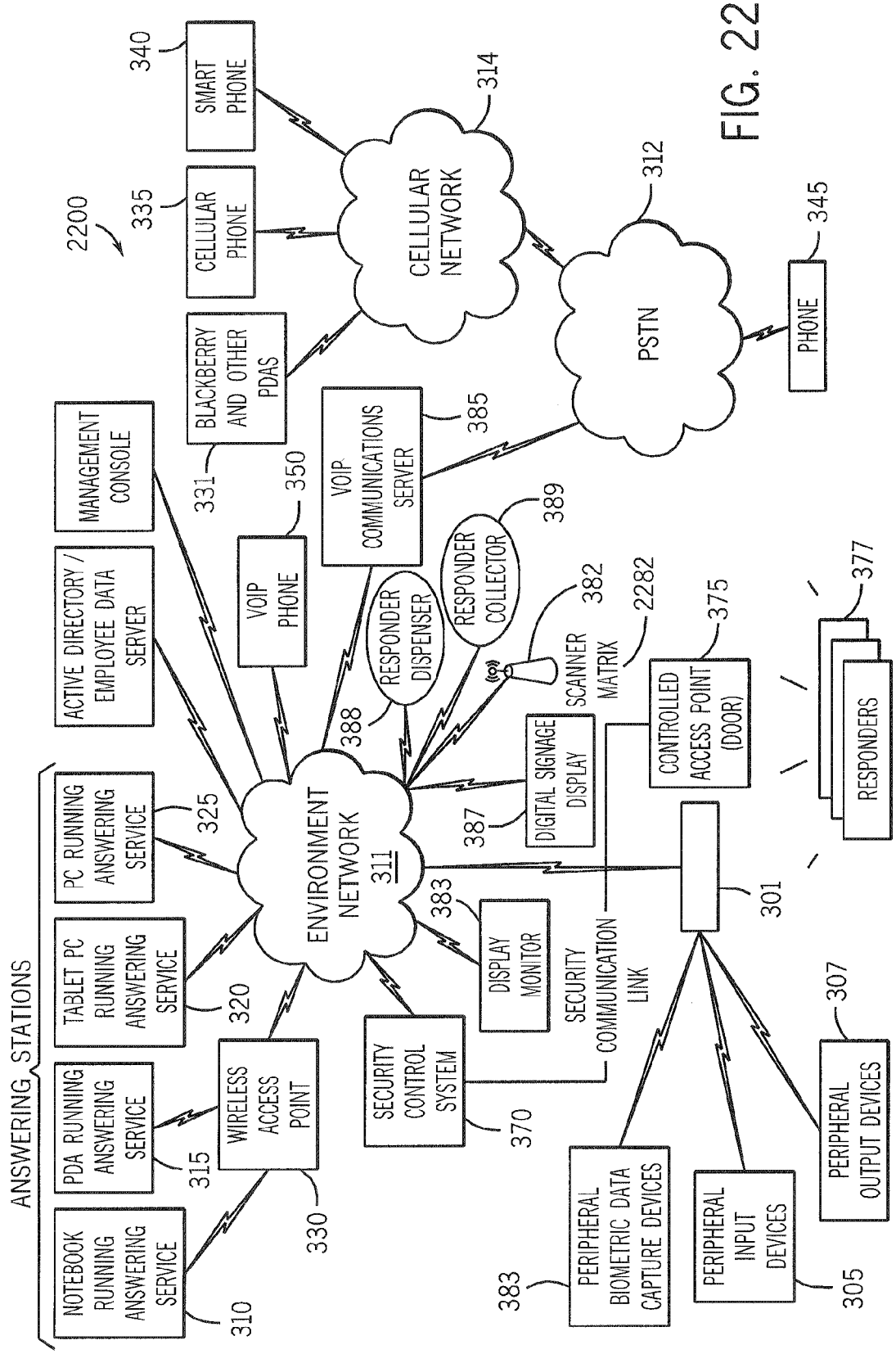
FIG. 22 shows an exemplary visitor/vehicle monitoring system embodiment with active monitoring of visitors and/or vehicles in an access-controlled environment.

One or more embodiments of a visitor monitoring (VMon) system 2200 are shown in FIG. 22, which augments earlier systems 300 and 1500, discussed in connection with FIGS. 3 and 15 above, respectively. In system 2200 scanners 382 are implemented in the access-controlled environment to form a scanning device matrix 2282. Using responders 377 (e.g., RFID cards/tags, Bluetooth devices, infrared devices, etc.) in or for specially designed visitor badges and vehicle identifiers which will have a closed circuit loop which will send alarms to a monitoring location when detached after the first installation, each visitor and vehicle is tracked and actively monitored. Similar to embodiments where employees' credentials are produced on responders, visitor badges are produced on such responders. In FIG. 22 uses responders in a manner analogous to that discussed above; vehicles carrying a responder will have a unique signature while the responder is (permanently or temporarily) associated with the vehicle. Security concerns about responders being removed from authorized vehicles and being placed on unauthorized vehicles are addressed in a validation and verification system. Responders 377 can be dispensed and collected using equipment 388, 389 discussed above. Scanners 382 are also the same type used in systems and methods discussed above. Digital signage displays 387 in FIG. 22 can be used inside buildings and in other locations to direct and assist pedestrian and vehicular traffic, including visitors carrying badges or other credentials that include responders that have identification signatures. A display monitor 383 in FIG. 22 is used to show tracking and monitoring. This display can be provided a graphic representation via computer, television or other monitor device (e.g., similar to a radar or air traffic control depiction).

Figure 24:
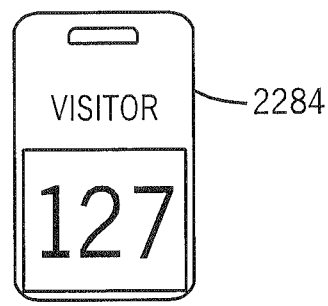
FIG. 24 shows an exemplary visitor badge produced on or with an integrated responder (RFID card in this example).
Figure 25:
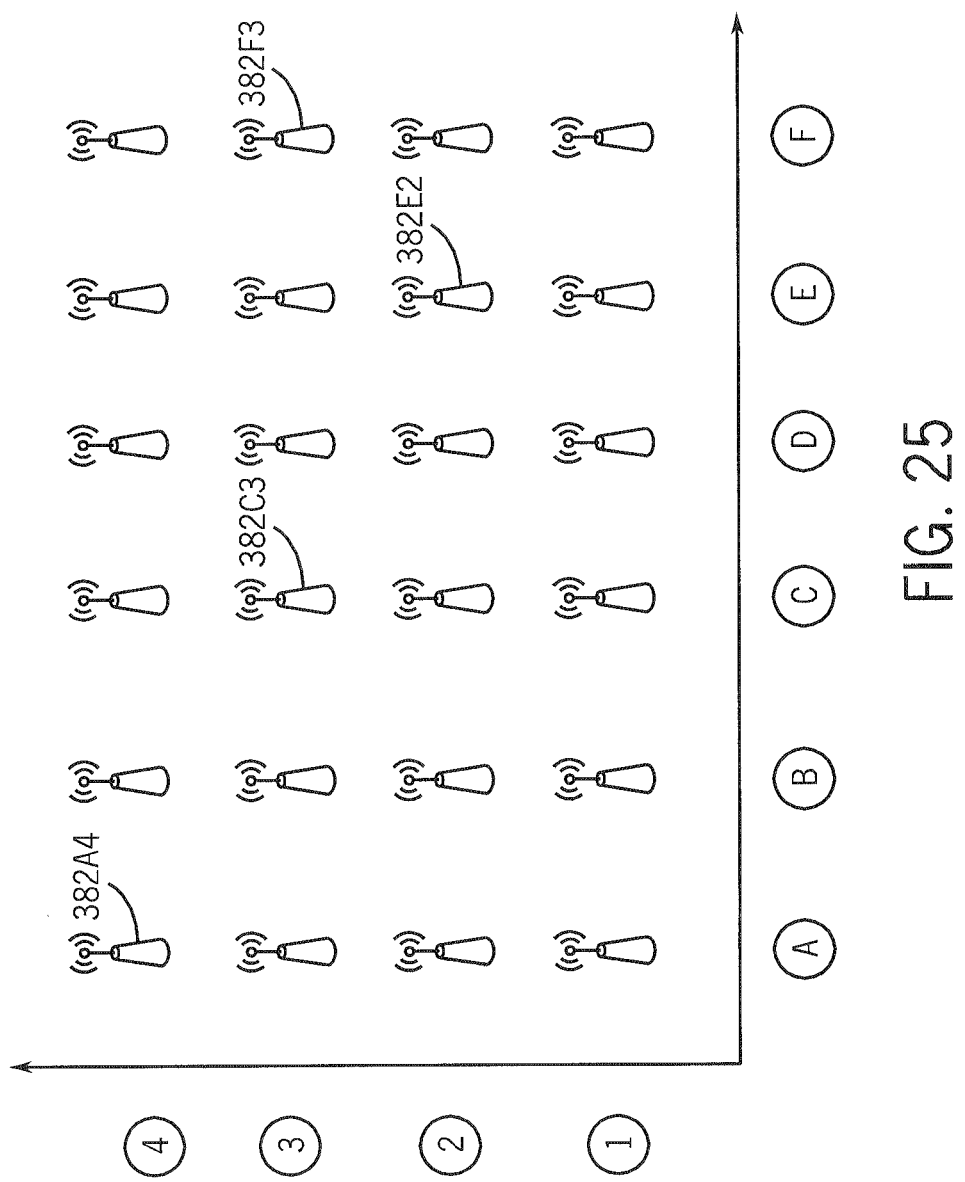
FIG. 25 shows an exemplary scanner configuration, for example as a matrix.

An exemplary visitor badge 2284 of FIG. 24 is produced with an integrated responder (e.g., an RFID card/tag forming the number "127"), is used to associate a visitor with an identification signature and is both a machine and a human detectable identifier. When a scanner 382 reads a responder signature, scanner 382 sends the identification signature data to the VMon system where the signature is mapped to user/visitor "127" to whom the badge was issued. In such an embodiment the visitor badge might be worn by a visitor or be in a vehicle (e.g., in a window so that the visitor badge acts as both an electronic identifier as well as a visual identifier, just as it would on a visitor badge worn on a lapel or the like). In FIG. 25 a matrix 2284 of scanners 382 is arrayed in rows and columns. The scanners 382 occupy X-Y coordinates in matrix 2284, thus providing a way to locate each unique identification signature by mapping it to a matrix scanner. The matrix 2284 is configured so that a responder badge placed anywhere in the matrix will be read by 1-4 scanners. An area between 4 scanners can be referred to as a cell.

Figure 26:
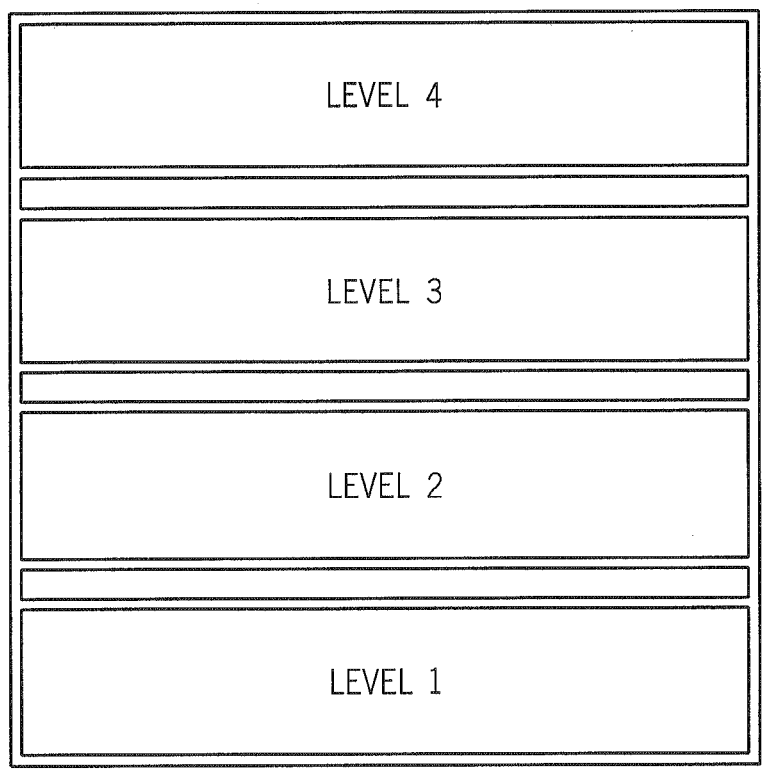
FIG. 26 shows an exemplary multi-level access-controlled environment usable with a scanner array or matrix embodiment.

As a visitor with badge moves around this matrix, the responder identification signature is read by one or more scanners 382, which transmit position data to the VMon system 2200. Based on scanner location and time of the data collection, collected tracking data (i.e., both positional data and associated temporal data) corresponding to the responder is mapped to a cell (e.g., using a timestamp). Responder movement causes new scanners in a given scanner matrix to read the responder signature and to send responder signature data to the VMon system, which generates updated tracking data (also referred to as "visitor/vehicle movement data"), maps the responder to its assigned visitor and/or vehicle and plots the responder's location on a map or other graphical display of the environment. In a multi-story building scenario, each building level has a similar scanner matrix on each floor and a third dimension referencing floor level is added to the matrix addressing scheme, which improves tracking/monitoring capabilities further. An exemplary configuration of a third dimension is shown in FIG. 26. Using the level reference as the third dimension, the address of scanner 382C3 in FIG. 25 is 1C3 if the visitor is on level 1, and 3C3 if on level 3. For vehicles, scanners can be set at regular intervals along roadways and other paths that are large enough for vehicular use. Again, mapping of vehicle progression through the environment and any deviations from appropriate routes, etc. can be collected and evaluated, providing data to security and other systems, and allowing digital signs 387, etc. to warn the vehicle operator of such deviations.

In a system such as the one shown in FIG. 22, a responder dispenser 388 is placed in the same room with a greeting station 301. Dispenser 388 is configured as part of system 2200 by connecting it to network 311 and issues a responder (e.g., card 2284 in FIG. 24) upon authorization from the VMon system 2200 (which acquires the responder identification signature). Thereafter, before the responder is returned, the identification signature is associated with a label (e.g., "127" in FIG. 24) and system 2200 tracks the label and the visitor or vehicle to which the card was dispensed. Scanner matrix 2284 are connected to network 311, as is display 383, in a visitor/vehicle tracking location. Multiple displays 383 can be configured and added to system 2200. One or more dispenser collectors 389 in FIG. 22 are placed at the last controlled environment access point(s)/exit(s) for reclaiming responders at the end of a visit. At least one digital signage display can be located inside the environment at the last exit.

In an exemplary process 2700 of FIG. 27, a visitor or a vehicle arrives at a greeting station 301 (e.g., at an outer access point) and is granted access to the environment at 2705. The visitor/vehicle can be provided at 2710 with one or more responders 377 from a dispenser 388, which sends dispensed responder signatures at 2715 to the VMon system 2200. System 2200 then associates the label and identification signature with the visitor/vehicle to which it was dispensed at 2720, thereby "activating" the monitoring of that visitor/vehicle by creating an arrival record at 2725. Each visitor is instructed to keep the responder with him/her during his/her entire presence in the environment. Responders can be configured to alert the system 2200 of any removal of the responder from a vehicle and/or visitor's person, for example by the breaking of a magnetic loop or circuit that would be triggered by detachment of a responder from its intended location. As the visitor/vehicle enters the VMon system 2200, scanners 382 (e.g., scanner matrices 2284) start reading and tracking the responder signature at 2727, sending any collected tracking data to the VMon system, where the system maps the visitor/vehicle location over time at 2730, for example by timestamping data to allow reconstruction of a visitor's movement within the access-controlled environment. Vehicle movement can likewise be reconstructed using the tracking (position) data and any accompanying timestamped data. Whenever a visitor does not provide required action or data, or removes or tampers with a responder, for example, an alarm can be generated at 2799 by display 383.

At the end of a visit, when the visitor/vehicle is detected at an outer access point at 2735, the visitor/vehicle operator deposits the responder in a collector 389. Once the responder is returned to and read by collector 389 at 2740, it sends the responder signature to the system where the system finds the associated label and links it to the visitor and a departure record at 2745. Subsequently, the VMon system releases the responder identification signature (and thus the responder) and shows it as "available." The visitor monitoring system then instructs the security management system at 2750 to unlock the door or to raise the barrier at the exit/access point, creating a departure log of the visitor/vehicle. The visitor/vehicle exits the controlled environment upon completion of visit.

Figure 28:
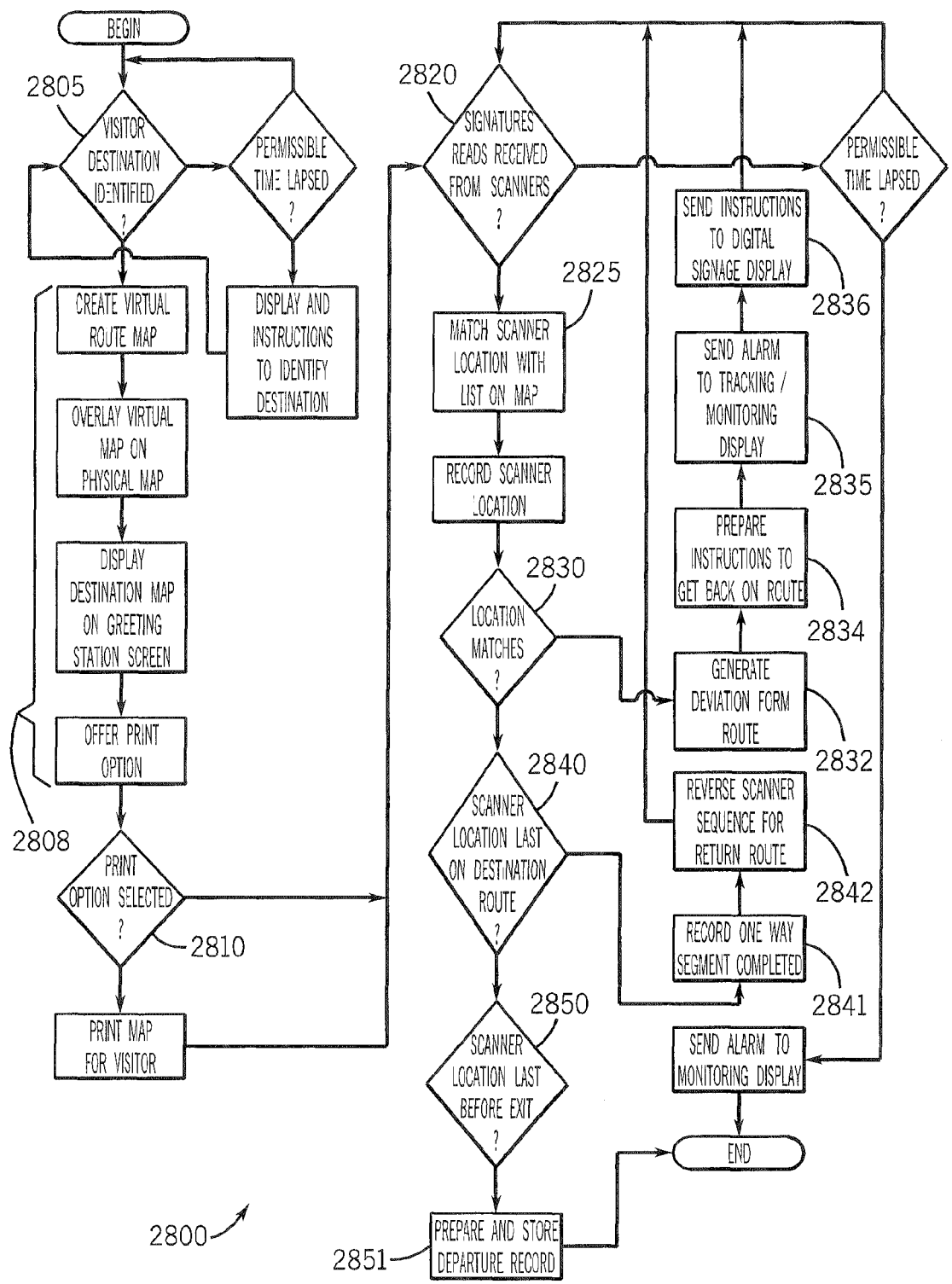
FIG. 28 is a flow diagram of an exemplary process embodiment for wayfinding for visitors and/or vehicles inside an access-controlled environment.

The VMon system 2200 also can be used for wayfinding, providing visitor/vehicle guidance in a controlled environment, and facilitating an unescorted visit. One embodiment of a process 2800 for wayfinding operation is shown in FIG. 28. When the visitor identifies a destination at 2805 inside the controlled environment during the registration process directly or indirectly (e.g., by contacting an employee inside the environment or when such identification is made by an answering station operator), an actual or virtual map from the greeting station to the destination is developed at 2808 by the VMon system. This map can plot and involve all of the scanners and/or scanning cells in the path from the visitor's current location to the destination, identifying those scanners as "valid" scanners. The virtual map can be converted to pictures, maps and/or text directions by the system and be displayed on a station 301 display screen. The visitor then is given an option at 2810 to print the map to take along from the current location to the destination. If such a map is presented to the visitor, the VMon system assigns a map number to the visitor's route that is associated with valid scanners along the route and the visitor's responder signature. When the visitor moves inside the environment, scanners read the responder's signature at 2820 and transmit the identification signature information to the system. The system monitors the valid scanners along the plotted path at 2825 and, as long as the scanners match the path list to the destination at 2830, the system assumes the visitor/vehicle is on the correct path. If a scanner response is received that is not included in the path list, the system calculates at 2832 the deviation of the "off-path" reporting scanner from the closest "valid" scanner provided to the visitor. The system then develops corrective instructions at 2834 to get the visitor back on the correct route. This information is sent to the first digital signage display at 2836 that the visitor is likely to encounter. Simultaneously, a security alert is sent at 2835 to the visitor movement display 383. Process 2800 can detect when the last valid scanner on the route is reached at 2840, then reverse the route and scanner sequence to generate a "return route" at 2842 after recording completion of the one-way segment at 2841. On the return trip to exit the environment, the same valid scanner path-tracking is used until the last scanner at the exit is detected at 2850, at which time a departure record is generated at 2851.

The VMon system 2200 can operate with distributed processing when multiple greeting stations 301 are installed in system 200. For example, the system can divide tasks among different greeting stations 301, with processed results sent to a central managing greeting station, console 308, or some other device that interfaces with the other system devices such as monitoring displays, digital signage displays, etc. For example, a first greeting station can receive responses from scanners 382 and record movement for a given visitor. If a particular type of exception or event occurs, that first greeting station might pass off responsibility for that visitor to a second greeting station, which in turn passes responsibility for tracking the visitor to a third greeting station if another type of exception or event occurs. The second and third greeting stations can submit their processed information to a fourth greeting station that is configured to function as the managing greeting station. This managing device will send all alarms, notifications, etc. to monitoring displays, digital signage, etc., as well as notifying security personnel if there is a need for human intervention in the visitor's behavior.

Embodiments of the visitor monitoring system significantly reduce the staff required to operate access points, track and actively monitor a visitor/vehicle inside a controlled environment, and provide a virtual escort in such environments, thus resulting in significant operational cost savings. The VMon system also enables monitoring and tracking of visitors and vehicles in all areas of the access-controlled environment, which may not be technically possible using conventional monitoring and tracking tools and techniques. Visitor monitoring systems according to one or more embodiments of the present invention also reduce dangers to the environment and staff posed by potential security vulnerabilities and risks. In addition, the system keeps electronic visitor and vehicle arrival, movement, and departure logs that may be used for forensic analysis and/or providing captured data to other devices, components, and applications, thus reducing redundant efforts and delivering cost savings.

Other embodiments of the VMS can be adapted for using the embodiments and examples shown in the Figures pertaining to the VMS and others. For example, the United States State Department has the responsibility for providing consular services to both U.S. citizens and visa services to non-U.S. citizens. The visas to enter the United States for non-U.S. citizens are issued after establishing eligibility of the applicants, estimating security risks, and delivering consular services. Because of the heightened security environment, delivering consular services now involves keeping applicants at a safe distance from consular and embassy buildings. Some or all of these objectives and tasks can be accomplished using embodiments of the visitor management system and/or a modified remote medical consulting system. Such a consular services system can identify individuals seeking consular services, verify that they are eligible to receive such benefits, and eliminate undesired individuals from accessing embassy and/or consulate buildings while mitigating the security vulnerabilities and threats. Such embodiments enable the person seeking service to fill out electronic forms, pay required fees using cash, credit or debit methods, inquire about the status of a case already being processed, research a topic of interest in a related field from internal and external resources, and such operations that are normally performed in a face to face consular service delivery session. Moreover, such services can be provided to individuals in locations that are remote relative to the physical locations of an embassy and any associated offices. For example, a French citizen might be traveling the United States and require assistance from either the United States State Department or the French Embassy in the United States. Rather than having to travel to such an agency's physical location, and rather than being limited to the restricted assistance that can be provided by telephone or online, one or more embodiments of a consular services system could provide enhanced interactive assistance to the French traveler. Such embodiments use the same basic processes involving skilled-based routing for connecting the consular services seekers and the most competent individuals at the designated providers. The VMS, when connected with an electronic signature capture device, biometric identification device, and machine readable passport reading device, is embodied in traveler assistance stations (TAS), which can be implemented as station 110 of FIG. 1, for example, using the proximity detection system like that discussed in connection with greeting station 301, above, and various input devices, including a passport reading device and analogous user option selection devices.

TAS can help citizens to obtain consular services such as reporting birth of a child, reporting a lost passport, sending emergency messages to families in a home country, requesting new or replacement passports, etc., by obtaining required information and digitally filling out applications, paying fees and scheduling appointments with the closest embassy or consulate location. Also, TAS can print maps, provide directions, print government or non-government forms (such as IRS or similar agency forms), and deliver other information. Such services can be directed to citizens outside the country following one path and non-citizens seeking the benefit of a visa on another path. The services are delivered in one of a select group of standard languages such as "English" and others spoken and understood in the region of deployment. The services are provided by augmenting the methods and processes described above to address the needs of individuals dealing with consular and related issues. Other tools and the like can be provided, such as an intranet/internet browser, connectivity to intranet and internet resources, capabilities to temporarily store information if a link between the service provider and service seeker is broken for any reason, and using security methods to protect data during storage, transmission, and permanent storage and processing.

Non-citizens visiting a country who entered the country on certain types of visas may be required, prior to departure, to establish that they have complied with the terms of a visa during their stay in that country and that they have not been committed any violation of law that would restrict one's status to leave the host country freely. Establishing such facts may require some critical functions at the time of departure (e.g., establishing eligibility to depart the country in good standing, virtually or physically verifying documents needed for departure (such as passport information), arrival/departure records, establishing the identity of the departing person, validating that the departing person is not a person of interest to any security or other government agency, and that the departing person has met all required conditions of their stay subject to which a visa to enter the country was granted). Such embodiments can interface, integrate and/or exchange data with other systems owned and operated by other entities such as citizenship and immigration services, airlines, and/or law-enforcement agencies and authenticate the visitor's departure status from the host country. Currently, this is a manual process performed by authorized officials at an airport or other departure point.

One method for providing consular services using a traveler assistance station coupled to a network begins with the traveler assistance station detecting the proximity of a user and prompting the user to enter user data (e.g., by typing in information, scanning a passport, visa or other document, referencing data already stored in the system, making an option selection, providing biometric data, etc.) to establish the user's identity and the user's immigration or traveler status. Like other embodiments discussed above, the consular services system can prioritize available answering stations, phones, etc. based on the provided user data. A person answering the traveler assistance station can conference with the user at the station, print a document or authorization for the user, notify governmental authorities of the location of the traveler assistance station in the event that the user needs assistance or for security reasons.

With TAS installed at airports and other departing locations, travelers can scan boarding passes, scan passports and submit the biometric data such as fingerprints, etc. The collected data will be compared to the country's security and law enforcement databases. If the person is cleared to depart, they are issued a departure clearance and or a printed authorization on a boarding card or similar departure document. If the visitor is not cleared to depart, designated officials will be notified of the presence of the visitor at the TAS station. Like VMS embodiments, answering station services will be provided by authorized officials and an answering station attendant will have capabilities like the ones discussed above in the VMS, for example for conferencing with a traveler assistance station, printing a document or authorization at a traveler assistance station, or notifying other governmental personnel of the traveler assistance station's location.

A supply chain management system (which includes, comprises or is related to a targeted consumer exchange system, a trading exchange system, an individual-consumer-oriented electronic coupon system, and/or an individual-consumer-oriented marketing system) uses apparatus, methods, processes, and functions in specific configurations, methods, networking architecture and integration with some conventional techniques to provide advantages in retail and other fields of business by bringing such manufacturers, marketers, retailers and the consumers into a virtual trading room to exchange information and transact business. The apparatus, configurations, architecture, methods and techniques described herein are used to bring together all trade partners (that is, consumers, manufacturers, marketers, retailers and wholesalers), referred to herein as "sellers," and service delivery personnel of such sellers in a virtual trading process where a consumer can make informed purchasing decisions, select brands and quantities, obtain desired services, and preserve historical data of purchases for future decisions, budgeting, monitoring, and convenient shopping. Moreover, consumers can create a social network of shoppers who can share their experiences, write blogs, share recipes and events, exchange ideas, make barter arrangements, and sell and exchange goods, ideas, data, processes, methods or procedures for monetary or non-monetary benefits or consideration, and help other consumers through their experiences. In some cases, parties otherwise considered "sellers" might be consumers in the sense that they, too, can use embodiments of the present invention to purchase products and services and conduct other activities using such embodiments and thus be end users of these embodiments.

Manufacturers can offer custom products based on specific consumer needs, provide information about nutrition values, and other helpful information about their products, announce their product roadmaps and/or make a product more attractive to the consumer by offering competitive advantages for a specific consumer using a mix of sales and marketing techniques, providing infomercials, studies, surveys, etc. to a captive or subscribing audience. Moreover, supply and flow of product in merchant retail facilities can be improved and be performed with more precision and timeliness than with earlier systems. Marketers can direct custom marketing to individuals, as opposed to current marketing methods on a national, regional or group basis. The targeted consumer exchange system also enables the marketer to offer just-in-time personalized marketing (e.g., just-in-time discounts, coupons and/or incentives) to a captive consumer while that consumer is shopping. Through the system, electronic authentication-code-protected coupons that have randomly generated authentication codes are offered to a captive audience that is inclined (or has indicated an inclination) to purchase a competitive product and collect real time return on investment (ROI) data for each marketing dollar spent on such coupons in any given market or region, at each retail or wholesale location, at any given time or duration, and to timely determine and quantify the success of any marketing campaign, thereby enabling the marketers to adjust their campaign during execution, which is not available in the current art of marketing. For example, if a campaign target was to sell 100,000 units of a particular ketchup brand and 20,000 units are sold on the first day, then the marketer can adjust the duration of campaign, adjust coupon values, and identify the stores where most of the coupons are used and, if needed, increase the coupon value in areas where response is slow. This is not available in current marketing methods. Similarly, the marketer may decide to stop issuing a coupon, limit quantities, and/or change the coupon value in a particular zip code, thereby allowing the marketer to track the ROI data (including, e.g., collecting real-time ROI data on each marketing dollar spent) which currently takes a significant time period (e.g., several months) to track and for the most part is inaccurate using current methodologies. Coupons are currently printed in newspapers, etc., are taken to a store and redeemed. The store collects these and sends the collected coupons to a manufacturer, who sends money to the store. Unfortunately, such programs are not timely—there is little chance for adjustment and control by sellers of any kind. Most such programs have 45 day cycles that define when data can be collected, evaluated and changes implemented to reflect consumer practices, attitudes, behavior. Moreover, changes in supply of a product, popularity (or lack thereof) in a given area or market, etc. can only be addressed on 45-60 day intervals. Using embodiments of the present invention, such changes can be made on a daily or even hourly basis.

Sellers can offer customized, personalized, and competitive services to consumers and collect important consumer buying habit data to develop new consumer offerings and create new business models. Sellers also can promote their business by offering personalized services and marketing strategies for specific market segments and population demographics and collect vital data about missed opportunities (e.g., by not carrying a particular brand in an area where demand is already generated by manufacturers and/or marketers).

Additional components are introduced to the apparatus, practices, and methods disclosed above with regard to the visitor management and other systems, etc. to create new apparatus, practices, and methods of doing trade using the targeted consumer exchange system. "Web-servers" are devices that use an operating system and a set of application software and services that allow users to access the server with available methods, technologies, and protocols to receive desired service (for example, buying, selling, and making financial transactions using electronic commerce methods (e-commerce)). "Database servers" are computers that use an operating system and set of application software to create, read, update, and delete data using services defined in database management software. "External storage" is a magnetic, optical, etc. media and any device that reads from and/or writes to such media using computing, storage, and retrieval techniques, being connected to a computer, computing device, system, network, etc. using physical and/or logical connectivity. "Web-based applications" are software applications that deliver business solutions and reside on web-servers. These software applications are available to users via Internet or Intranet architecture and access methods. "Databases" are collections of data conventionally stored on database servers and managed using software applications and database management software. "Human interfacing devices" (HIDs) enable one-way or two-way communication between machines (such as computers) and human beings (for example, keyboards, mice, touch screens, displays, etc.). "Data communications equipment" are electronic components that enable communications between devices and equipment using defined protocols and the like.

"Consumer interface devices" (CIDs) deliver functions similar or analogous to those described in connection with the greeting stations and answering stations of the visitor management system and other systems described above. Examples of such devices will be small or large appliances that operate like a greeting station, answering station, etc. Printers are connected to a computing, communication, or similar devices and provide physical output from such devices. "Scanners" receive an advertised data signal from a responder, or send a request for identification when a responder is sensed, wherein the responder identifies itself in response to such a request. Functionally, there are two types of scanners available for this function, active scanners and passive scanners. Active scanners listen to advertised information from responders and passive scanners are activated to get information from a responder. Either type of scanner can be used in embodiments of the supply chain management system. Responder and scanner types must match. Examples of scanners are RFID readers/scanners, radio receivers, Bluetooth devices, bar code readers, etc. One or more components are configured and linked together to develop a network of appliances, services, applications, codes, micro-codes, processes, methods, interfaces, data acquisition and processing techniques/systems, reporting and information presentation methods, systems and techniques, and interfaces to link to other systems, networks, devices, applications, data, codes and micro-codes to deliver or perform methodologies and processes discussed below and their equivalents.

In one embodiment of the supply chain management system architecture, one or more CIDs are connected together either physically or logically with web servers, database servers, external storage, human interfacing devices, printers, scanners and data communication equipment configured to function as a virtual trading room. The supply chain management system components defined above may be mounted on mobile platforms such as shopping carts, shopping baskets, personal mobility devices (power wheelchairs, scooters, etc.), etc. The supply chain management system components are configured to work together or as a stand-alone system. The system can download, retrieve, process, store and periodically update data of interest, local or remote copies of product and service catalogs, business rules/methods, data acquisition methods, data processing methods, processes, computing methods, processes, algorithms, code(s), and information delivery methods, storage methods, store-and-forwarding methods in any visual, audio, legible, electronic, and/or optical form and fashion using any locally attached, remotely located, networked or stand-alone devices, methods, and processes used to deliver such data and information in the form and fashion required by the supply chain management system. The appliances and/or devices can be integrated with other devices, equipment, systems, methods, processes, and applications located locally, remotely, attached to such appliances physically or logically using any methods, protocols, connectivity architectures, code(s), and/or algorithms.

Figure 29:
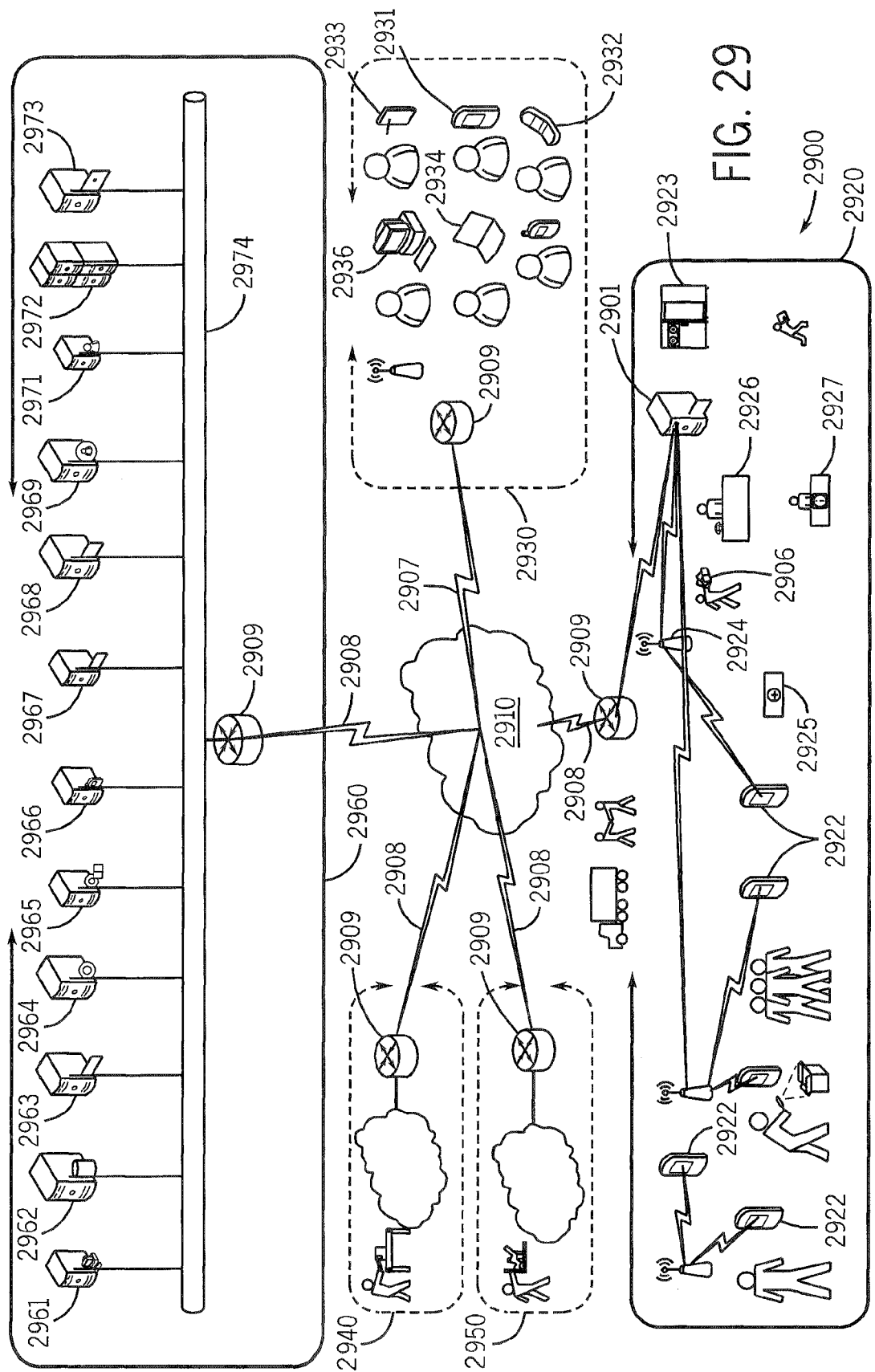
FIG. 29 shows an exemplary targeted consumer exchange system embodiment that includes a virtual trading room embodiment, electronic coupon system embodiment, and individual-consumer-oriented marketing system embodiment.
Figure 30:
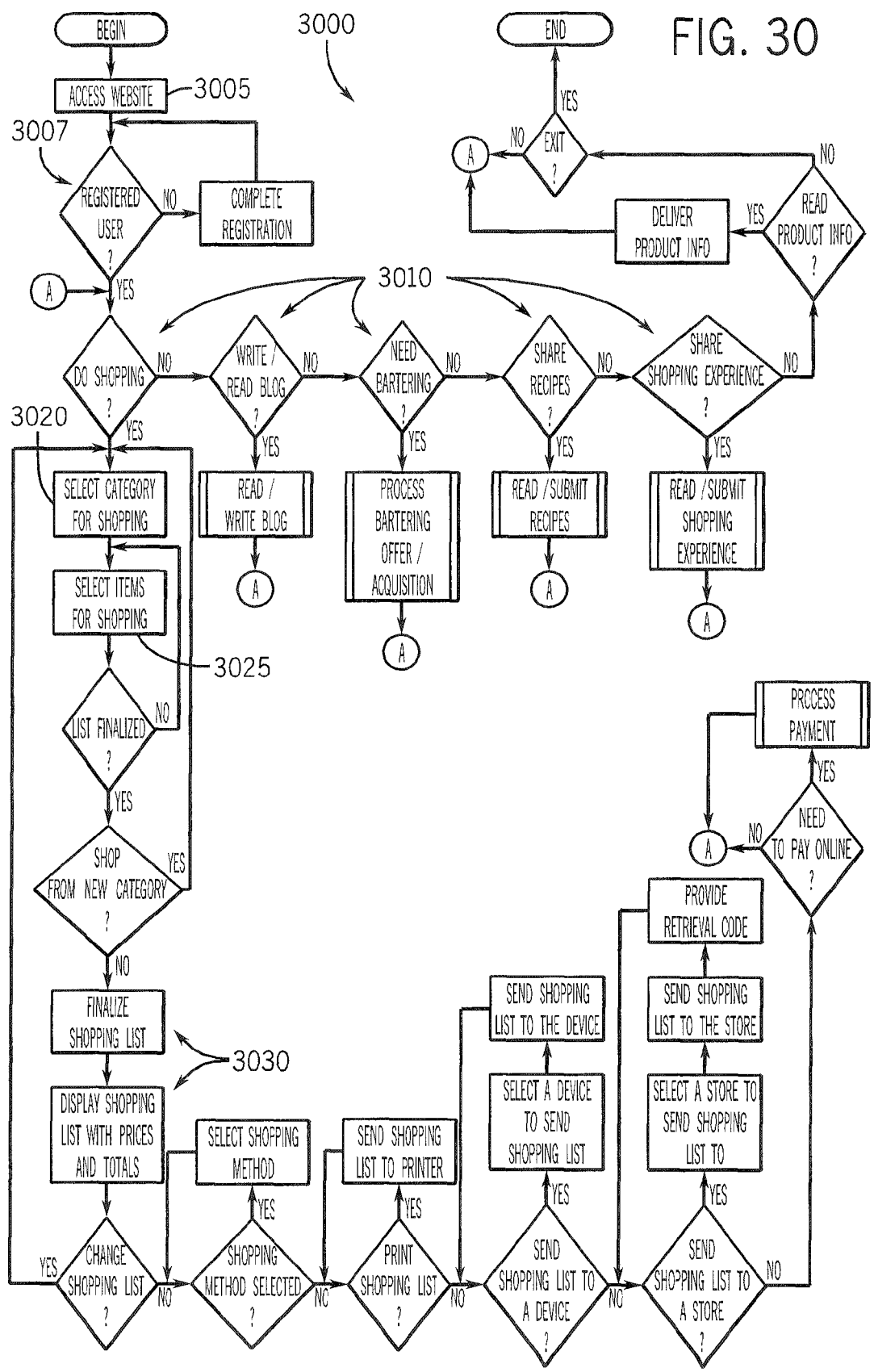
FIG. 30 shows an exemplary process for an exemplary targeted consumer exchange system embodiment that includes a trading system embodiment, electronic coupon system embodiment, and individual-consumer-oriented marketing system embodiment outside a store.
Figure 31:
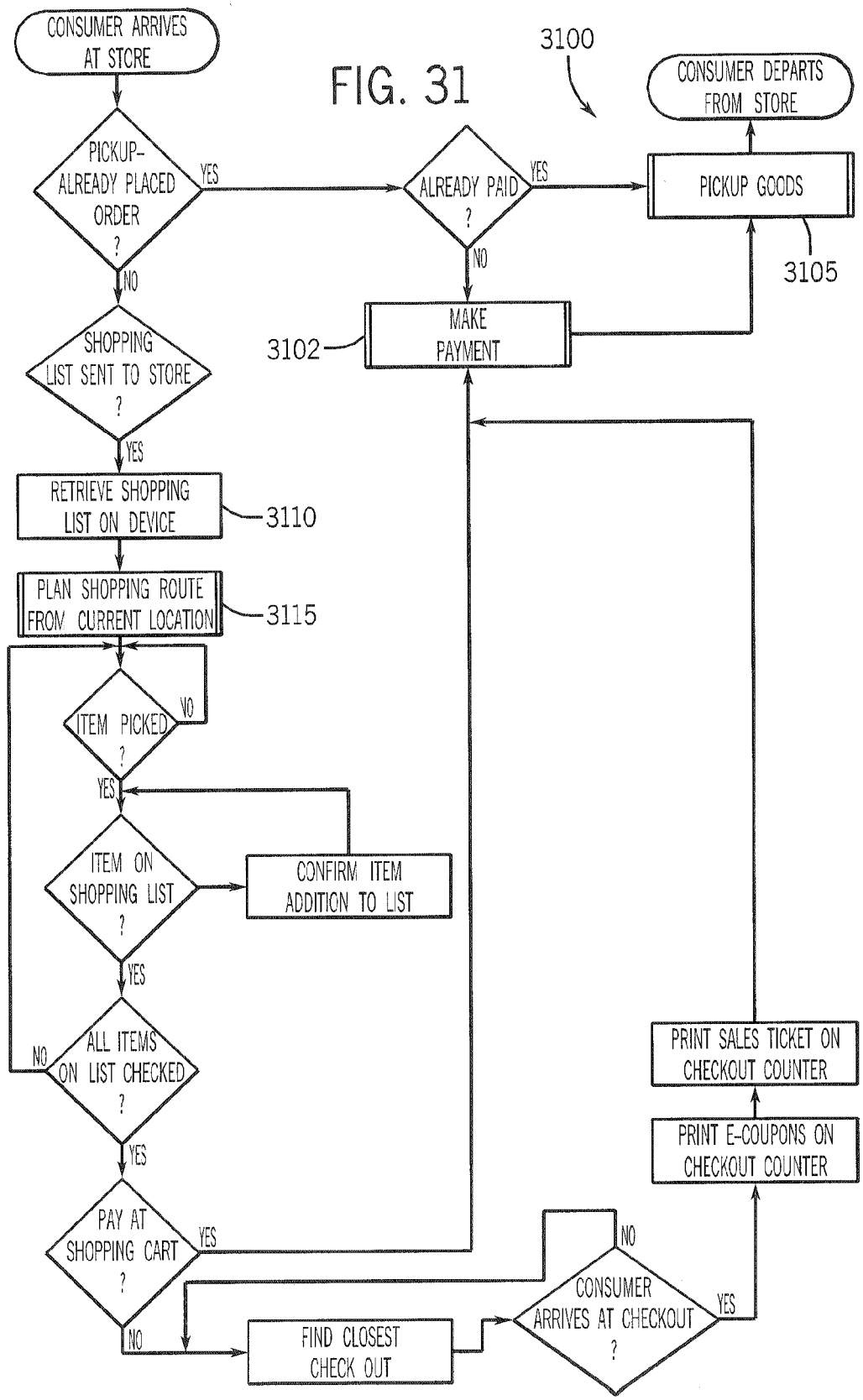
FIG. 31 shows an exemplary process flow for an exemplary targeted consumer exchange system embodiment that includes a trading system embodiment, electronic coupon system embodiment, and individual-consumer-oriented marketing system embodiment inside a store.
Figure 32:
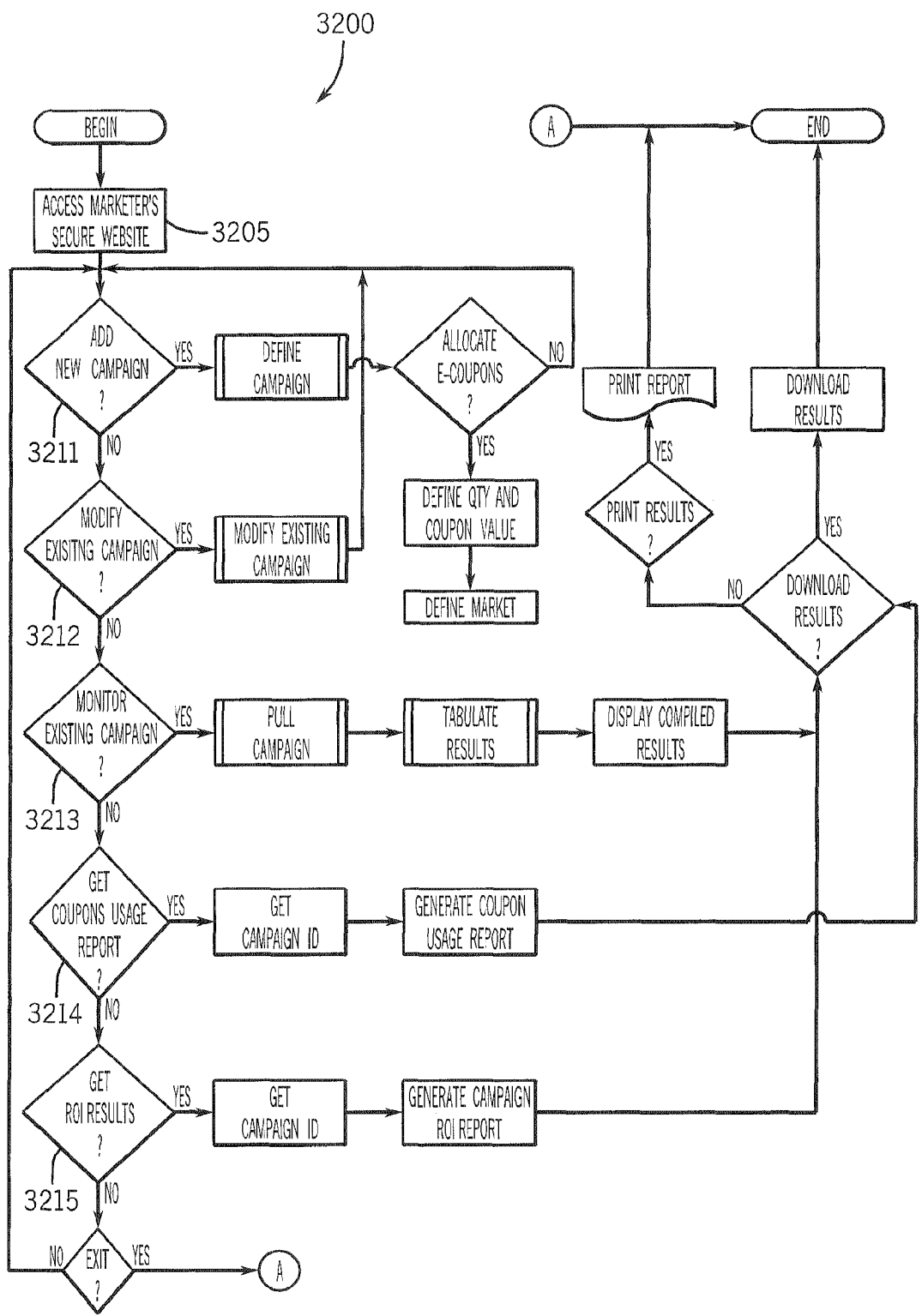
FIG. 32 shows exemplary functions available to a marketer in a targeted consumer exchange system embodiment.
Figure 33:
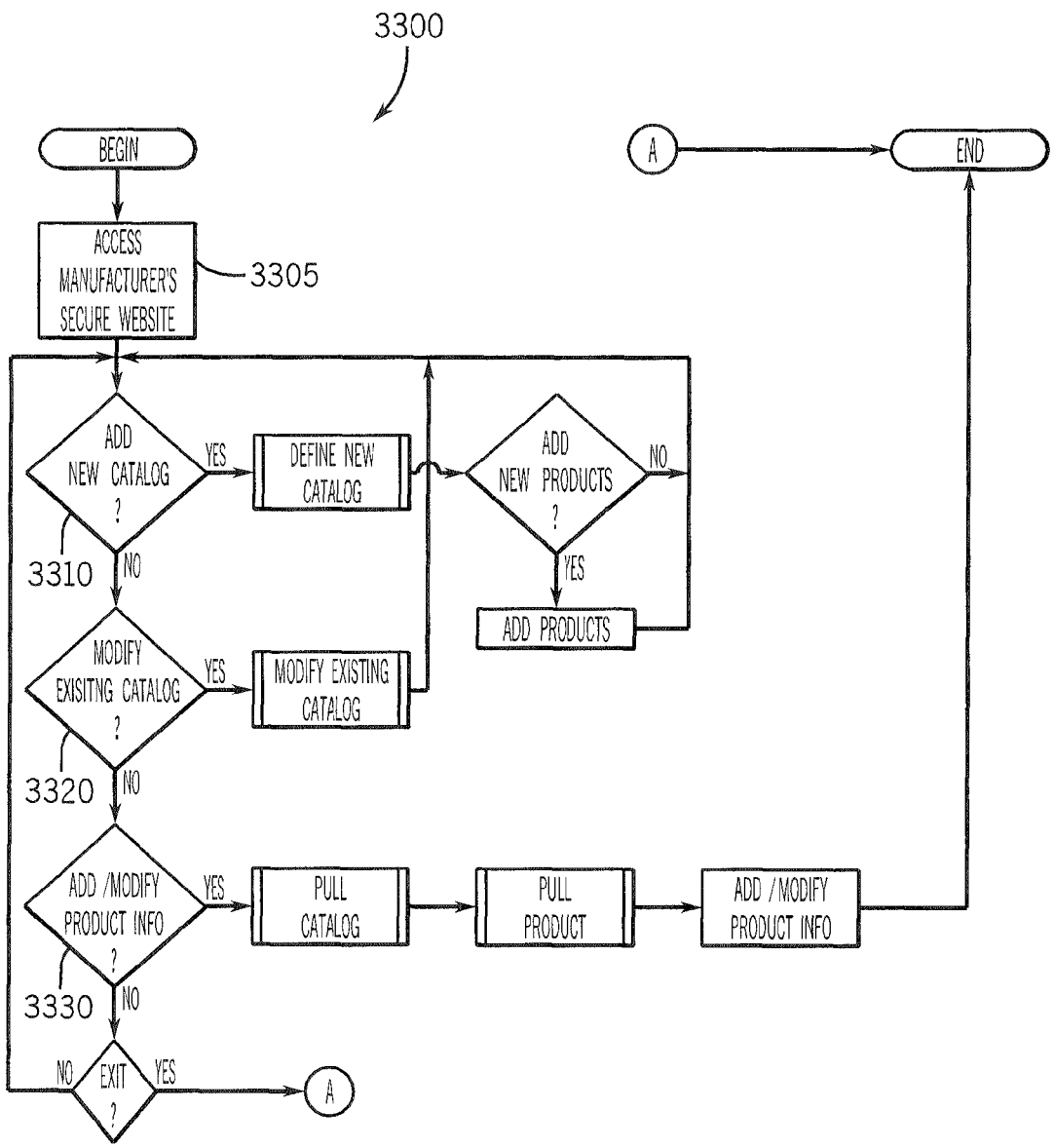
FIG. 33 shows exemplary functions available to a manufacturer in a targeted consumer exchange system embodiment.
Figure 34:
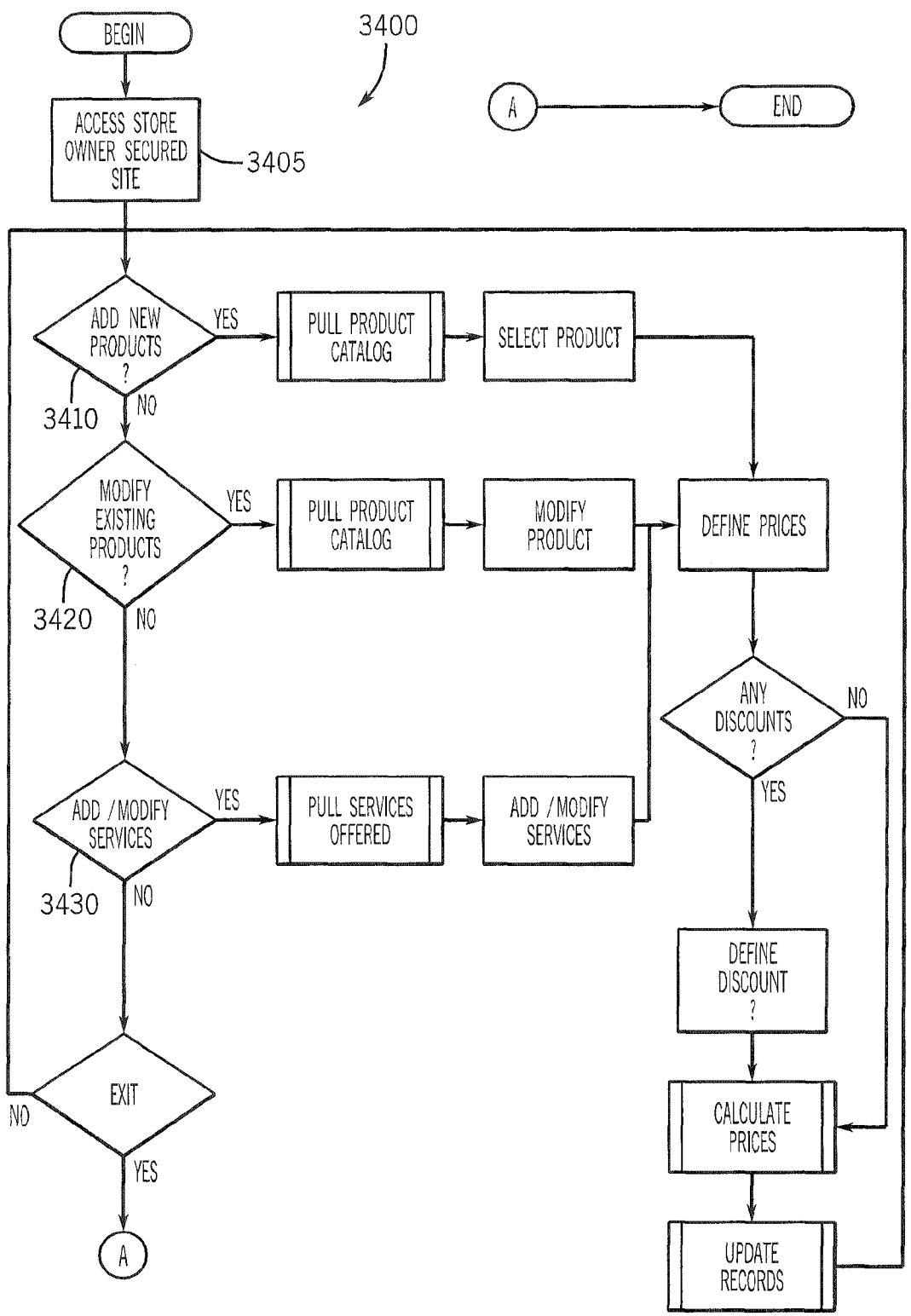
FIG. 34 shows exemplary processes available to store owners in a targeted consumer exchange system embodiment.

FIG. 29 shows one embodiment of a supply chain management system 2900 that functions as a virtual trading room in some embodiments. In some embodiments of the present invention, system 2900 might be organized as a consumer club or subscription service that provides consumers with special programs and discounts, as well as access to the devices, etc. making up system 2900. Various seller devices (e.g., computers, etc.) are found in marketers' domains and marketers' devices 2950, manufacturers' domains and manufacturers' devices 2940, suppliers' domains and suppliers' devices, retail facilities devices, etc. and can access network 2910, for example using communications devices 2909 connected to network 2910 via a secured access 2908 or a public access 2907. Such seller devices can access the system's product and service catalogs to add, update, modify, and remove products and services. They also can define, update, modify, adjust and delete marketing campaigns (for example, campaigns providing money saving or similar coupons to consumers) and receive ROI quick reports for such campaigns by tracking coupon use as coupons are serialized, distributed, and redeemed electronically. Marketing campaigns can be adjusted in a number of ways—e.g., adjusting one or more time limits pertaining to the marketing campaign, adjusting coupon invalidation deadlines, adjusting coupon re-issuance to customers after non-use by a previous customer, adjusting coupon values and/or adjusting availability and/or values of coupons in some stores where response is slow.

Various connectivity, server, management, etc. devices 2960 are connected to the network via a local connectivity/networking architecture 2974 and communication devices 2909 to facilitate the various functions of system 2900—for example, management servers 2961, database servers 2962, e-commerce servers 2963, web servers 2964, streaming data devices 2965, mobile device servers 2966, email and text messaging servers 2967, file and application servers 2968, content management servers 2969, real time communication servers 2971, external storage devices 2972 (also referred to as "network memory storage apparatus"), and certificate servers 2973. Retail facilities provide access to network 2910 and the domains, apparatus and services available thereon and therethrough using consumer information processing equipment, which includes equipment and apparatus used by consumers and by store owners and operators to access network 2910 and perform the various functions discussed herein.

The supply chain management system can be available to in-store shoppers, shoppers using internet or other non-traditional purchase methods to make current purchasing decisions, and to people who want to do their homework before shopping (e.g., comparing prices, preparing an optimized shopping list, selecting a convenient time to visit a store), and selecting a preferred method of shopping such as pick-up, in-store shopping, pre-paid ordering, home delivery, etc. Product lists can be accumulated over time, and such lists allow online/immediate comparison pricing by consumers and merchants/suppliers. The user interfaces are provided with multi-lingual and other capabilities so that a consumer can select the language of his/her choice and/or make a selection to accommodate a user's disabilities (for example, to assist users who are hearing-impaired, sight-impaired, mobility-impaired, etc.).

A scanner matrix 2924 as defined in connection with FIGS. 25 and 26, above, is implemented inside retail facilities such as store domain 2920 to provide information about location of items in the store, shopping routes through the store, guidance in the store, locating a check-out location 2925, 2926, and any other similar, monitoring and location services. The supply chain management system also can include a repository of product catalogs installed on database servers using a centralized or distributed architecture. A "centralized" architecture is defined as logical or physical consolidated storage of all catalogs (or catalog data) in one place and on one or more database servers, whereas a "distributed" architecture refers to catalogs or catalog data logically or physically spanning more than one database server, located in the same place or dispersed geographically. Each catalog can represent a specific consumer need. For example, a "Grocery Catalog" can include items commonly found in a household pantry (canned vegetables, oatmeal, soft drinks, etc.). An "Apparel Catalog" may include products like shirts, pants, scarves, ties, etc. Each catalog can have multiple categories and include goods from multiple sellers and/or locations, with a number of items manufactured or commercially available in such category. Catalogs are accessible by authenticated and authorized consumers who have devices and network connectivity using appropriate devices, such as web interfaces, shopping cart-mounted devices, cell phones, PDAs or similar devices in a store. Manufacturers and marketers can access catalogs through secured access via the internet or private networks (both physically and virtually, using one or more user interfaces and the web services). Retailers and wholesalers can access the targeted consumer exchange system catalogs in a similar manner. Each user group can access catalogs for specific purposes defined through the user interfaces.

The supply chain management system delivers services to both in-store and off-store shopping customers through consumer information processing equipment such as CIDs and internet/intranet access equipment. For example, a consumer can access and research prices, availability, coupon offerings, store payment policies and services available (for example, home delivery or pick-up). Consumers also can purchase items, prepare shopping lists, select the store(s) to purchase from, and/or the date and time when the purchases will be made. If the store offers delivery or pick-up service (when the order is picked up by store staff, packed, and made ready for pick-up) then services such as pre-paying by credit card or payment at pick-up can be used. The consumer also can save (upload) a shopping list for future reference, print it to take along, download it to a personal device such as a smart phone 2931, phone 2932, PDA 2933, laptop 2934, notebook 2935, desktop 2936, etc. or forward it to stores electronically via network 2910 and retrieve it from the network 2910 (or one of the devices 2960 connected to network 2910) on one of a number of in-store remote consumer devices, such as CID 2922, can operate as a stand-alone or networked system. Remote consumer device 2922 can be a CID mounted on a shopping cart or be provided as a hand-held device by the store, accessed by entering an authentication code provided to the consumer during an off-store session using the internet or intranet. A portable terminal of this type can be found in U.S. Pat. No. 6,595,417, issued to O'Hagan et al., the entire disclosure of which is incorporated by reference for all purposes. These remote consumer devices gather consumer information and store the collected consumer information on one or more network memory storage devices or apparatus, such as external storage devices 2972. Such consumer information can include consumer buying practices, consumer shopping practices, consumer price sensitivity, consumer feedback regarding use of the system, consumer demographics, and consumer payment and pre-payment methods (in-store and external) using checks, cash, debit cards, credit cards or food stamps. Likewise, seller information is collected from sellers, retail facilities and the like and stored on one or more network memory storage devices or apparatus. Such collected seller and/or consumer information can then be made available to various network devices, such as remote consumer devices and/or CIDs, for example.

When in a store, a consumer can use CID 2922 (again, standalone, networked, or shopping cart-mounted) to download previously-prepared shopping lists forwarded to the store earlier. CID 2922 intelligently prepares an in-store shopping route from the current location, and can rearrange the order of items on the shopping list to match the shopping route. An in-store CID 2922 can notify the consumer about the next item to be picked up, checking off items already picked up. This can be done with consumer inputs using a touch screen or scanning picked-up items using a barcode/UPC scanner or the like. If the store has responders on products, such as radio frequency identification (RFID) tags, then the scanner (RFID reader in this example) will scan and read the product pickup. The CID can automatically prepare a sale ticket, which is transmitted to the store point of sale system when the consumer is ready to check out. The in-store CID also can be used to find in-store locations of new items that were not included in the original shopping list, or if there was no shopping list. When the customer is at the checkout counter, a CID or HID (e.g., standalone, networked or cart-mounted devices) can communicate wirelessly with a checkout counter printer or other printer or electronic device and print coupons for the products in the shopping list or redeem by other electronic methods. A checkout person can use these bar-coded coupons to credit the consumer purchases. If no shopping list was prepared in advance, then the consumer can be notified (based on the location of the cart in the store) which manufacturers are offering sale coupons in the present aisle or location (for example, the dairy case). The consumer may decide to accept or deny a coupon; such coupons can be printed or redeemed by other electronic methods at check-out and credit will then be provided to the consumer. If a coupon is not redeemed within a reasonable time period (for example, two hours), then the coupon is invalidated and reissued to another customer (where invalidation and re-issuance criteria can be adjusted by a marketer accessing the network). A shopping cart-mounted CID 2922 can communicate constantly with other CIDs in the store. If communication fails, then store management and the shopper can be notified of the failure. Moreover, if a CID is taken out of a pre-defined area and cannot be tracked by the scanner matrix, the CID can generate a loud, audible noise to identify potential theft or removal of the CID from the permissible use area in the store.

An RFID scanner constantly evaluates items in the cart with RFID tags by scanning the tags and preparing an accurate checkout sale ticket that can be transmitted to the point of sales system at the checkout counter or allow the consumer to pay by credit or debit card at a consumer interface checkout device (e.g., self-serve checkout) or at the cart and provide sales data and payment information to the store point of sales system or other store owned and/or operated computing or data acquisition system in electronic, printed, visual, audio or any other format commonly used to communicate data and information in the industry. A consumer can touch a live assistance button on a CID touch screen and be connected to an answering service operator 2927 located locally (e.g. at a customer service desk in the store) or remotely using two-way video and/or audio conferencing. The answering person can take control of the CID and remotely deliver visual or audio responses and/or directions to the consumer.

Among other benefits of supply chain management system, sending shoppers just-in-time electronic coupons (or other just in time discounts, coupons and/or incentives) with short validity periods enables manufacturers, marketers, suppliers and other sellers to personalize and focus marketing of products and services to individual purchasers right at the time of purchase and to know the immediate and/or precise needs of the customer. Authentication codes on electronic coupons validate coupons and capture data about redemptions such as date, time, store, zip code, etc. Authentication and electronic redemption methods offered by embodiments of the supply chain management system also mitigate against fraudulent use of counterfeit coupons. Recent data suggest a substantial increase in forgery in current discount coupon systems and other such practices which significantly hurts retailers and manufacturers. Also, embodiments of the supply chain management system help sellers optimize their use of resources based on key metrics, data and trends delivered by the system (for example, balancing staff assignments by using predicted consumer traffic data and other similar metrics) in a timely fashion. Retailers and wholesalers can publish in-store location maps and can use the interface to tie to their inventory system or point of sales system for electronic check-out or reduced consumer wait at the check-out.

Medical consultants deliver services by visually and physically examining the patient, interrogating the patient about his/her condition, and collecting data (e.g., blood pressure, pulse, temperature, etc.) to narrow the causes for a patient's medical condition ("diagnosis"). The consultant may have the patient undergo tests performed by machines and other individuals, and may use such test results to refine a diagnosis of the patient's medical condition. During or upon conclusion of such consultation, the medical consultant generates notes using methods such as writing, audio/video recording, etc. Those notes typically become part of the patient's medical record (also referred to as "patient historical data"). At each visit, data such as weight, body temperature, blood pressure, etc. are collected as "vital data." The consultant reviews and considers current and historical data during patient consultation and treatment.

Patient historical data typically includes the patient's personal information, medical history, family history, and any medical and treatment related notes, test results, radiography images, previous medical treatments and, in some countries, financial information such as the patient's insurance data, etc. Authorized health care service providers such as physicians, consultants, pharmacists, etc. look at this record before providing new or continuing treatment. Strict security/privacy/regulatory requirements in most developed countries safeguard patient medical records and data; developing and under-developed countries may not have such strict requirements. It is imperative for a consultant to establish positive identity of the patient.

Hospitals, clinics and physicians establish their physical locations where they provide healthcare to patients. Patients typically have to go to such locations to have medical conditions diagnosed and treatments prescribed. The shortage of medical consultants and the costs of establishing new facilities leave a large patient base in urban and rural areas without prompt and ready medical treatment nearby. Traveling to such locations economically impacts patients (e.g., lost work/productive time, travel expenses). The situation is worse for highly qualified and experienced specialists such as oncologists, cardiologists, etc., who are in acute shortage in developed countries and might not even be available to patients in some urban areas. In most developing countries, the healthcare delivery infrastructure is almost non-existent and there are areas where no doctor is available to provide treatment to patients in need of healthcare.

Remote examination of and consultation with patients with no assistance at the patient's location is typically inadvisable since the patient may need assistance with medical equipment, documents and other materials, prescription and other information, etc. On the other hand, hospitals, clinics, etc. do not want to have to establish such remote locations themselves, if possible. Embodiments of the present invention of the present invention provide examination/consultation locations at pharmacies, which provide professional personnel already onsite, and typically offer patients locations that are convenient, since pharmacies are found quite readily in many countries and communities. No new facilities have to built, no new staff has to be hired, yet professional-assisted examination and consultation can be provided using embodiments of the present invention.

Apparatus, methods, systems and processes according to embodiments of the present invention enable medical/healthcare providers to deliver services in areas closer to a patient's residence and enable one or more of the following: consultation with patients, remote examination, vital data collection, providing medication prescriptions, test prescriptions, etc. at a remote pharmacy location; consultation among several medical consultants, keeping the patient included in such consultation; patient self check-in at an emergency room or other facility with the option of consulting with a remotely located consultant (e.g., in another emergency room, etc.) in non-life-threatening emergencies (e.g., stomachache, headache, toothache, high temperature, etc.).

Further equipment, devices and components are added to previously defined apparatus (e.g., shown in FIGS. 1 and 2) as part of a remote medical consulting system. For example, the system includes two displays for each consultant station (used by medical consultants)—a picture archiving communication system (PACS) display using a high-resolution color and gray scale display for radiography, computed tomography, and magnetic resonance imaging is added as a second display to the apparatus of FIG. 1 (in addition to the conferencing screen that is already available) to enable display of radiographic (x-ray or like), computed tomography (CT-scan or like), or magnetic resonance (MRI or like) images during consultation with the patient and/or other consultant. Also, one or more stations can pull radiographic, tomography, or MRI data from one or more local or remote "image servers" connected to the environment network physically and/or logically so that the station has communication access to the image servers. An authorized user of a station can retrieve medical images required during a consulting session from an image server. One or more stations also can conference additional stations in an audio and/or video conference during a consulting session. Alternatively, if the medical consultant needs to contact another consultant who is available by phone, an audio only call is made from the consultant station. Each station can also control the patient station camera (e.g., pan, tilt, zoom) to examine the patient. The consultant station can implement an emergency triage process, which is known to any person skilled in medical consulting, to identify the needs of a person at the patient station. For a patient station, a weight scale, sphygmomanometer (blood pressure gauge) and thermometer are added to the appliance of FIG. 1. These devices' measurements are provided to the remote medical consulting system using integration or interfacing techniques.

Patient identification data readers (e.g., driver license reader, document scanner, barcode scanner, magnetic card reader (e.g., for medical cards, credit cards, etc.), and signature pad, etc.) can be added as input peripherals to the patient station as well as the consultant stations. The remotely operated pan, tilt, and zoom (PTZ) camera can be controlled by both the patient station and the consultant station. Patient stations can be connected to consultant stations using available networking technologies, methods, and protocols. A secure link can be used between each patient station and consultant station, including among three or more stations.

The remote medical consulting system uses the consultant's eyes, ears and brain and the hands of a patient (or trained assistant) at a patient station to replicate collocated consultation at a consulting location. For example, a patient can point to a body area where there is pain or press the patient's abdomen at points to identify where there is pain and the extent and quality of pain (moving up, moving down, throbbing, constant, etc.)

Figure 35:
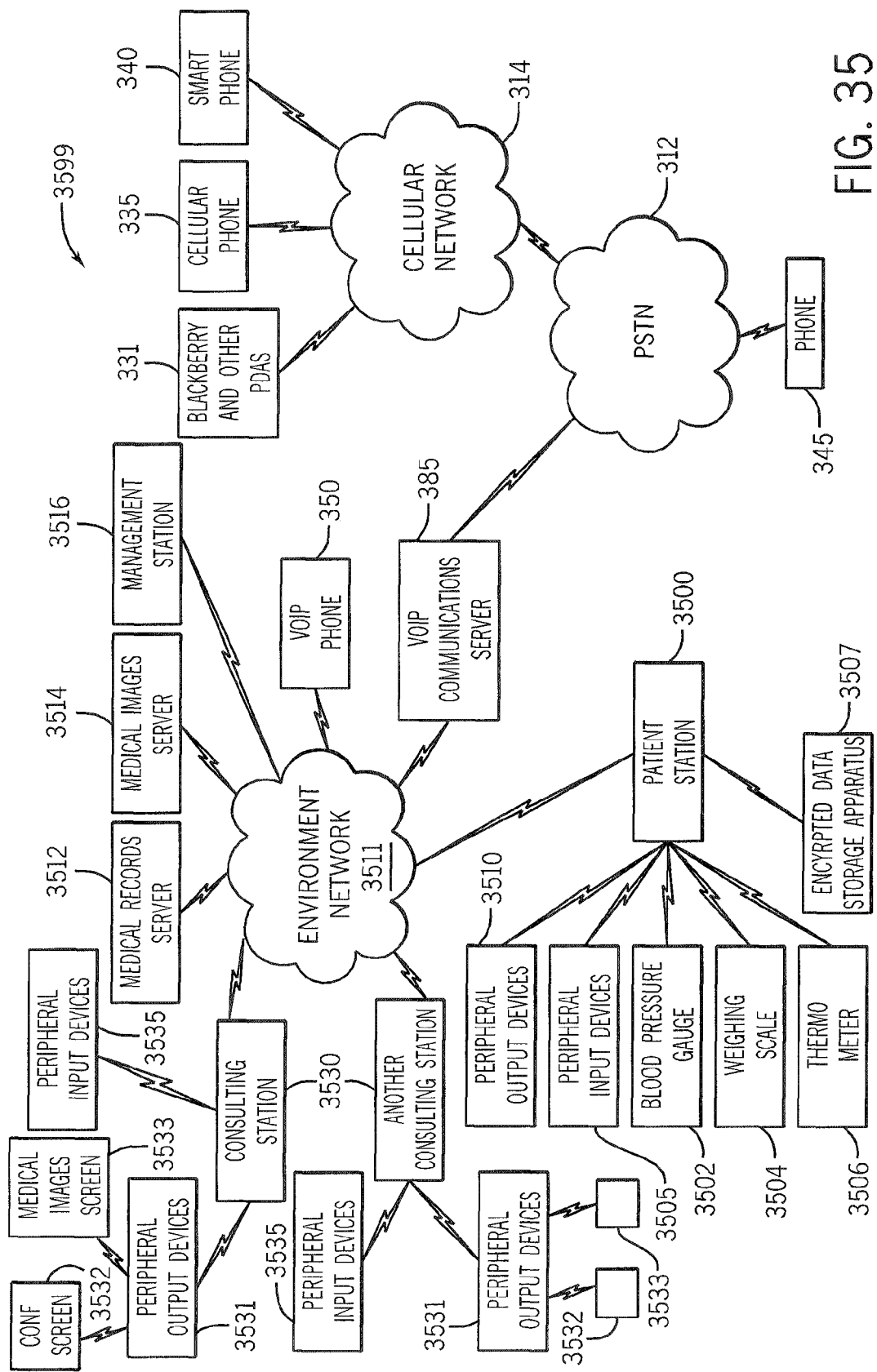
FIG. 35 shows an exemplary virtual medical consulting system embodiment implemented in connection with a pharmacy-situated patient station.

In an embodiment of the present invention shown in FIG. 35, a patient consultant station 3500 has one or more peripheral input devices 3505 (e.g., electronic signature pad, touch screen, document scanner, barcode reader, keyboard, mouse). A printer is attached as part of the peripheral output device group 3510. Such peripheral input/output devices can include patient station communication apparatus—speakers, microphones, display screens, touch screens, cameras, etc. used to allow communication between a patient and a medical consultant during a session. Patient data collection apparatus also is provided in each station 3500. For example, a blood pressure gauge 3502, scale 3504 and thermometer 3506 are all integrated and/or interfaced with station 3500 in FIG. 35. Other patient data collection apparatus devices can be included, as will be appreciated by those skilled in the art. The patient station 3500 also uses an encrypted data storage apparatus 3507 that is coupled to station 3500 so that data acquired from the patient (e.g., through patient inputs, patient vitals that are collected, scanned documents and other information, etc.) is stored during a given consultation session. The data is encrypted to protect patient confidentiality and privacy, but the encrypted data remains on the station storage apparatus 3507 in case of a problem (e.g., loss of power, disconnection between the two or more participants, etc.) so that all of that data does not need to be re-acquired when the problem is corrected. Patient station 3500 is connected to a network 3511 that can include any required server devices and storage apparatus appropriate to the uses described herein (e.g., a medical records server and storage apparatus 3512, a medical images server and storage apparatus 3514 and a management station 3516).

A consultant station 3530 in FIG. 35 also has communication apparatus similar to the patient station communication apparatus. Moreover, the consultant station 3530 has one or more various patient data evaluation apparatus devices that permit the consultant to evaluate patient data collected and sent by the patient station to the consultant station. For example, the patient data evaluation apparatus has peripheral output devices 3531 which includes two displays—a normal video display 3532 (e.g., appropriate for video conferencing) and a PACS display 3533 to view images. Station 3530 likewise has similar peripheral input devices 3535. A printer, plotter and/or other printing device along with other digital, optical, and magnetic devices are attached as part of peripheral output device group 3531. For purposes of illustration, multiple consultant stations 3530 have a similar configurations. As noted above, a medical images server 3514, a medical records server 3512, and a management station 3516 are also coupled to the network 3511 in the exemplary system 3599. The medical images server stores radiographic (e.g., x-ray), CT-scan or MRI images of patients. Medical records server 3514 stores medical records and registration data for all patients. Management station 3516 adds, configures, monitors and removes data, or performs other administrative tasks as might be required for the exemplary system.

A patient station can be installed in a private room, referred to herein as a "patient room" or any other relatively private location in a pharmacy. The patient room can be supervised by a professional member of the pharmacy's staff. Retail pharmacies are an appropriate location for such patient rooms because they are already associated with healthcare and are found in urban and rural areas. Signs displayed in the patient room can inform patients that this facility is for a non-emergency, follow-up, non-life-threatening treatment and reception only; if the patient is experiencing more serious conditions (e.g., chest pains, bleeding, or a broken bone), then the patient should not use the remote medical consulting room and should instead notify pharmacy staff, call emergency medical services or the like.

When the patient arrives at a consulting room, the patient status is either an "existing" patient (with patient historical data at one or more accessible locations) or a "new" patient (possibly without any accessible patient historical data). The patient initiates a consultation request by proving his/her identity and, in some cases, selecting a consultant station 3530 for the consultation. A new patient also can register with a facility equipped with a consultant station 3530. If a patient station 3500 is associated with a number of consultant stations 3530 located in different facilities, then the patient station provides a list of available facilities. The patient chooses the desired facility contact for consultation and treatment. An interactive guidance system at the patient station displays images and audio loops to assist the patient in proving identity (e.g., presenting a drivers license, a healthcare-issued card and/or other documents to satisfy security requirements) and the patient's age. For new patient registration, patients are asked questions normally asked during healthcare facility registration. If a document must be uploaded to the healthcare facility, a scanner can scan and upload the patient data. The patient may need to sign documents such as HIPAA privacy notices and certifications that the patient does not believe his condition is life threatening An existing patient can prove his identity by satisfying at least two of the following requirements: (1) something the patient has (e.g., a driver's license, healthcare-issued card), (2) something the patient knows (e.g., date of birth, social security number, etc.), and/or (3) biometric proof.

Once identity is established, patient station 3500 sends that data to medical records server 3512 (which functions as a "patient historical data memory storage apparatus" or the like) to retrieve patient historical data or, for a new registration, to register the patient and obtain a medical records number. The patient then provides vital data using patient station devices and answers questions regarding current medical condition, which can conform to any jurisdiction's medical procedures. Upon receipt of vital data and question responses, a report is created for the consultant using a standard healthcare reporting format. The patient station then requests an audio-video (AV) conferencing session with the selected consultant station and, if none is selected, then the patient's conference is referred to the healthcare facility that is closest to the patient station.

At the consultant station, the consultant proves his identity, authorization, and eligibility to provide consultation (e.g., proving at least two of the three security conditions defined above), verified by an independent healthcare authorization system. Such a system can be included in management station 3516. The consultant can use the consultant station only after being verified and authorized. During the session, the consultant station can "listen" for requests to establish a session with patient stations.

Upon receiving a request to begin a consulting session (e.g., AV conference), a verified consultant acknowledges the consultation request and receives medical report and medical record locator information from the patient station (e.g., collected vital data, other collected patient data, patient station location, etc.). The consultant can then review any received data and consult with the patient. For visual examination the physician can control a patient station camera to pan, tilt and zoom to visually examine the patient. For physical examination the physician can ask the patient and/or an authorized assistant to perform certain requested actions while the physician monitors these activities using the communication apparatus at the consultant station. If the consultant needs patient medical images, the consultant can request and display the images on the PACS display. While connected to the system, the consultant station creates, manages and updates a list of all other consultant stations configured as a group using the management station.

During consultation, if the consultant needs to contact a second consultant, the first consultant can select the second consultant from a list if that consultant is available at another consultant station or alternatively can contact by phone. If the second consultant is available at another consultant station, a request for AV conferencing is initiated by the first consultant station. When the consultant at the second consultant station accepts the request, an AV conference session is established between the first and second consultant stations. The first consultant station can share (subject to authorization) medical images, medical records and/or examination data with the second consultant station in real time. To have a private conversation, the first consultant station can select a "Hold" button that stops the AV stream to the patient station, resuming the patient station conference by selecting "Resume" on the display. A consultant station also can take control of the patient station display to show images, writings, scribbling, drawings, etc. on the patient station screen to explain a point to the patient.

The consultant can request a prescription or test for the patient at the consultant station and sign it using consultant station signature pad. Such prescription or test document can be printed at the patient station printer and/or simultaneously at a pharmacy subscribing to the system, or can be uploaded in digital form to a pharmacy system if such system is interfaced with the remote medical consulting system. At the conclusion of the consultation session, the patient station and any consultant station can be "reset" to be available for the next consultation session. Resetting a patient or consultant station can include making sure that all screens, printers, etc. (i.e., input, output and other devices) are clear of any confidential medical and/or personal information about the patient or the nature of the consultation that was conducted. Also, the patient station and/or consultant station can be disinfected to provide a clean working location for the participants in the next consultation. In addition to those described above, process embodiments are shown in FIGS. 36, 37 and 38.

Figure 36:
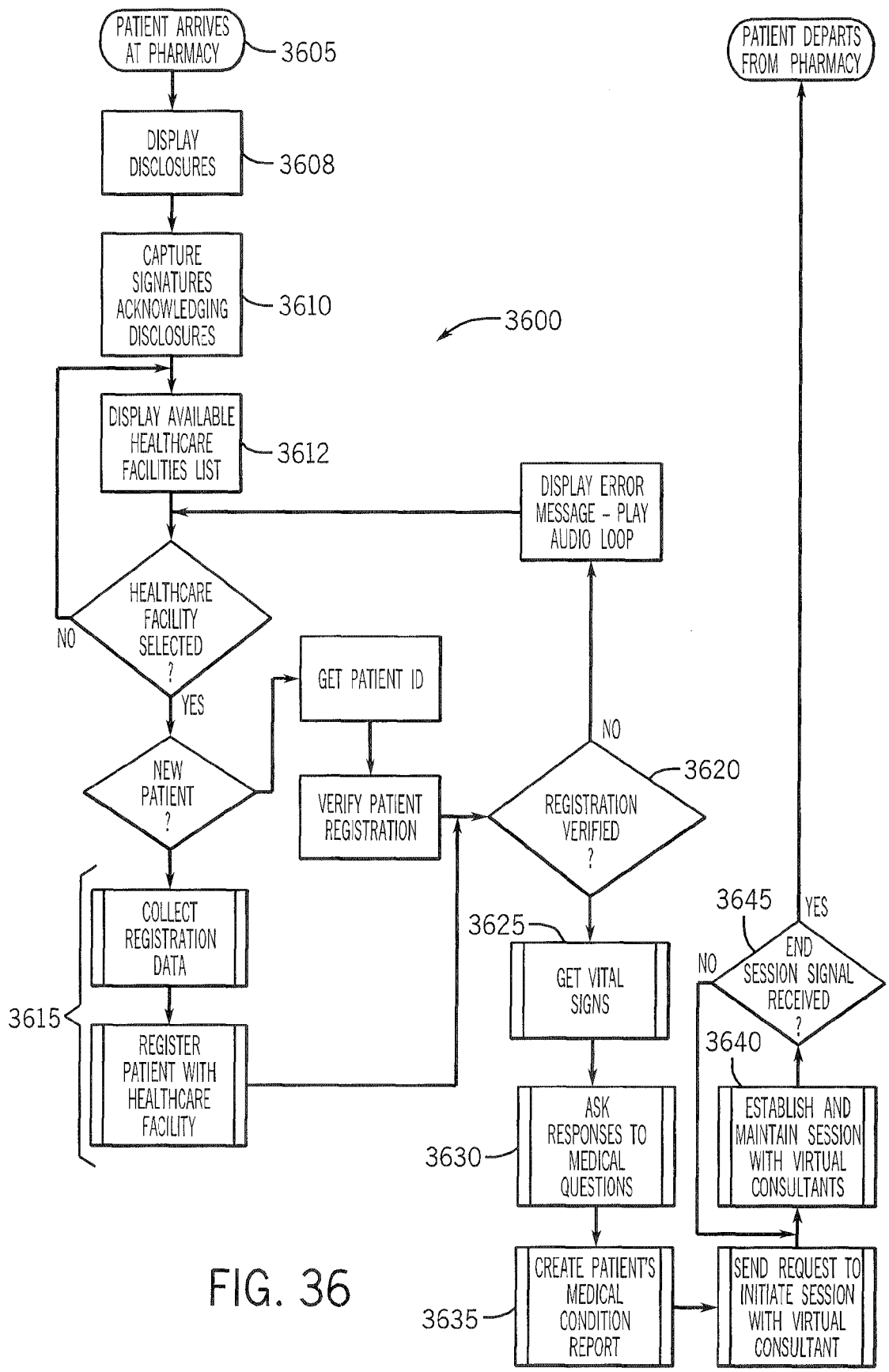
FIG. 36 is a flow diagram of an exemplary process at a patient station in a pharmacy in a virtual medical consulting system embodiment.

In FIG. 36 illustrates a patient station process 3600 and begins with a patient arriving at a pharmacy patient station 3605, which displays required disclosures and the like at 3608 and allows the patient to acknowledge such disclosures at 3610. The patient can then select a healthcare facility from an available facilities list at 3612 and register at 3615, if a new patient. The patient, whether new or previously registered, has their registration verified at 3620. Vital signs are then collected at 3625, as are answers to medical questions at 3630. A patient medical condition report is started and generated at 3635, which also begins the encrypted patient data recording process, noted above. A consultation session is then commenced and conducted at 3640. At the conclusion of the session, a session is properly concluded with the transmission of an "end session" signal at 3645, which also clears the encrypted patient data stored on the storage apparatus of the patient station.

Figure 37:
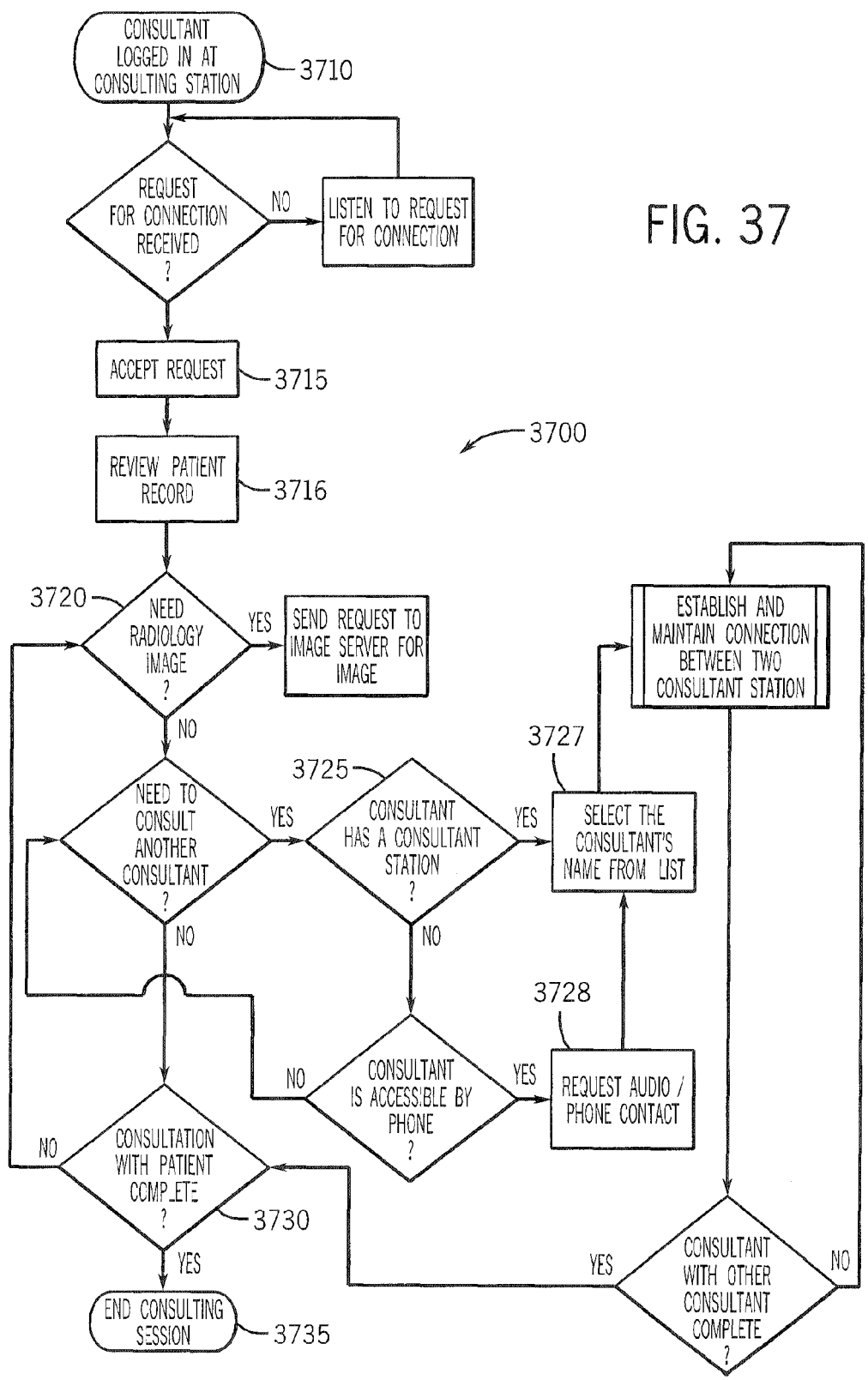
FIG. 37 is a flow diagram of an exemplary process at a consultant station in a virtual medical consulting system embodiment.

FIG. 37 tracks a consultant station process 3700 that begins with a consultant logging in a consultant station at 3710, which requires positively establishing the consultant's identity, which can include something they have (e.g., ID card), something they know (e.g., authorization code), and biometric confirmation of the consultant's identity (e.g., fingerprint). The consultant accepts a consultation request at 3715 and reviews patient data that can include the patient's medical record at 3716. If the consultant needs one or more medial images, those can be obtained at 3720. Likewise, if the consultant wishes to bring in a second consultant on the consultation, that can be done at 3725 by either using another consultant station at 3727 or by phone at 3728. When the consultation is complete at 3730, the session/consultation is ended at 3735, which includes erasing any encrypted patient data maintained at the patient station involved. Conclusion of a consultation also can generate a signal to the patient station to automatically disinfect itself (e.g., using automated disinfectant sprays and the like) when the patient station is clear of any people.

Figure 38:
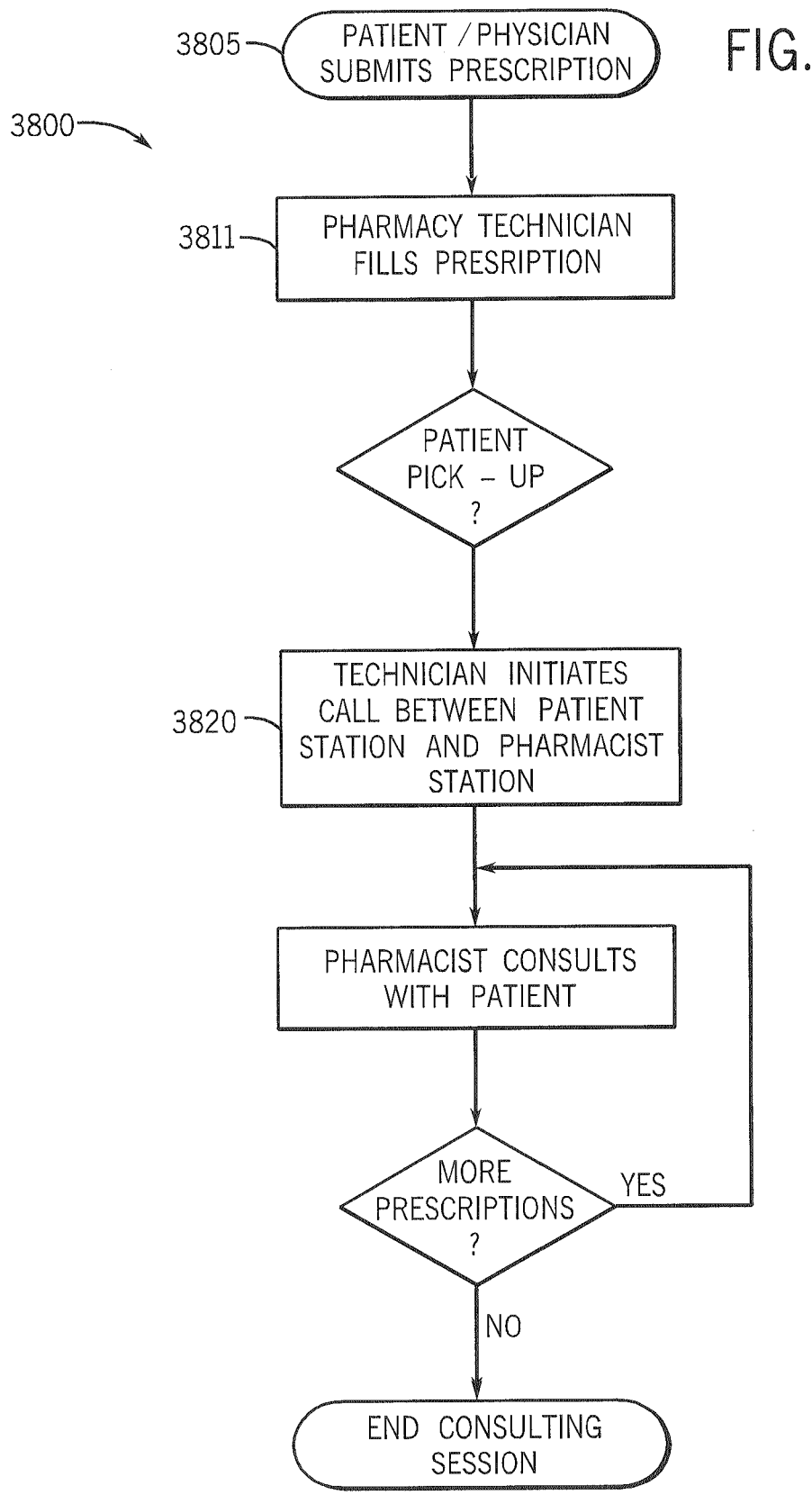
FIG. 38 is a flow diagram of an exemplary process between a first pharmacy patient station and a second pharmacy consultant station in a medical consulting system embodiment.

In some embodiments of the present invention, a patient station can be installed in a pharmacy where only pharmacy technicians work and a consultant station installed in another pharmacy where a licensed pharmacist is present. In current practice, pharmacy technicians typically fill prescriptions, but only licensed pharmacists consult with patients about questions they may have about the prescription. In such an embodiment, for example as shown in FIG. 38, the process 3800 begins with a patient or physician submitting a prescription at 3805. A pharmacy technician fills the prescription at 3810, after which a consultation is initiated between a patient station at the first pharmacy location and a licensed pharmacist at a second pharmacy location with a consultant station at 3820.

Embodiments of the remote medical consulting system provide a significant advancement in tele-medicine and enable physicians and other consultants to consult with patients without being in the same location. This not only addresses the current shortage of physicians, medical specialists and other consultants, but also enables medical services delivery in rural areas, war zones, and/or where medical resources and/or infrastructure are scarce. The remote medical consulting system provides tele-medicine services anywhere in the world and makes medical services available to more patients without significant travel. The retail pharmacy industry benefits by optimizing its investment in pharmacy buildings, providing extended healthcare options to the patients. Healthcare facilities can increase their presence without new buildings, new equipment and/or staffing with on-site medical staff. Patients enjoy significant economic benefits by avoiding unnecessary travel to remotely located healthcare facilities and gain access to various levels of medical consultation from their own location. On a global level, patients in other countries can consult with experts and specialists without having to travel to such countries where those experts reside.

In the area of manufacturing and industrial operations, embodiments of the visitor management station, remote medical consulting stations, and other systems described herein also can be utilized for remote operation of equipment and telematics. Telematics (the combination of telecommunications and informatics) refers to the collection of a defined set of data using equipment, devices, processes and components and then sending the collected data to a remote location. Most of this is done using automated processes. There are, however, situations when such automation does not work and human intervention is required to start, stop, assist in, reconfigure, or continue an operation. Oil drilling, dam operations, and industrial batch processing are some examples of telematics and batch operations which require human intervention from time to time to start, stop, assist in, reconfigure, or continue an operation. Any unplanned or non-programmed occurrence may require human intervention to get desired results. For example, in an industrial operation using a sequence of processing steps, malfunctions in one step or in the sequencing of such steps can lead to system-wide failures, snags, etc.

Figure 23:
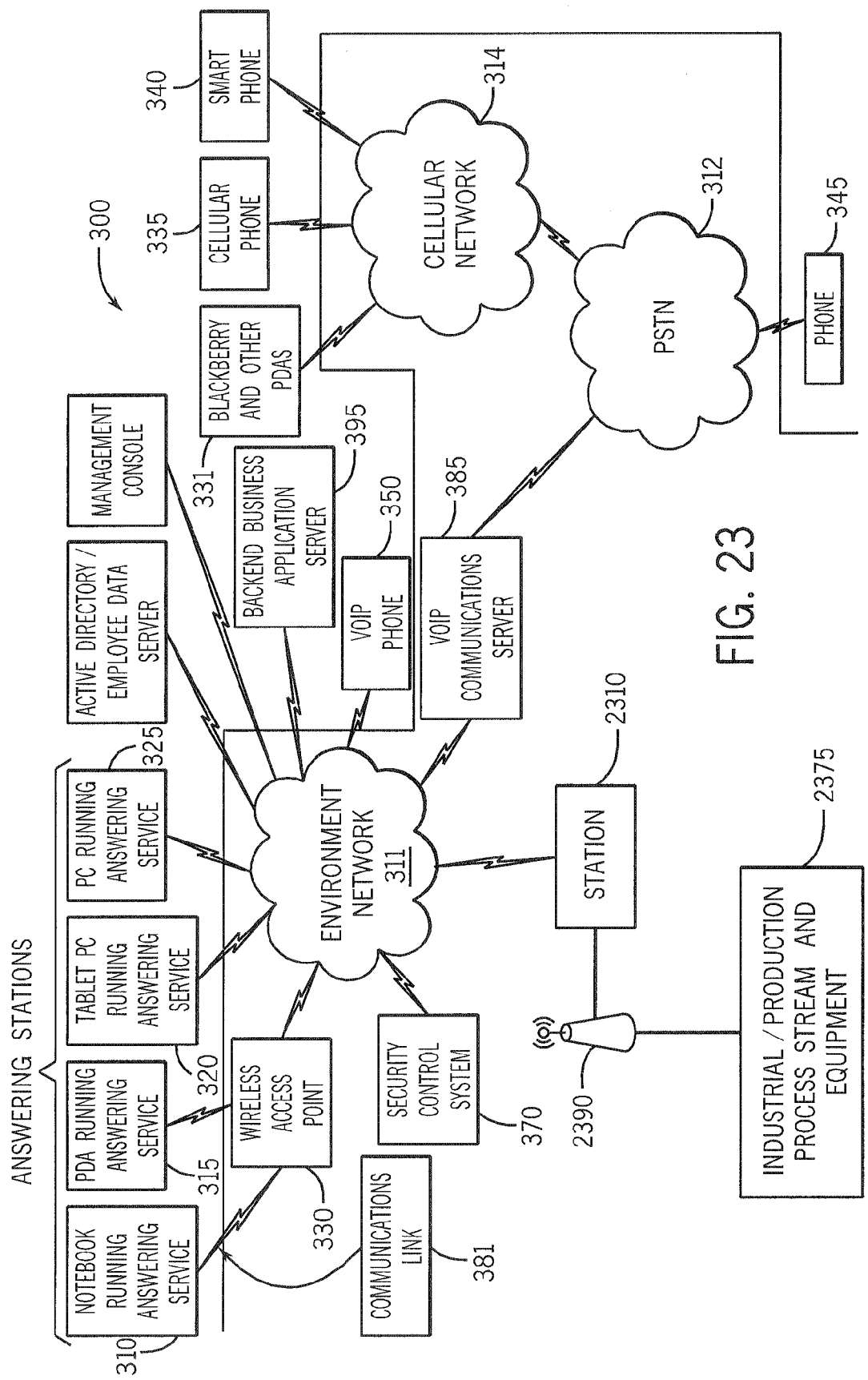
FIG. 23 is an exemplary telematics system embodiment used in connection with one or more industrial and/or production process streams and associated equipment.

Using the event handler assembly operation of visitor management system and consultant stations, above, human intervention can be provided using a telephone or cell phone dial pad, or by clicking buttons in answering station devices attached to a production or other network. An industrial/production process stream monitoring system 2300 is shown in FIG. 23, where an exemplary industrial and/or production process stream 2375 that implements batch operations or the like is monitored by a system monitor 2390 that provides process stream data to a system station 2301 configured similarly to the visitor stations, answering stations, consultant stations and patient stations described in connection with various embodiments above. When a malfunction or other problem is detected by monitor 2390, a message or other data is sent via network 311 to a remote control device (e.g., a cell phone 335, smart phone 340, PDA 331 or other remote control user device). As noted above, human intervention to address the malfunction and/or problem can be provided via a dial pad, touchpad, touch screen or other user input mechanism. These operations are similar to opening and closing a barrier such as doors, gates, etc. in the visitor management system and are similar to operation of a remote camera, vital sign gathering equipment, etc. in the remote medical consulting system. Such industrial embodiments enable people to monitor, run and troubleshoot production and manufacturing operations from remote locations. Such embodiments yield substantial savings by reducing down-time, allowing remote diagnosis of some types of problems and corrections, and by avoiding lost productivity, transportation expenses and/or isolation of staff of the individuals who otherwise would need to be on site to address such potential issues. Other industry and/or process-oriented solutions are obtained by inducing and or modifying the operational process defined in this disclosure.

Many features and advantages of the invention are apparent from the written description, and thus, the appended claims are intended to cover all such features and advantages. Further, numerous modifications and changes will readily occur to those skilled in the art, so the present invention is not limited to the exact operation and construction illustrated and described. Therefore, described embodiments are illustrative and not restrictive, and the invention should not be limited to the details given herein but should be defined by the following claims and their full scope of equivalents, whether foreseeable or unforeseeable now or in the future.

What is claimed is:

1. A management system for controlling visitor and vehicle access to an access-controlled environment via a plurality of access points, the access-controlled environment comprising first and second areas inside the environment, the system comprising:
    a network comprising one or more server devices and a memory device;
    a first vehicle access point for controlling vehicular access to the first and second areas inside the access-controlled environment, the vehicle access point comprising a vehicle barrier, a scanner, a vehicle scale and a camera;
    wherein the vehicle access point is configured to collect vehicle data, the vehicle data comprising:
        vehicle weight;
        a photograph of one or more vehicle parts;
        identification signature data from a vehicle responder, if available; and
        vehicle data, if any, stored in the memory device;
    further wherein the vehicle access point stores collected vehicle data in the memory device and, based on vehicle data collected at the vehicle access point, the vehicle access point;
    refuses vehicular access to the environment;
    grants vehicular access to the first area;
    grants vehicular access to the second area;
    a first visitor access point comprising a greeting station connected to the network and adjacent an entryway in a visitor access area of the environment, the greeting station comprising:

a video screen, a camera, a speaker and a microphone;
a visitor detection system configured to detect when a visitor has entered the visitor access area;
a visitor proximity system configured to detect when a visitor has approached the greeting station;
wherein the greeting station is configured to collect visitor data via the following:
one or more peripheral input devices;
one or more peripheral biometric data capture devices;
one or more visitor option selection devices;
visitor data, if any, stored in the network memory device; and
a plurality of answering stations, each answering station comprising:
a video screen, a speaker and a microphone;
wherein each answering station is configured to present an answering station operator with a plurality of options for dealing with a visitor calling from the greeting station based on collected visitor data, the plurality of options comprising at least one of the following:
conferencing with a visitor at the greeting station;
opening the entryway to grant a visitor access to the environment;
printing a visitor badge;
wherein the network is configured to prioritize available answering stations in the plurality of answering stations based on collected visitor data.

2. The system of claim 1 further comprising a phone system connected to the network, wherein the phone system is included in the prioritization of available answering stations.

3. The system of claim 2 wherein the visitor detection system and the visitor proximity system provide data to the greeting station to evaluate at least one of the following: visitor language limitations; visitor mobility limitations; visitor disabilities.

4. The system of claim 3 wherein the peripheral input devices at the greeting station comprise: a keyboard, a mouse, an RFID scanner, a touch screen, an image scanner, a barcode reader.

5. The system of claim 4 wherein the visitor data comprises at least one of the following: a visitor name, a visitor company affiliation, one or more physical disabilities of a visitor, language limitations of a visitor, visitor biometric data, scanned document information.

6. The system of claim 5 wherein the visitor option selection devices comprise one or more of the following configured to allow employee entry, general inquiries and customer service, directory assistance to find a particular individual with who to speak, mail and goods delivery, and pre-scheduled visitor appointments: a touch screen, a keyboard, a voice-activated control, a mouse.

7. The system of claim 1 wherein the first area is a registration area configured to perform at least one of the following: collect visitor data, collect additional vehicle data, register a vehicle, register a visitor, obtain instructions for a visit.

8. The system of claim 7 further comprising a plurality of digital signs configured to provide instructions to vehicles and vehicle operators inside the environment, the plurality of digital signs being connected to the network and the instructions being based on collected vehicle and visitor data.

9. The system of claim 8 further comprising:
a plurality of responders, wherein each responder has a unique identification signature; and
a plurality of scanners, wherein each scanner is configured to detect a responder identification signature and to provide position data about the position of each responder to the network.

10. The system of claim 1 further comprising:
a scanner matrix inside the environment, the scanner matrix connected to the network;
a plurality of responders, wherein each responder comprises a unique identification signature;
wherein the visitor monitoring system is configured to collect tracking data for each responder, the tracking data comprising;
positional data comprising mapping each responder's position in the scanner matrix; and
temporal data comprising timestamps associated with the positional data;
wherein the combination of positional data and temporal data provides a record of movement of each responder throughout the scanner matrix and any departures of a responder from the scanner matrix;
a display monitor connected to the network, wherein the display monitor is configured to display the position of each responder in the environment.

11. The system of claim 10 wherein the scanner matrix comprises at least one of the following: a 3-dimensional matrix in one or more buildings; an array of scanners along roads and paths traveled by vehicles in the environment.

12. The system of claim 10 further comprising digital signage inside the environment, wherein the digital signage is configured to provide assistance and instructions from the network in response to detection of a specific responder by the scanner matrix.

13. The system of claim 12 further comprising:
one or more responder dispensers on a periphery of the environment or in the environment, wherein each responder dispenser is configured to physically dispense responders when authorized to do so by the network, and further wherein the network maintains identification signature data for each responder that is dispensed and associates identification signature data with visitor data or vehicle data for the visitor or vehicle to which a responder is dispensed; and
one or more responder collectors on a periphery of the environment or in the environment, wherein each responder collector is configured to physically receive responders when returned by a visitor or vehicle, and further wherein the network maintains identification signature data for each responder that is collected and associates the collected responder identification signature data with the visitor data or vehicle data for the visitor or vehicle to which a responder was dispensed.

14. A method for controlling visitor and vehicle access to an access-controlled environment via a plurality of access points, the access-controlled environment comprising first and second areas inside the environment, the method utilizing a network comprising one or more server devices and a memory device, the method comprising:
controlling vehicular access to first and second areas inside the access-controlled environment at a vehicle access point, the vehicle access point comprising a vehicle barrier, a scanner, a vehicle scale and a camera;
the vehicle access point collecting vehicle data comprising:
vehicle weight;
a photograph of one or more vehicle parts;
identification signature data from a vehicle responder, if available; and
vehicle data, if any, stored in the memory device;
the vehicle access point storing collected vehicle data in the memory device and, based on vehicle data collected at the vehicle access point, the vehicle access point:

refusing vehicular access to the environment;
granting vehicular access to the first area;
granting vehicular access to the second area;
controlling visitor access to the access-controlled environment at a first visitor access point comprising a greeting station connected to the network and adjacent an entryway in a visitor access area of the environment, the greeting station comprising a video screen, a camera, a speaker and a microphone:
  a visitor detection system detecting when a visitor has entered the visitor access area;
  a visitor proximity system detecting when a visitor has approached the greeting station;
  the greeting station collecting visitor data via the following:
    one or more peripheral input devices;
    one or more peripheral biometric data capture devices;
    one or more visitor option selection devices;
    visitor data, if any, stored in the network memory device; and
based on collected visitor data, the network prioritizing available answering stations in a plurality of answering stations, wherein each answering station comprises a video screen, a speaker and a microphone and further wherein each answering station presents an answering station operator with a plurality of options for dealing with a visitor caning from the greeting station based on collected visitor data, the plurality of options comprising at least one of the following:
  conferencing with a visitor at the greeting station;
  opening the entryway to grant a visitor access to the environment;
  printing a visitor badge.

15. The method of claim 14 further comprising providing an emergency notification to selected visitors and vehicles in the access-controlled environment using a plurality of digital signs.

16. The system of claim 1 wherein prioritizing available answering stations in the plurality of answering stations based on collected visitor data comprises performing a skills-based evaluation of the resources and capabilities of individuals associated with the plurality of answering stations.

* * * * *